United States Patent
Bell et al.

(10) Patent No.: US 9,610,549 B2
(45) Date of Patent: *Apr. 4, 2017

(54) POLYCYCLO-OLEFINIC BLOCK COPOLYMERS

(71) Applicants: PROMERUS, LLC, Brecksville, OH (US); SUMITOMO BAKELITE CO., LTD, Shinagawa-Ku, Tokyo (JP)

(72) Inventors: Andrew Bell, Brecksville, OH (US); Tamami Takigawa, Tokyo (JP)

(73) Assignees: PROMERUS, LLC, Brecksville, OH (US); SUMITOMO BAKELITE CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/827,599

(22) Filed: Aug. 17, 2015

(65) Prior Publication Data

US 2016/0046752 A1    Feb. 18, 2016

Related U.S. Application Data

(60) Provisional application No. 62/037,809, filed on Aug. 15, 2014, provisional application No. 62/037,823, filed on Aug. 15, 2014, provisional application No. 62/037,828, filed on Aug. 15, 2014, provisional application No. 62/073,013, filed on Oct. 31, 2014.

(51) Int. Cl.
| | |
|---|---|
| *C08F 299/02* | (2006.01) |
| *B01D 71/80* | (2006.01) |
| *C07F 15/00* | (2006.01) |
| *C08F 32/04* | (2006.01) |
| *B01D 61/36* | (2006.01) |
| *B01D 67/00* | (2006.01) |
| *B01D 69/08* | (2006.01) |
| *B01D 69/12* | (2006.01) |
| *C08F 4/80* | (2006.01) |

(52) U.S. Cl.
CPC .......... *B01D 71/80* (2013.01); *B01D 61/362* (2013.01); *B01D 67/0002* (2013.01); *B01D 67/0009* (2013.01); *B01D 67/0095* (2013.01); *B01D 69/08* (2013.01); *B01D 69/087* (2013.01); *B01D 69/12* (2013.01); *B01D 69/125* (2013.01); *C07F 15/006* (2013.01); *C08F 32/04* (2013.01); *C08F 299/02* (2013.01); *B01D 2323/12* (2013.01); *B01D 2323/36* (2013.01); *C08F 4/80* (2013.01)

(58) Field of Classification Search
None
See application file for complete search history.

(56) References Cited

U.S. PATENT DOCUMENTS

| | | | | |
|---|---|---|---|---|
| 5,475,060 | A * | 12/1995 | Brekner | ............... C08F 297/08 525/289 |
| 7,022,790 | B2 * | 4/2006 | Elce | ................. C08G 59/3218 526/281 |
| 2008/0085979 | A1 | 4/2008 | Ohkita | |
| 2014/0042090 | A1 | 2/2014 | Bell | |

OTHER PUBLICATIONS

Breunig, S. Die Makromolecular Chemie vol. 193 pp. 2915-2927 (Nov. 1992).*
Safir, A.L. et al. Macromolecules vol. 28 pp. 5396-5398 (Jul. 1995).*
Schroers, M. et al. Polymer Materials: Science and Engineering vol. 84 pp. 761-762 (2001).*

* cited by examiner

*Primary Examiner* — Irina S Zemel
*Assistant Examiner* — Jeffrey Lenihan
(74) *Attorney, Agent, or Firm* — Balaram Gupta

(57) ABSTRACT

A series of vinyl addition block polymers derived from functionalized norbornene monomers are disclosed and claimed. Specifically, a series of diblock and triblock polymers derived from norbornene monomers are disclosed. Also disclosed are the method of preparation of such block polymers, and their use in the fabrication of membranes which exhibit unique separation properties.

20 Claims, 4 Drawing Sheets

POLYCYCLO-OLEFINIC BLOCK COPOLYMERS

CROSS REFERENCE TO RELATED APPLICATIONS

This application claims the benefit of U.S. Provisional Application No. 62/037,809, filed Aug. 15, 2014, U.S. Provisional Application No. 62/037,823, filed Aug. 15, 2014, U.S. Provisional Application No. 62/037,828, filed Aug. 15, 2014, and U.S. Provisional Application No. 62/073,013, filed Oct. 31, 2014, all of which are incorporated herein by reference in their entirety.

BACKGROUND OF THE INVENTION

Field of the Invention

The present invention relates to a series of block polymers derived from cyclo-olefinic monomers. More specifically, the present invention relates to a series of block polymers derived from a variety of functionalized norbornene-type monomers and their utility in a variety of applications including membranes.

Description of the Art

Cyclic olefin polymers, such as polynorbornenes (PNBs), are widely used in a variety of electronic, optoelectronic and other applications, and therefore, methods of making such PNBs in an industrial scale are gaining importance. It is well known in the literature that various functionalized PNBs can be synthesized by employing suitable starting norbornene monomers by addition polymerization using a variety of transition metal catalysts and procatalysts. See for example, U.S. Pat. No. 7,989,570, pertinent portions of which are incorporated herein by reference.

However, in order to manufacture functionalized PNBs in an industrial scale, there is a need for catalyst or catalyst system to meet certain desirable characteristics. A few of such characteristics, include among others, a) a living catalyst polymerization system, that is, the catalyst retains its activity even after reaching very high degree of chain growth leading to very high molecular weight polymer; b) high activity of the catalysts system even at a very high monomer to catalyst molar ratio; c) effective chain transfer to control molecular weight; d) good catalyst stability during polymerization, including thermal and chemical stability, that is, no termination of the polymerization activity; e) fast polymerization kinetics, that is, fast chain propagation preferably at around room temperature; and f) storage stable components, such as for example, stable A and B components, for highly reactive catalyst systems.

U.S. Pat. No. 6,936,672 discloses a variety of catalysts, procatalysts, and catalyst systems for the polymerization of polycyclic olefins. However, these catalyst systems may not be suitable for the preparation of highly ordered block copolymers as described herein.

Accordingly, it is an object of this invention to provide a series of substituted or unsubstituted bicycloalkylene-palladium compounds having utility as addition polymerization catalysts as a single component or a bicomponent system.

It is also an object of this invention to provide processes for the preparation of the substituted bicycloalkene-palladium compounds as disclosed herein.

It is further an object of this invention to provide a series of novel block copolymers having unique properties for a variety of applications in the fabrication of electronic, opto-electronic devices and for the formation of membranes having unique properties for a variety of applications.

Other objects and further scope of the applicability of the present invention will become apparent from the detailed description that follows.

SUMMARY OF THE INVENTION

Advantageously it has now been found that various block copolymers as described herein can be prepared by a few of the organopalladium compounds as described herein as well as various other catalysts known in the art. It has further been found that the block copolymers of this invention provide unique advantages and therefore find utility in a variety of applications including but not limited to forming membrane materials and in various other optical and electronic applications, among others. The membranes formed from the block copolymers are useful for example in separation of organics from biomass or other organic wastes.

Accordingly, there is provided a block copolymer of the formula (VI):

$$(A)_m\text{-}b\text{-}(B)_n \quad (VI);$$

where m and n are integers of at least 15 but in other embodiments m and n can range from 20 to 4000, or from 50 to 3000 or 100 to 2000, and in other embodiments m and n can also be higher than 4000 depending upon the intended use;

b denotes a bond between the two blocks of homopolymers A and B;

A and B are different from each other and independently selected from a repeat unit represented by formula (IVA), said repeat unit is derived from a monomer of formula (IV):

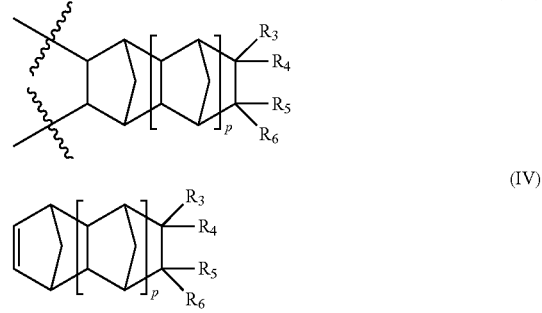

wherein:

$\sim\!\!\sim\!\!\sim$ denotes a place of bonding with another repeat unit;

p is an integer 0, 1 or 2;

$R_3$, $R_4$, $R_5$ and $R_6$ are the same or different and each independently of one another is selected from hydrogen, linear or branched $(C_1\text{-}C_{16})$alkyl, hydroxy$(C_1\text{-}C_6)$alkyl, perfluoro$(C_1\text{-}C_{12})$alkyl, $(C_3\text{-}C_{12})$cycloalkyl, $(C_6\text{-}C_{12})$bicycloalkyl, $(C_7\text{-}C_{14})$tricycloalkyl, $(C_6\text{-}C_{10})$aryl, $(C_6\text{-}C_{10})$aryl$(C_1\text{-}C_3)$alkyl, perfluoro$(C_6\text{-}C_{10})$aryl, perfluoro$(C_6\text{-}C_{10})$aryl$(C_1\text{-}C_3)$alkyl, di$(C_1\text{-}C_2)$alkylmaleimide$(C_3\text{-}C_6)$alkyl, di$(C_1\text{-}C_2)$alkylmaleimide$(C_2\text{-}C_6)$alkoxy$(C_1\text{-}C_2)$alkyl hydroxy, $(C_1\text{-}C_{12})$alkoxy, $(C_3\text{-}C_{12})$cycloalkoxy, $(C_6\text{-}C_{12})$bicycloalkoxy, $(C_7\text{-}C_{14})$tricycloalkoxy, $(C_6\text{-}C_{10})$aryloxy$(C_1\text{-}C_3)$alkyl, $(C_5\text{-}C_{10})$heteroaryloxy$(C_1\text{-}C_3)$alkyl, $(C_6\text{-}C_{10})$aryloxy, $(C_5\text{-}C_{10})$heteroaryloxy or $(C_1\text{-}C_6)$acyloxy, where each of the aforementioned substituents are optionally substituted with a group selected from halogen or hydroxy.

In another aspect of this invention there is also provided a triblock polymer represented is by formula (VII):

$$(A)_m\text{-}b\text{-}(B)_n\text{-}b\text{-}(C)_o \quad (VII);$$

where m, n and b are as defined above and o is an integer of at least 15, but in other embodiments o can range from 20 to 4000, or from 50 to 3000 or 100 to 2000, and in other embodiments o can also be higher than 4000 depending upon the intended use of the block polymer. C is same or different from A or B and independently selected from a repeat unit represented by formula (IVA), said repeat unit is derived from a monomer of formula (IV) as defined herein.

BRIEF DESCRIPTION OF THE DRAWINGS

Embodiments in accordance with the present invention are described below with reference to the following accompanying figures and/or images. Where drawings are provided, it will be drawings which are simplified portions of various embodiments of this invention and are provided for illustrative purposes only.

DETAILED DESCRIPTION

Figure 1:
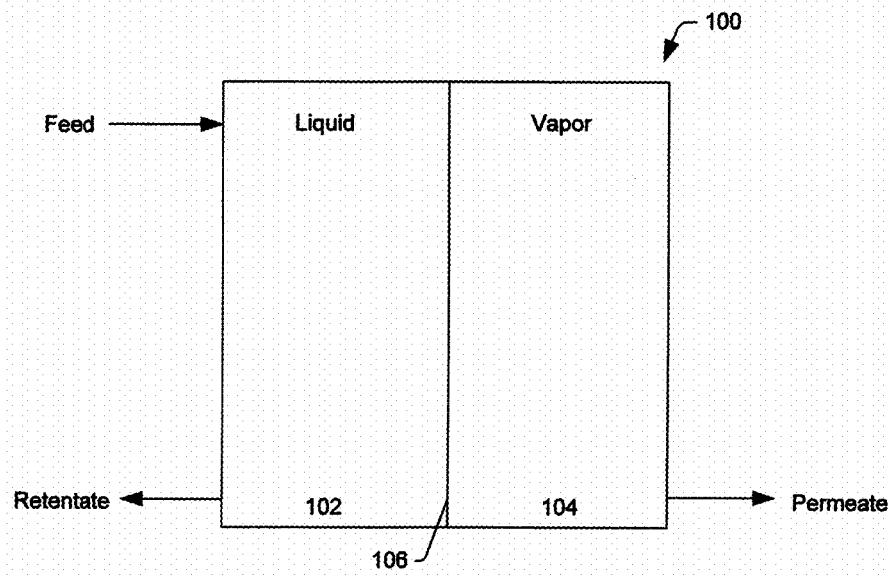
FIG. 1 depicts a pervaporation module in accordance with embodiments of the invention.

The terms as used herein have the following meanings:

As used herein, the articles "a," "an," and the include plural referents unless otherwise expressly and unequivocally limited to one referent.

Since all numbers, values and/or expressions referring to quantities of ingredients, reaction conditions, etc., used herein and in the claims appended hereto, are subject to the various uncertainties of measurement encountered in obtaining such values, unless otherwise indicated, all are to be understood as modified in all instances by the term "about."

Where a numerical range is disclosed herein such range is continuous, inclusive of both the minimum and maximum values of the range as well as every value between such minimum and maximum values. Still further, where a range refers to integers, every integer between the minimum and maximum values of such range is included. In addition, where multiple ranges are provided to describe a feature or characteristic, such ranges can be combined. That is to say that, unless otherwise indicated, all ranges disclosed herein are to be understood to encompass any and all sub-ranges subsumed therein. For example, a stated range of from "1 to 10" should be considered to include any and all sub-ranges between the minimum value of 1 and the maximum value of 10. Exemplary sub-ranges of the range 1 to 10 include, but are not limited to, 1 to 6.1, 3.5 to 7.8, and 5.5 to 10, etc.

As used herein, the symbol "⁓⁓⁓" denotes a position at which the bonding takes place with another repeat unit or another atom or molecule or group or moiety as appropriate with the structure of the group as shown.

As used herein, "hydrocarbyl" refers to a radical of a group that contains carbon and hydrogen atoms, non-limiting examples being alkyl, cycloalkyl, aryl, aralkyl, alkaryl, and alkenyl. The term "halohydrocarbyl" refers to a hydrocarbyl group where at least one hydrogen has been replaced by a halogen. The term perhalocarbyl refers to a hydrocarbyl group where all hydrogens have been replaced by a halogen.

As used herein, the expression "$(C_1-C_6)$alkyl" includes methyl and ethyl groups, and straight-chained or branched propyl, butyl, pentyl and hexyl groups. Particular alkyl groups are methyl, ethyl, n-propyl, isopropyl and tert-butyl. Derived expressions such as "$(C_1-C_4)$alkoxy", "$(C_1-C_4)$thioalkyl" "$(C_1-C_4)$alkoxy$(C_1-C_4)$alkyl", "hydroxy$(C_1-C_4)$alkyl", "$(C_1-C_4)$alkyl-carbonyl", "$(C_1-C_4)$alkoxycarbonyl$(C_1-C_4)$alkyl", "$(C_1-C_4)$alkoxycarbonyl", "amino$(C_1-C_4)$-alkyl", "$(C_1-C_4)$alkylamino", "$(C_1-C_4)$alkylcarbamoyl$(C_1-C_4)$alkyl", "$(C_1-C_4)$dialkylcarbamoyl-$(C_1-C_4)$alkyl" "mono- or di-$(C_1-C_4)$alkylamino$(C_1-C_4)$alkyl", "amino$(C_1-C_4)$alkylcarbonyl" "diphenyl$(C_1-C_4)$alkyl", "phenyl$(C_1-C_4)$alkyl", "phenylcarboyl$(C_1-C_4)$alkyl" and "phenoxy-$(C_1-C_4)$alkyl" are to be construed accordingly.

As used herein, the expression "cycloalkyl" includes all of the known cyclic radicals. Representative examples of "cycloalkyl" includes without any limitation cyclopropyl, cyclobutyl, cyclopentyl, cyclohexyl, cycloheptyl, cyclooctyl, and the like. Derived expressions such as "cycloalkoxy", "cycloalkylalkyl", "cycloalkylaryl", "cycloalkylcarbonyl" are to be construed accordingly.

As used herein, the expression "$(C_2-C_6)$alkenyl" includes ethenyl and straight-chained or branched propenyl, butenyl, pentenyl and hexenyl groups. Similarly, the expression "$(C_2-C_6)$alkynyl" includes ethynyl and propynyl, and straight-chained or branched butynyl, pentynyl and hexynyl groups.

As used herein the expression "$(C_1-C_4)$acyl" shall have the same meaning as "$(C_1-C_4)$alkanoyl", which can also be represented structurally as "R—CO—," where R is a $(C_1-C_3)$alkyl as defined herein. Additionally, "$(C_1-C_3)$alkylcarbonyl" shall mean same as $(C_1-C_4)$acyl. Specifically, "$(C_1-C_4)$acyl" shall mean formyl, acetyl or ethanoyl, propanoyl, n-butanoyl, etc. Derived expressions such as "$(C_1-C_4)$acyloxy" and "$(C_1-C_4)$acyloxyalkyl" are to be construed accordingly.

As used herein, the expression "$(C_1-C_6)$perfluoroalkyl" means that all of the hydrogen atoms in said alkyl group are replaced with fluorine atoms. Illustrative examples include trifluoromethyl and pentafluoroethyl, and straight-chained or branched heptafluoropropyl, nonafluorobutyl, undecafluoropentyl and tridecafluorohexyl groups. Derived expression, "$(C_1-C_6)$perfluoroalkoxy", is to be construed accordingly.

As used herein, the expression "$(C_6-C_{10})$aryl" means substituted or unsubstituted phenyl or naphthyl. Specific examples of substituted phenyl or naphthyl include o-, p-, m-tolyl, 1,2-, 1,3-, 1,4-xylyl, 1-methylnaphthyl, 2-methylnaphthyl, etc. "Substituted phenyl" or "substituted naphthyl" also include any of the possible substituents as further defined herein or one known in the art. Derived expression, "($C_6$-$C_{10}$)arylsulfonyl," is to be construed accordingly.

As used herein, the expression "($C_6$-$C_{10}$)aryl($C_1$-$C_4$)alkyl" means that the ($C_6$-$C_{10}$)aryl as defined herein is further attached to ($C_1$-$C_4$)alkyl as defined herein. Representative examples include benzyl, phenylethyl, 2-phenylpropyl, 1-naphthylmethyl, 2-naphthylmethyl and the like. It should be further noted that the expressions "arylalkyl" and "aralkyl" mean the same are used interchangeably. Accordingly, the expression "($C_6$-$C_{10}$)aryl($C_1$-$C_4$)alkyl" can also be construed as "($C_6$-$C_{14}$)aralkyl."

As used herein, the expression "heteroaryl" includes all of the known heteroatom containing aromatic radicals. Representative 5-membered heteroaryl radicals include furanyl, thienyl or thiophenyl, pyrrolyl, pyrazolyl, imidazolyl, oxazolyl, thiazolyl, isothiazolyl, and the like. Representative 6-membered heteroaryl radicals include pyridinyl, pyridazinyl, pyrimidinyl, pyrazinyl, triazinyl, and the like radicals. Representative examples of bicyclic heteroaryl radicals include, benzofuranyl, benzothiophenyl, indolyl, quinolinyl, isoquinolinyl, cinnolyl, benzimidazolyl, indazolyl, pyridofuranyl, pyridothienyl, and the like radicals.

As used herein, the expression "heterocycle" includes all of the known reduced heteroatom containing cyclic radicals. Representative 5-membered heterocycle radicals include tetrahydrofuranyl, tetrahydrothiophenyl, pyrrolidinyl, 2-thiazolinyl, tetrahydrothiazolyl, tetrahydrooxazolyl, and the like. Representative 6-membered heterocycle radicals include piperidinyl, piperazinyl, morpholinyl, thiomorpholinyl, and the like. Various other heterocycle radicals include, without limitation, aziridinyl, azepanyl, diazepanyl, diazabicyclo[2.2.1]hept-2-yl, and triazocanyl, and the like.

"Halogen" or "halo" means chloro, fluoro, bromo, and iodo.

In a broad sense, the term "substituted" is contemplated to include all permissible substituents of organic compounds. In a few of the specific embodiments as disclosed herein, the term "substituted" means substituted with one or more substituents independently selected from the group consisting of $C_{1-6}$alkyl, $C_{2-6}$alkenyl, $C_{1-6}$perfluoroalkyl, phenyl, hydroxy, —$CO_2$H, an ester, an amide, $C_1$-$C_6$alkoxy, $C_1$-$C_6$thioalkyl, $C_1$-$C_6$perfluoroalkoxy, —$NH_2$, Cl, Br, I, F, —NH-lower alkyl, and —N(lower alkyl)$_2$. However, any of the other suitable substituents known to one skilled in the art can also be used in these embodiments.

It should be noted that any atom with unsatisfied valences in the text, schemes, examples and tables herein is assumed to have the appropriate number of hydrogen atom(s) to satisfy such valences.

As used herein the term, "living polymerization" means that a chain growth polymerization where the ability of a growing polymer chain to terminate has been removed. That is to say, in this system both chain termination and chain transfer reaction are absent and the rate of chain initiation is also much larger than the rate of chain propagation, which results in growth of polymer chains at a more constant rate than seen in traditional chain polymerization and their lengths remain very similar (i.e., they have a very low polydispersity index, PDI).

As used herein the terms, "block copolymer" or "block polymer" are used interchangeably and mean the same, that is, two or more homopolymer subunits are linked by covalent bonds. Accordingly, "diblock copolymer" can be represented by -(A)$_m$-b-(B)$_n$—, where homopolymer of formula A is linked by a single bond with a homopolymer of formula B, and m and n are respective numbers of monomer repeat units. Thus, in this "diblock copolymer" representation "b" denotes a "block" of preceding homopolymer (A)$_m$ is linked by a covalent bond with a succeeding homopolymer (B)$_n$. Accordingly, the designation "-b-" should be construed as a bond between the designated polymeric blocks. Similarly, "triblock copolymer," "tetrablock copolymer," and so on, should be construed accordingly. Further, "diblock copolymer" or "diblock polymer" are used interchangeably.

As used herein, the terms "polymer composition," "copolymer composition," "terpolymer composition" or "tetrapolymer composition" are used herein interchangeably and are meant to include at least one synthesized polymer, copolymer, terpolymer, or tetrapolymer, as well as residues from initiators, solvents or other elements attendant to the synthesis of such polymers, where such residues are understood as not necessarily being covalently incorporated thereto. But some catalysts or initiators may sometimes be covalently bound to a part of the polymeric chain either at the beginning and/or end of the polymeric chain, Such residues and other elements considered as part of the "polymer" or "polymer composition" are typically mixed or co-mingled with the polymer such that they tend to remain therewith when it is transferred between vessels or between solvent or dispersion media. A polymer composition can also include materials added after synthesis of the polymer to provide or modify specific properties of such composition. Such materials include, hut are not limited to solvent(s), antioxidant(s), photoinitiator(s), sensitizers and other materials as will be discussed more fully below.

By the term, "a monomer repeat unit is derived" is meant that the polymeric repeating units are polymerized (formed) from, e.g., polycyclic norbornene-type monomers, wherein the resulting polymers are formed by 2,3 enchainment of norbornene-type monomers as shown below:

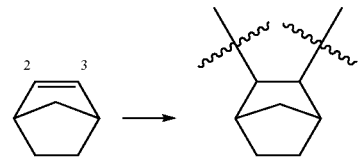

Catalysts/Polymerization Initiators

Thus, in accordance with the practice of this invention there is provided a compound of the formula I:

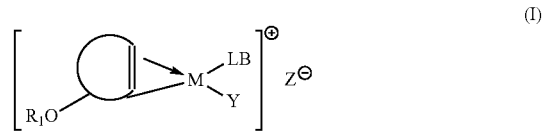

wherein,

is $(C_5\text{-}C_{10})$cycloalkene, $(C_7\text{-}C_{12})$bicycloalkene or $(C_8\text{-}C_{12})$ tricycloalkene group;

M is nickel, palladium or platinum;

LB is a Lewis Base;

$Z^\ominus$ is a weakly coordinating anion;

Y is $PR_3$ or $O=PR_3$, where R is independently selected from methyl, ethyl, $(C_3\text{-}C_6)$alkyl, substituted or unsubstituted $(C_3\text{-}C_7)$cycloalkyl, $(C_6\text{-}C_{10})$aryl, $(C_6\text{-}C_{10})$aralkyl, methoxy, ethoxy, $(C_3\text{-}C_6)$alkoxy, substituted or unsubstituted $(C_3\text{-}C_7)$cycloalkoxy, $(C_6\text{-}C_{10})$aryloxy or $(C_6\text{-}C_{10})$aralkyloxy; and $R_1$ is methyl, ethyl, linear or branched $(C_3\text{-}C_6)$alkyl, $(C_6\text{-}C_{10})$aryl, $(C_6\text{-}C_{10})$aralkyl or $R_2CO$, where $R_2$ is methyl, ethyl or $(C_3\text{-}C_6)$alkyl.

In another embodiment of this invention a variety of cycloalkene, bicycloalkene or tricycloalkene groups can be employed as

group in compound of formula (I). Representative examples of $(C_5\text{-}C_{10})$cycloalkene group include without any limitation, cyclopentene, cyclohexene, cycloheptene, cyclooctene, cyclononene or cyclodecene. However, other suitable cycloalkene groups including cycloundecene, cyclododecene, and the like can also be employed. Representative examples of $(C_7\text{-}C_{12})$bicycloalkene group include without any limitation, bicyclo[2,2,1]heptene, bicyclo[3,2,1]octene, bicyclo[2,2,2]octene, bicyclo[3,2,2]nonene, bicyclo[3,3,1] nonene, 1,2,3,3a,4,6a-hexahydropentalene, 3a,4,5,6,7,7a-hexahydro-1H-indene, 1,2,3,4,4a,5,8,8a-octahydronaphthalene, 2,3,4,4a,5,6,9,9a-octahydro-1H-benzo[7]annulene, and the like. Representative examples of $(C_8\text{-}C_{12})$tricycloalkene group include without any limitation, dicyclopentadiene, (4s,7s)-3a,4,5,6,7,7a-hexahydro-1H-4,7-ethanoindene, and the like. In addition, any of the substituted cycloalkenes, bicycloalkenes or tricycloalkenes of the foregoing can also be employed.

In another embodiment of this invention the M can be other than nickel, palladium or platinum. Suitable M include any of the Group X transition metal or Group IX metal, such as for example, cobalt, rhodium or iridium.

In another embodiment of this invention the compounds of formula (I) includes a Lewis Base, which is coordinately bonded to the metal atom, M. That is, the Lewis Base is bonded to the metal atom by sharing both of its lone pair of electrons. Any of the Lewis Base known in the art can be used for this purpose. Advantageously, it has now been found that a Lewis Base, which can dissociate readily under the polymerization conditions as described further in detail below generally provides more suitable compounds of formula (I) as polymerization catalysts, i.e., initiators. Thus, in one aspect of this invention judicious selection of the Lewis Base will provide a modulation of the catalytic activity of the compounds of this invention.

Accordingly, it has now been found that suitable LBs that can be employed include without any limitation substituted and unsubstituted nitrites, including alkyl nitrite, aryl nitrite or aralkyl nitrite; phosphine oxides, including substituted and unsubstituted trialkyl phosphine oxides, triaryl phosphine oxides, triaralkyl phosphine oxides, and various combinations of alkyl, aryl and aralkyl phosphine oxides; substituted and unsubstituted pyrazines; substituted and unsubstituted pyridines; phosphites, including substituted and unsubstituted trialkyl phosphites, triaryl phosphites, triaralkyl phosphites, and various combinations of alkyl, aryl and aralkyl phosphites; phosphines, including substituted and unsubstituted trialkyl phosphines, triaryl phosphines, triaralkyl phosphines, and various combinations of alkyl, aryl and aralkyl phosphines. Various other LBs that may be employed include various ethers, alcohols, ketones, amines and anilines, arsines, stibines, and the like.

In some embodiments of this invention, the LB is selected from acetonitrile, propionitrile, n-butyronitrile, tert-butyronitrile, benzonitrile ($C_6H_5CN$), 2,4,6-trimethylbezonitrile, phenyl acetonitrile ($C_6H_5CH_2CN$), pyridine, 2-methylpyridine, 3-methylpyridine, 4-methylpyridine, 2,3-dimethylpyridine, 2,4-dimethylpyridine, 2,5-dimethylpyridine, 2,6-dimethylpyridine, 3,4-dimethylpyridine, 3,5-dimethylpyridine, 2,6-di-t-butylpyridine, 2,4-di-t-butylpyridine, 2-methoxypyridine, 3-methoxypyridine, 4-methoxypyridine, pyrazine, 2,3,5,6-tetramethylpyrazine, diethyl ether, di-n-butyl ether, dibenzyl ether, tetrahydrofuran, tetrahydropyran, benzophenone, triphenylphosphine oxide, triphenyl phosphate or phosphines or phosphites of formula $PR_3$, where R is independently selected from methyl, ethyl, $(C_3\text{-}C_6)$alkyl, substituted or unsubstituted $(C_3\text{-}C_7)$cycloalkyl, $(C_6\text{-}C_{10})$aryl, $(C_6\text{-}C_{10})$aralkyl, methoxy, ethoxy, $(C_3\text{-}C_6)$alkoxy, substituted or unsubstituted $(C_3\text{-}C_7)$ cycloalkoxy, $(C_6\text{-}C_{10})$aryloxy and $(C_6\text{-}C_{10})$aralkyloxy. Representative examples of $PR_3$ include without any limitation trimethyl phosphine, triethyl phosphine, tri-n-propyl phosphine, tri-iso-propyl phosphine, tri-n-butyl phosphine, tri-iso-butyl phosphine, tri-tert-butyl phosphine, tricyclopentylphosphine, triallylphosphine, tricyclohexylphosphine, triphenyl phosphine, trimethyl phosphite, triethyl phosphite, tri-n-propyl phosphite, tri-iso-propyl phosphite, tri-n-butyl phosphite, tri-iso-butyl phosphite, tri-tert-butyl phosphite, tricyclopentylphosphite, triallylphosphite, tricyclohexylphosphite, triphenyl phosphite, and the like. It should however be noted that various other known LBs which will bring about the intended activity can also be used in this embodiment of the invention.

The phosphine ligands can also be selected from phosphine compounds that are water soluble thereby imparting the resulting catalysts with solubility in aqueous media. Selected phosphines of this type include but are not limited to carboxylic substituted phosphines such as 4-(diphenylphosphine)benzoic acid, and 2-(diphenylphosphine)benzoic acid, sodium 2-(dicyclohexylphosphino)ethanesulfonate, 4,4'-(phenylphosphinidene)bis(benzene sulfonic acid) dipotassium salt, 3,3',3''-phosphinidynetris(benzene sulfonic acid) trisodium salt, 4-(dicyclohexylphosphino)-1,1-dimethylpiperidinium chloride, 4-(dicyclohexylphosphino)-1,1-dimethylpiperidinium iodide, quaternary amine-functionalized salts of phosphines such as 2-(dicyclohexylphosphino)-N,N,N-trimethylethanaminium chloride, 2,2'-(cyclohexylphosphinidene)bis[N,N,N-trimethylethanaminium dichloride, 2,2'-(cyclohexylphosphinidene)-bis(N,N,N-trimethylethanaminium) diiodide, and 2-(dicyclohexylphosphino)-N,N,N-trimethylethanaminium iodide.

Other examples of organophosphorus compounds suitable as LBs include phosphinite and phosphonate ligands. Representative examples of phosphinite ligands include but are not limited to methyl diphenylphosphinite, ethyl diphenylphosphinite, isopropyl diphenylphosphinite, and phenyl diphenylphosphinite. Representative examples of phosphonite ligands include but are not limited to diphenyl phenylphosphonite, dimethyl phenylphosphonite, diethyl methylphosphonite, diisopropyl phenylphosphonite, and diethyl phenylphosphonite.

In a further aspect of this invention, it has now been found that the compound of formula (I) having a counter anion, $Z^\ominus$ which is a weakly coordinating anion (WCA) provides better catalytic (i.e., initiator) activity. That is, the WCA is an anion which is only weakly coordinated to the cation complex. It is sufficiently labile to be displaced by a neutral Lewis base, solvent or monomer. More specifically, the WCA anion functions as a stabilizing anion to the cation complex and does not form a covalent bond with the metal atom, M. The WCA anion is relatively inert in that it is non-oxidative, non-reducing, and non-nucleophilic.

In general, the WCA can be selected from borates, phosphates, arsenates, antimonates, aluminates, boratobenzene anions, carborane, halocarborane anions, sulfonamidate and sulfonates.

Broadly speaking, suitable borate anion can be represented by Formula A, phosphate, arsenate and antimonate anions can be represented by Formula B, and aluminate anions can be represented by Formula C:

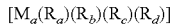

A

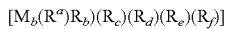

B

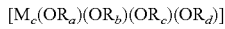

C

Wherein in Formula A, $M_a$ is boron, in Formula B $M_b$ is phosphorus, arsenic or antimony, in Formula C, $M_c$ is aluminum. $R_a$, $R_b$, $R_c$, $R_d$, $R_e$ and $R_f$ independently represent fluorine, linear and branched $C_1$-$C_{10}$ alkyl, linear and branched $C_1$-$C_{10}$ alkoxy, linear and branched $C_3$-$C_5$ haloalkenyl, linear and branched $C_3$-$C_{12}$ trialkylsiloxy, $C_{18}$-$C_{36}$ triarylsiloxy, substituted and unsubstituted $C_6$-$C_{30}$ aryl, and substituted and unsubstituted $C_6$-$C_{30}$ aryloxy groups wherein $R_a$ to $R_f$ cannot all simultaneously represent alkoxy or aryloxy groups. When substituted the aryl groups can be monosubstituted or multisubstituted, wherein the substituents are independently selected from linear and branched $C_1$-$C_5$ alkyl, linear and branched $C_1$-$C_5$ haloalkyl, linear and branched $C_1$-$C_5$ alkoxy, linear and branched $C_1$-$C_5$ haloalkoxy, linear and branched $C_1$-$C_{12}$ trialkylsilyl, $C_6$-$C_{18}$ triarylsiloxy, and halogen selected from chlorine, bromine, and fluorine.

Representative borate anions of Formula A include but are not limited to tetrafluoroborate, tetraphenylborate, tetrakis(pentafluorophenyl)borate, tetrakis(3,5-bis(trifluoromethyl)phenyl)borate, tetrakis(2-fluorophenyl)borate, tetrakis(3-fluorophenyl)borate, tetrakis(4-fluorophenyl)borate, tetrakis(3,5-difluorophenyl)borate, tetrakis(2,3,4,5-tetrafluorophenyl)borate, tetrakis(3,4,5,6-tetrafluorophenyl)borate, tetrakis(3,4,5-trifluorophenyl)borate, methyltris(perfluorophenyl)borate, ethyltris(perfluorophenyl)borate, phenyltris(perfluorophenyl)borate, tetrakis(1,2,2-trifluoroethylenyl)borate, tetrakis(4-tri-i-propylsilyltetrafluorophenyl)borate, tetrakis(4-dimethyl-tert-butylsilyltetrafluorophenyl)borate, (triphenylsiloxy)tris(pentafluorophenyl)borate, (octyloxy)tris(pentafluorophenyl)borate, tetrakis[3,5-bis[1-methoxy-2,2,2-trifluoro-1-(trifluoromethyl)ethyl]phenyl]borate, tetrakis[3-[1-methoxy-2,2,2-trifluoro-1-(trifluoromethyl)ethyl]-5-(trifluoromethyl)phenyl]borate, and tetrakis[3-[2,2,2-trifluoro-1-(2,2,2-trifluoroethoxy)-1-(trifluoromethyl)ethyl]-5-(trifluoromethyl)phenyl]borate.

Representative phosphates, arsenates, antimonates of Formula B include but are not limited to hexafluorophosphate, hexaphenylphosphate, hexakis(pentafluorophenyl)phosphate, hexakis(3,5-bis(trifluoromethyl)phenyl)phosphate, hexafluoroarsenate, hexaphenylarsenate, hexakis(pentafluorophenyl)arsenate, hexakis(3,5-bis(trifluoromethyl)phenyl)arsenate, hexafluoroantimonate, hexaphenylantimonate, hexakis(pentafluorophenyl)antimonate, hexakis(3,5-bis(trifluoromethyl)phenyl)antimonate, and the like.

Representative aluminate anions of Formula C include but are not limited to tetrakis(pentafluorophenyl)aluminate, tris(nonafluorobiphenyl)fluoroaluminate, (octyloxy)tris(pentafluorophenyl)aluminate, tetrakis(3,5-bis(trifluoromethyl)phenyl)aluminate, and methyltris(pentafluorophenyl)aluminate.

In an embodiment of this invention suitable $Z^\ominus$ is selected from $B(C_6F_5)_4^\ominus$, $B[C_6H_3(CF_3)_2]_4^\ominus$, $B(C_6H_5)_4^\ominus$, $[Al(OC(CF_3)_2C_6F_5)_4]^\ominus$, $BF_4^\ominus$, $PF_6^\ominus$, $AsF_6^\ominus$, $SbF_6^\ominus$, $(CF_3SO_2)N^\ominus$ and $CF_3SO_3^\ominus$.

In another embodiment of this invention, the compound of Formula (I) is having the following substituents:

is cyclooctene, bicyclo[3,3,0]octene, bicyclo[2,2,1]hept-2-ene, bicyclo[2,2,2]oct-2-ene or tricyclo[5,2,1,0$^{2,6}$]dec-3-ene;

M is palladium;

LB is acetonitrile, tert-butyronitrile, $C_6H_5CN$, 2,4,6-trimethylbenzonitrile, pyridine, 4-methylpyridine, 3,5-dimethylpyridine, 4-methoxypyridine, benzophenone or triphenylphosphine oxide;

$Z^\ominus$ is selected from $B(C_6F_5)_4^\ominus$, $B[C_6H_3(CF_3)_2]_4^\ominus$, $(CF_3SO_2)N^\ominus$, or $CF_3SO_3^\ominus$;

Y is $PR_3$ or $O=PR_3$, where R is independently selected from isopropyl, sec-butyl, tert-butyl, cyclohexyl, phenyl, benzyl, isopropoxy, sec-butoxy, tert-butoxy, cyclohexyloxy, phenoxy or benzyloxy; and $R_1$ is methyl, ethyl, isopropyl, sec-butyl, tert-butyl, phenyl, phenoxy or acetyl ($CH_3CO$).

In another embodiment of this invention, the compound of this invention is represented by formula (II):

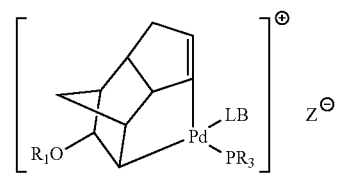

(II)

wherein,

LB is selected from pyridine, acetonitrile or $C_6H_5CN$;

$Z^\ominus$ is selected from $B(C_6F_5)_4^\ominus$, $B(C_6H_5)_4^\ominus$, $BF_4^\ominus$, or $CF_3SO_3^\ominus$;

R is independently selected from methyl, ethyl, ($C_3$-$C_6$) alkyl, substituted or unsubstituted ($C_3$-$C_7$)cycloalkyl, ($C_6$-$C_{10}$)aryl, ($C_6$-$C_{10}$)aralkyl, methoxy, ethoxy, ($C_3$-$C_6$)alkoxy, substituted or unsubstituted ($C_3$-$C_7$)cycloalkoxy, ($C_6$-$C_{10}$) aryloxy or ($C_6$-$C_{10}$)aralkyloxy; and $R_1$ is methyl, ethyl, linear or branched ($C_3$-$C_6$)alkyl, ($C_6$-$C_{10}$)aralkyl or $R_2CO$, where $R_2$ is methyl, ethyl or ($C_3$-$C_6$)alkyl, In a further embodiment of this invention the compound of formula (II) is having the following substituents:

LB is acetonitrile;
Z$^\ominus$ is B(C$_6$F$_5$)$_4$$^\ominus$;
R is n-propyl, isopropyl, tert-butyl or phenyl; and
R$_1$ is n-propyl, isopropyl, tert-butyl or —COCH$_3$.

In another embodiment of this invention the compound of this invention is represented by formula (IIA):

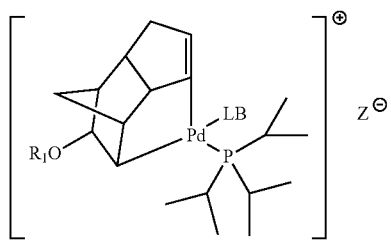

(IIA)

wherein:
LB is acetonitrile or pyridine;
Z$^\ominus$ is selected from B(C$_6$F$_5$)$_4$$^\ominus$ or BF$_4$$^\ominus$; and
R$_1$ is isopropyl or —OCH$_3$.

In this aspect of the embodiment, the compound of formula (IIA) is having the substituents as follows:
LB is either acetonitrile or pyridine; Z$^\ominus$ is B(C$_6$F$_5$)$_4$$^\ominus$ or BF$_4$$^\ominus$; and R$_1$ is isopropyl.

In yet another embodiment of this invention the compound of this invention is represented by formula (IIB):

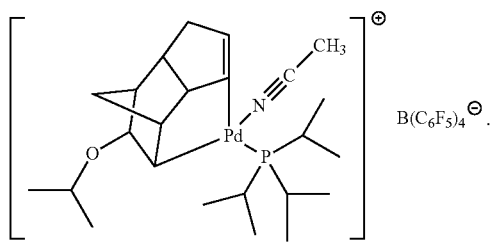

(IIB)

In yet another embodiment of this invention the compound of this invention is represented by formula (IIC):

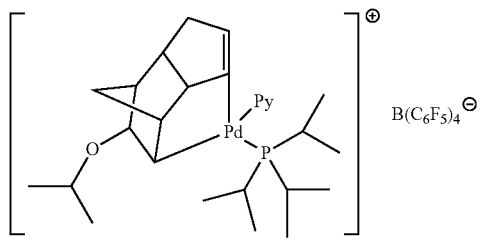

(IIC)

wherein Py is pyridine.

In yet another embodiment of this invention the compound of this invention is represented by formula (IID):

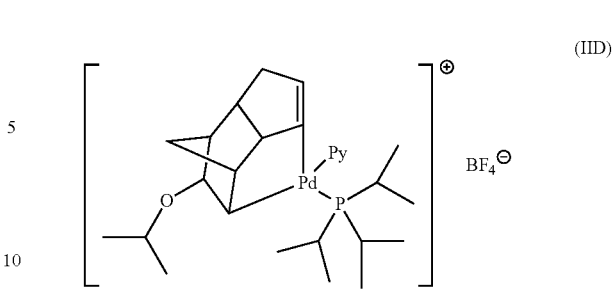

(IID)

wherein Py is pyridine.

In another aspect of this invention there is also provided a compound of formula (III):

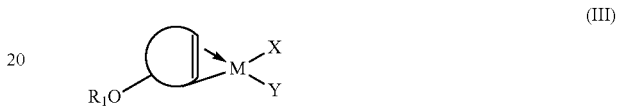

(III)

wherein,

is (C$_5$-C$_{10}$)cycloalkene, (C$_7$-C$_{12}$)bicycloalkene or (C$_8$-C$_{12}$) tricycloalkene group;
M is nickel, palladium or platinum;
X is halogen, triflate, mesylate or tosylate;
Y is PR; or O=PR$_3$, where R is independently selected from methyl, ethyl, (C$_3$-C$_6$)alkyl, substituted or unsubstituted (C$_3$-C$_7$)cycloalkyl, (C$_6$-C$_{10}$)aryl, (C$_6$-C$_{10}$)aralkyl, methoxy, ethoxy, (C$_3$-C$_6$)alkoxy, substituted or unsubstituted (C$_3$-C$_7$)cycloalkoxy, (C$_6$-C$_{10}$)aryloxy or (C$_6$-C$_{10}$)aralkyloxy; and
R$_1$ is methyl, ethyl, linear or branched (C$_3$-C$_6$)alkyl, (C$_6$-C$_{10}$)aryl, (C$_6$-C$_{10}$)aralkyl or R$_2$CO, where R$_2$ is methyl, ethyl or (C$_3$-C$_6$)alkyl; and
with the proviso that when R is phenyl R$_1$ is not methyl.

It should be noted that a few of the compounds of formula (III) are known. More specifically, a compound of formula (III) where

is a dicyclopentadienyl or cyclooctenyl group and where R$_1$ is methoxy, M is palladium, X is chlorine or bromine and Y is triphenyl phosphine is disclosed by Crociani et al., S. Chem. Soc. A (1968) 2869. Accordingly, the following compounds are excluded from the compound of formula (III):
[Pd(C$_8$H$_{12}$.OCH$_3$)(P(C$_6$H$_5$)$_3$)Cl];
[Pd(C$_8$H$_{12}$.OCH$_3$)(P(C$_6$H$_5$)$_3$)Br];
[Pd(C$_{10}$H$_{12}$.OCH$_3$)(P(C$_6$H$_5$)$_3$)Cl];
[Pd(C$_{10}$H$_{12}$.OCH$_3$)(P(C$_6$H$_5$)$_3$)Br];
[Pt(C$_8$H$_{12}$.OCH$_3$)(P(C$_6$H$_5$)$_3$)Cl];
[Pt(C$_8$H$_{12}$.OCH$_3$)(P(C$_6$H$_5$)$_3$)Br];
[Pt(C$_{10}$H$_{12}$.OCH$_3$)(P(C$_6$H$_5$)$_3$)Cl]; and
[Pt(C$_{10}$H$_{12}$.OCH$_3$)(P(C$_6$H$_5$)$_3$)Br].

In one of the embodiments of this invention, the compound of formula (III) is having the following substituents:

is cyclooctene, bicyclo[3,3,0]octene, bicyclo[2,2,1]hept-2-ene, bicyclo[2,2,2]oct-2-ene or tricyclo[5,2,1,0$^{2,6}$]dec-3-ene, the latter is commonly known as dicyclopentadiene;

M is palladium;

X is chlorine or triflate;

Y is $PR_3$ or $O=PR_3$, where R is independently selected from isopropyl, sec-butyl, tert-butyl, cyclohexyl, phenyl, benzyl, isopropoxy, sec-butoxy, tert-butoxy, cyclohexyloxy, phenoxy or benzyloxy; and $R_1$ is methyl, ethyl, n-propyl, isopropyl, sec-butyl, tert-butyl, phenyl or acetyl.

In another embodiment of this invention, the compound of this aspect of the invention, is represented by formula (IIIA):

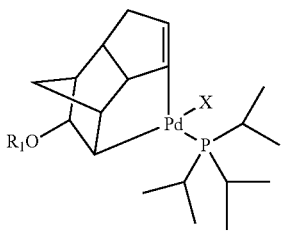

(IIIA)

wherein:

X is chlorine or triflate; and $R_1$ is n-propyl, isopropyl or —$COCH_3$.

In further embodiments of this invention the compound of formula (III) encompasses where $R_1$ is isopropyl; or where $R_1$ is n-propyl; or where $R_1$ is —$COCH_3$.

Non-limiting exemplary compounds of formula (III), can be represented by formulae (IIIB), (IIIC) or (IIID):

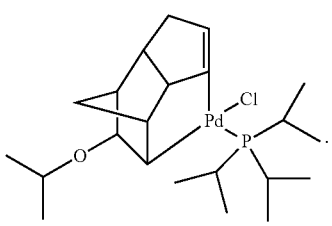

(IIIB)

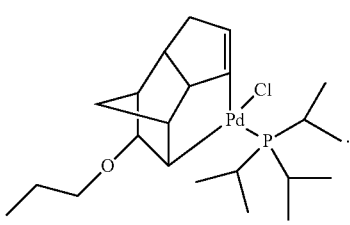

(IIIC)

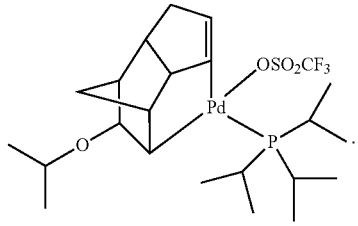

(IIID)

In another embodiment of this invention, other representative compounds that are encompassed by compounds of formula (III) can be represented by formula (IIIE):

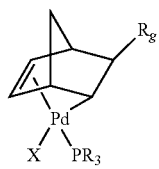

(IIIE)

Where R and X are as defined above. $R_g$ is selected from acetoxy, methoxy, ethoxy, phenoxy and substituted or unsubstituted phenyl. Where substituents include any of the moieties known to one skilled in the art. Non-limiting examples of suitable substituents include ($C_1$-$C_6$)alkyl, ($C_1$-$C_6$)alkoxy, ($C_7$-$C_{10}$)aralkyl, ($C_6$-$C_{10}$)aralkyloxy, ($C_6$-$C_{10}$) aryl, ($C_6$-$C_{10}$)aralkyloxy, and the like. In another embodiment, a compound of formula (IIIE) includes compounds, where X is Cl, Br or I; R is independently isopropyl, tert-butyl or phenyl; and $R_g$ is acetoxy, methoxy or phenyl. In another embodiment, a compound of formula (IIIE) includes compounds, where X is Cl, Br or I; R is independently isopropyl, tert-butyl or phenyl; and $R_g$ is methoxyphenyl.

In a further aspect of this invention there are also provided a series of compounds which are useful as procatalysts of the formula (IIIX) or (IIIY):

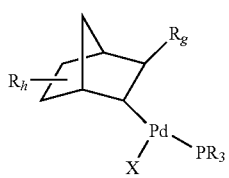

(IIIX)

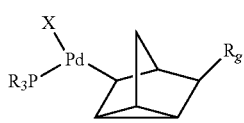

(IIIY)

Where R, $R_g$ and X are as defined above. $R_h$ is a suitable functional group which aids in the chain propagation by inserting into the olefin which is undergoing polymerization. Examples of such groups include hydroxy, alkenyl group such as vinyl, and the like.

The compounds of this invention can be synthesized by any of the procedures known to one skilled in the art. Specifically, as noted above, a few of the compounds of formula (III), and several of the starting materials used in the preparation of the compounds of this invention are known or are themselves commercially available. The compounds of this invention and several of the precursor compounds may also be prepared by methods used to prepare similar compounds as reported in the literature and as further described herein. See for example, J. Chatt, et al., J. Chem. Soc. (1957) 3413-3416; M. Green, et al., J. Chem. Soc. (A) (1967) 2054-2057; K. Hiraki, et al., Bull. Chem. Soc. Japan, 53, 1980, 1976-1981; pertinent portions of all of which are incorporated herein by reference.

More specifically, the compounds disclosed herein can be synthesized according to the following procedures of Schemes 1-2, wherein the R, $R_1$, LB, M, X and Y are as defined for Formula I and respectively unless otherwise indicated.

carried out in a suitable solvent at or above room temperature to obtain compound of formula (IIC). Finally, in Scheme 2, step 3, the compound of (IIC) is further reacted with a suitable salt of a weakly coordinating anion, for example, a lithium salt, LiZ, to form the compound of formula (II). Typically, such reactions are carried out at room temperature in a suitable solvent. It should be noted that all of these reaction steps are carried out in an inert atmosphere such as for example nitrogen, helium or argon. Any of the solvents can be used in these reactions including but not limited to alcohols, for example, methanol, ethanol, n-propanol, iso-propanol, n-butanol, iso-butanol, tert-butanol, and the like; alkane solvents, such as, hexane, heptane or petroleum ether; and combinations thereof.

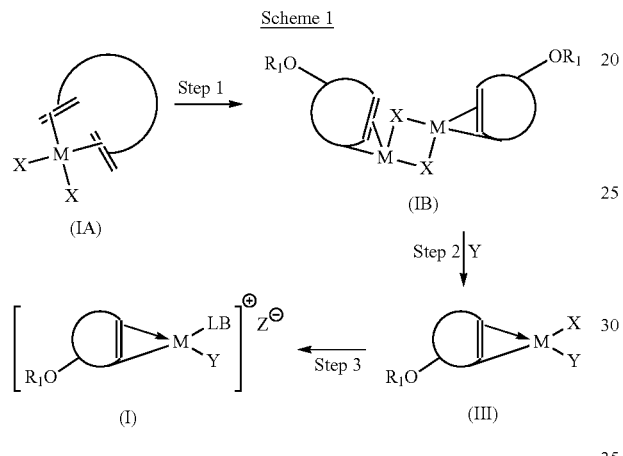

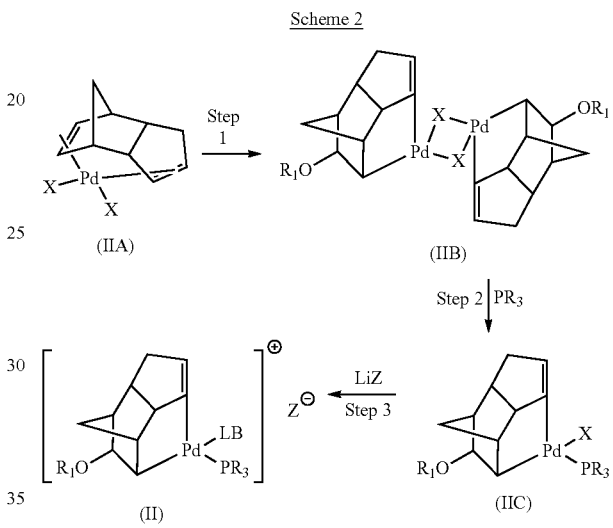

In Scheme I, step 1, a suitable cyclodiene complexed metal compound of formula (IA) is reacted with an appropriate alcohol or an acid to form a compound of formula (IB). This reaction can be carried out by any of the procedures known in the art. For example, a solution of compound of formula (IA) can be reacted with a suitable alcohol or an acid at room temperature or at a higher temperature to form compound of formula (IB), In step 2, Scheme 1, the compound of formula (IB) is further reacted with a suitable phosphine or a phosphine oxide to form compound of formula (III). This reaction can again be carried out using any of the known literature procedures. Typically, such reactions are carried out in a suitable solvent at or above room temperature. Finally, in step 3, Scheme I, the compound of formula (III) is reacted with a suitable salt of a weakly coordinating anion of formula A-Z to form compound of formula (I), where A is any suitable cation, such as for example alkali metal cation or the like which readily exchanges the anion, Z with X of compound of formula (III).

Scheme 2 illustrates synthesis of some of the specific compounds as enumerated herein. Specifically, the compounds of formula (II) and their precursor, the compounds of formula (IIC) can be synthesized from dicyclopentadiene complexes/Pd(II) salts of formula (IIA). As illustrated in Scheme 2, step 1, the compounds of formula (IIA) can be reacted with a variety of alcohols or carboxylic acids (i.e., $R_1OH$, where $R_1$ is alkyl, aryl or acetyl as defined herein) in a suitable solvent at room temperature or at elevated temperatures to obtain compounds of formula (IIB). In Scheme 2, step 2, the compound of formula (IIB) is reacted with a suitable phosphine or a phosphite of formula $PR_3$ to obtain a compound of formula (IIC). This reaction can again be As described herein, the compounds of this invention, particularly, the compounds of formula (I), and more particularly the compounds of formula (II) are highly effective as single component vinyl addition polymerization catalysts as further described in detail hereinbelow and illustrated by specific examples hereafter. Similarly, the compounds of formula (III) and more particularly compounds of formula (IIG), and even more particularly compounds of formulae (IIIA) to (IIIE), (IIIX) and (IIIY) are effective as bicomponent catalysts for the vinyl addition polymerization of a variety of olefins as further described in detail hereinbelow and illustrated by specific examples hereafter.

Polymers

The compounds of this invention can be used as vinyl addition polymerization initiators for preparing a variety of cyclic olefin addition polymers. In one aspect of this invention by employing a compound of this invention of the formula (I) or (II) as an unicomponent system, the compound is regarded as an initiator where the initiating group, for example Pd—C bond, replicates as closely as possible the character of the propagation specie. Therefore, the polydispersity is likely to be reduced and the number of active centers increased in both solution and mass polymerization. In contrast, a few of the heretofore known compounds, such as for example, the Pd-allyl complex needs to switch from a sigma-pi to sigma bonding configuration and then the catalyst center has to generate an inserted cycloalkyl structural unit, for example, norbornyl structural unit if norbornene is the cyclo olefinic monomer employed. Thus, the compounds of this invention provide hitherto unobtainable benefits as initiators for preparing certain of the cyclo-olefinic polymers as described herein.

In another aspect of this invention, the compounds of formula (III) are admixed in-situ with certain of the compounds of formula (VI) to form very active bicomponent catalyst systems which are further activated either by the solvent or the monomer. It has now surprisingly been found that such catalyst systems are very useful for preparing a variety of polymers from certain of the cyclo olefinic monomers as described herein and avoid extraneous ligands, such as acetonitrile.

Accordingly, there is provided a polymerization composition comprising:

a compound of the formula (I):

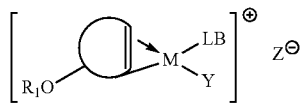

(I)

wherein,

is $(C_5-C_{10})$cycloalkene, $(C_7-C_{12})$bicycloalkene or $(C_8-C_{12})$ tricycloalkene group;

M is nickel, palladium or platinum;

LB is a Lewis Base;

$Z^{\ominus}$ is a weakly coordinating anion;

Y is $PR_3$ or $O=PR_3$, where R is independently selected from methyl, ethyl, $(C_3-C_6)$alkyl, substituted or unsubstituted $(C_3-C_7)$cycloalkyl, $(C_6-C_{10})$aryl, $(C_6-C_{10})$aralkyl, methoxy, ethoxy, $(C_3-C_6)$alkoxy, substituted or unsubstituted $(C_3-C_7)$cycloalkoxy, $(C_6-C_{10})$aryloxy or $(C_6-C_{10})$ aralkyloxy; and $R_1$ is methyl, ethyl, linear or branched $(C_3-C_6)$alkyl, $(C_6-C_{10})$aryl, $(C_6-C_{10})$aralkyl or $R_2CO$, where $R_2$ is methyl, ethyl or $(C_3-C_6)$alkyl; and a monomer of formula (IV):

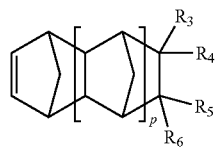

(IV)

wherein:

p is an integer 0, 1 or 2;

$R_3$, $R_4$, $R_5$ and $R_6$ are the same or different and each independently of one another is selected from hydrogen, linear or branched $(C_1-C_{16})$alkyl, hydroxy$(C_1-C_{16})$alkyl, perfluoro$(C_1-C_{12})$alkyl, $(C_3-C_{12})$cycloalkyl, $(C_6-C_{12})$bicycloalkyl, $(C_7-C_{14})$tricycloalkyl, $(C_6-C_{10})$aryl, $(C_6-C_{10})$aryl $(C_1-C_3)$alkyl, perfluoro$(C_6-C_{10})$aryl, perfluoro$(C_6-C_{10})$aryl $(C_1-C_3)$alkyl, di$(C_1-C_2)$alkylmaleimide$(C_3-C_6)$alkyl, di$(C_1-C_2)$alkylmaleimide$(C_2-C_6)$alkoxy$(C_1-C_2)$alkyl, hydroxy, $(C_1-C_{12})$alkoxy, $(C_3-C_{12})$cycloalkoxy, $(C_6-C_{12})$bicycloalkoxy, $(C_7-C_{14})$tricycloalkoxy, $(C_6-C_{10})$aryloxy$(C_1-C_3)$ alkyl, $(C_5-C_{10})$heteroaryloxy$(C_1-C_3)$alkyl, $(C_6-C_{10})$aryloxy, $(C_5-C_{10})$heteroaryloxy or $(C_1-C_6)$acyloxy, where each of the aforementioned substituents are optionally substituted with a group selected from halogen or hydroxy.

It should be noted that in this aspect of the invention, all of the compounds of formula (I) including all of the compounds of formula (II) as described herein can be employed without any limitation. It should further be noted that any of the known monomers of formula (IV) can be employed in this aspect of the invention. Representative examples of monomers of formula (IV) include the following without any limitations:

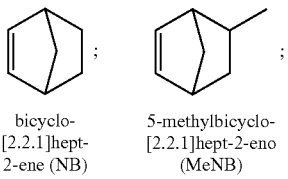

bicyclo-[2.2.1]hept-2-ene (NB)

5-methylbicyclo-[2.2.1]hept-2-eno (MeNB)

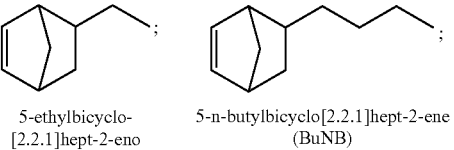

5-ethylbicyclo-[2.2.1]hept-2-eno (EtNB)

5-n-butylbicyclo[2.2.1]hept-2-ene (BuNB)

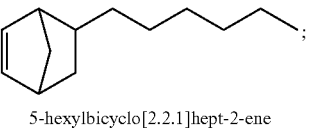

5-hexylbicyclo[2.2.1]hept-2-ene (HexNB)

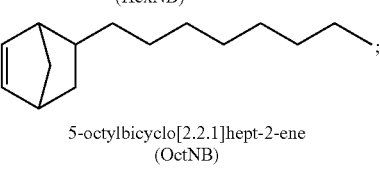

5-octylbicyclo[2.2.1]hept-2-ene (OctNB)

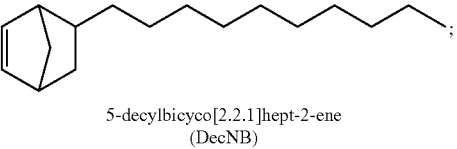

5-decylbicyco[2.2.1]hept-2-ene (DecNB)

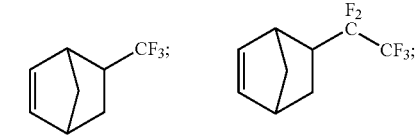

5-trifluoromethylbicyclo-[2.2.1]hept-2-ene (CF3NB)

5-perfluoroethylbicyclo-[2.2.1]hept-2-ene (C2F5NB)

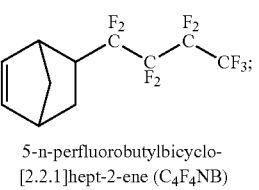

5-n-perfluorobutylbicyclo-[2.2.1]hept-2-ene (C4F4NB)

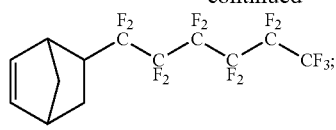

5-perfluorohexylbicyclo[2.2.1]hept-2-2-ene (C₆C₁₃NB)

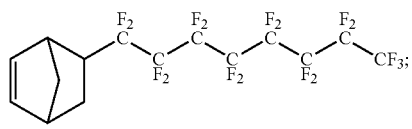

5-perfluorooctylbicyclo[2.2.1]hept-2-ene (OctNB)

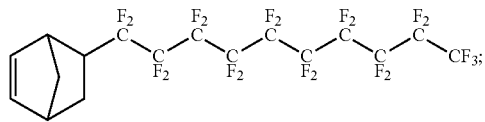

5-perfluorodecylbicyclo[2.2.1]hept-2-ene (PerfluoroDecNB)

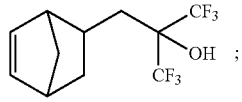

norbornenyl-2-trifluoromethyl-3,3,3-trifluoropropan-2-ol (HFANB)

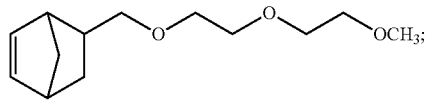

5-((2-(2-methoxyethoxy)ethoxy)methyl)-bicyclo[2.2.1]hept-2-ene (NBTON)

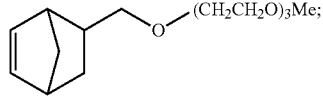

1-(bicyclo[2.2.1]hept-5-en-2-yl)-2,5,8,11-tetraoxadodecane (NBTODD)

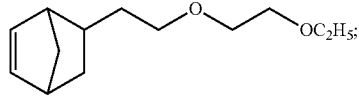

5-(2-(2-ethoxyethoxy)ethyl)bicyclo-[2.2.1]hept-2-ene

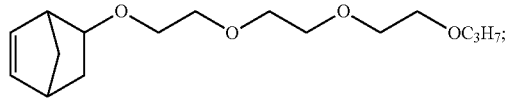

5-(2-(2-(2-propoxyethoxy)ethoxy)ethoxy)bicyclo[2.2.1]-hept-2-ene

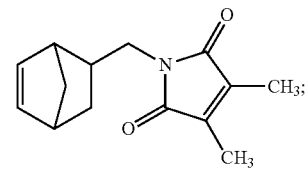

1-(bicyclo[2.2.1]hept-5-en-2-ylmethyl)-3,4-dimethyl-1H-pyrrole-2,5-dione (MeDMMINB)

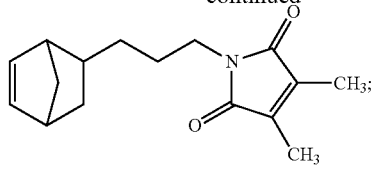

1-(3-(bicyclo[2.2.1]hept-5-en-2-yl)propyl)-3,4-dimethyl-1H-pyrrole-2,5-dione (PrDMMINB)

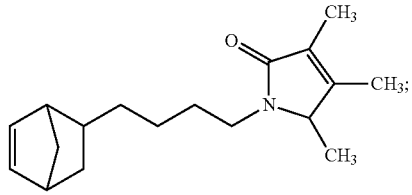

1-(4-(bicyclo[2.2.1]hept-5-en-2-yl)butyl)-3,4-dimethyl-1H-pyrrole-2,5-dione (BuDMMINB)

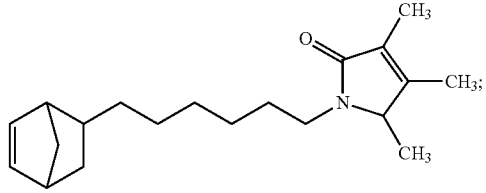

1-(6-(bicyclo[2.2.1]hept-5-en-2-yl)hexyl)-3,4-dimethyl-1H-pyrrole-2,5-dione (HexDMMINB)

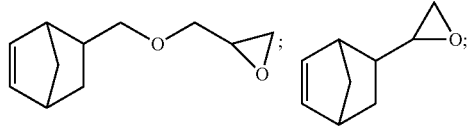

2-((bicyclo[2.2.1]hept-5-en-2-ylmethoxy)methyl)oxirane (MGENB)

2-(bicyclo[2.2.1]hept-5-en-2-yl)oxirane

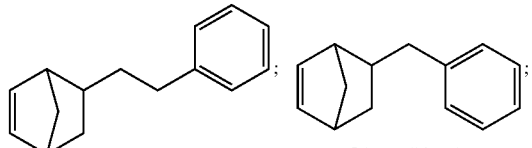

2-(7-(bicyclo[2.2.1]hept-5-en-2-yl)heptyl)oxirane

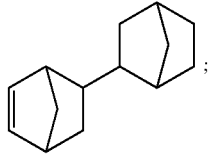

5-phenethylbicyclo[2.2.1]hept-2-ene (PENB)

5-benzylbicyclo[2.2.1]hept-2-ene (BnNB)

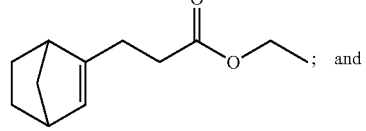

2-(bicyclo[2.2.1]hept-5-en-2-yl)bicyclo[2.2.1]heptane (also referred to herein as NBANB)

ethyl 3-(bicyclo[2.2.1]hept-2-en-2-yl)propanoate (EPEsNB)

and

-continued

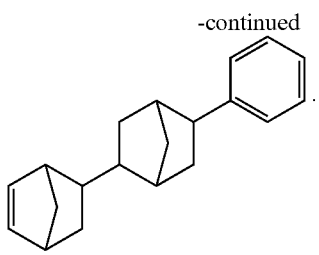

2-(bicyclo[2.2.1]hept-5-en-2-yl)-5-phenyl-bicyclo[2.2.1]heptane
(also referred to herin as NBNBAPh)

In one of the embodiments the polymerizable composition of this invention encompasses a compound of formula (I), which is selected from the group consisting of:

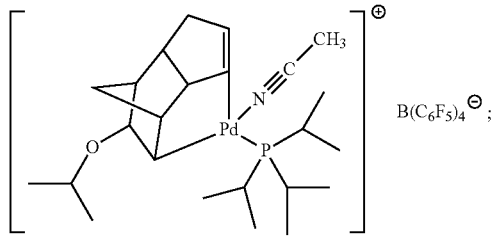
(IIB)

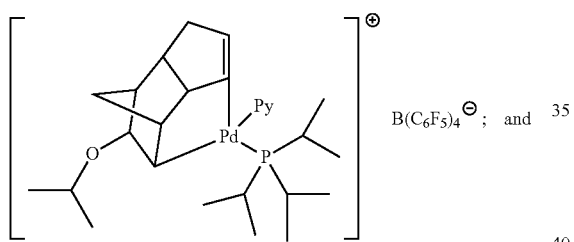
(IIC)

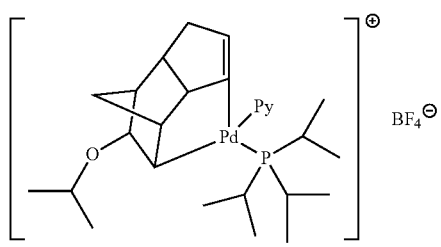
(IID)

wherein Py is pyridine; and said polymerizable monomer is selected from the group consisting of:
bicyclo[2.2.1]hept-2-ene (NB);
norbornenyl-2-trifluoromethyl-3,3,3-trifluoropropan-2-ol (HFANB);
5-hexylbicyclo-[2.2.1]hept-2-ene (HexNB);
5-ortylbicyclo[2.2.1]hept-2-ene (OctNB);
5-decylbicyclo[2.2.1]hept-2-ene (DecNB);
5-perfluorobutylbicyclo[2.2.1]hept-2-ene ($C_4F_9$NB);
1-(3-(bicyclo[2,2,1]hept-5-en-2-yl)propyl)-3,4-dimethyl-1H-pyrrole-2,5-dione (PrDMMINB);
1-(4-(bicyclo[2.2.1]hept-5-en-2-yl)butyl)-3,4-dimethyl-1H-pyrrole-2,5-dione (BuDMMINB);
1-(6-(bicyclo[2.2.1]hept-5-en-2-yl)hexyl)-3,4-dimethyl-1H-pyrrole-2,5-dione (HexDMMINB);
5-phenethylbicyclo[2.2.1]hept-2-ene (PENB);
5-benzylbicyclo[2.2.1]hept-2-ene (BnNB); and
2-(bicyclo[2.2.1]hept-5-en-2-yl)bicyclo[2.2.1]heptane (NBANB).

In a further aspect of this invention there is also provided a polymerization composition comprising:
a compound of the formula (III):

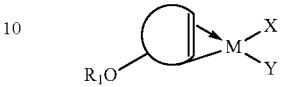
(III)

wherein,

is ($C_5$-$C_{10}$)cycloalkene, ($C_7$-$C_{12}$)bicycloalkene or ($C_8$-$C_{12}$)tricycloalkene group;
M is nickel, palladium or platinum;
X is halogen, triflate, mesylate or tosylate;
Y is $PR_3$ or $O=PR_3$, where R is independently selected from methyl, ethyl, ($C_3$-$C_6$)alkyl, substituted or unsubstituted ($C_3$-$C_7$)cycloalkyl, ($C_6$-$C_{10}$)aryl, ($C_6$-$C_{10}$)aralkyl, methoxy, ethoxy, ($C_3$-$C_6$)alkoxy, substituted or unsubstituted ($C_3$-$C_7$)cycloalkoxy, ($C_6$-$C_{10}$)aryloxy or ($C_6$-$C_{10}$)aralkyloxy; and
$R_1$ is methyl, ethyl, linear or branched ($C_3$-$C_6$)alkyl, ($C_6$-$C_{10}$)aryl, ($C_6$-$C_{10}$)aralkyl or $R_2CO$, where $R_2$ is methyl, ethyl or ($C_3$-$C_6$)alkyl;
a compound of the formula (V):
$M_d^{\oplus}Z^{\ominus}$;

wherein
$M_d^{\oplus}$ is a cation selected from lithium, sodium, potassium, cesium, barium, ammonium or linear or branched tetra($C_1$-$C_4$)alkyl ammonium;
$Z^{\ominus}$ is a weakly coordinating anion selected from $B(C_6F_5)_4^{\ominus}$, $B[C_6H_3(CF_3)_2]_4^{\ominus}$, $E(C_6H_5)_4^{\ominus}$, [Al(OC(CF_3)_2C_6F_5)_4]^{\ominus}$, $BF_4^{\ominus}$, $PF_6^{\ominus}$, $AsF_6^{\ominus}$, $SbF_6^{\ominus}$, $(CF_3SO_2)N^{\ominus}$ or $CF_3SO_3^{\ominus}$; and
a monomer of formula (IV):

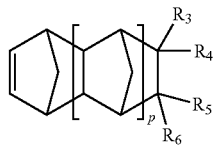
(IV)

wherein:
p is an integer 0, 1 or 2;
$R_3$, $R_4$, $R_5$ and $R_6$ are the same or different and each independently of one another is selected from hydrogen, linear or branched ($C_1$-$C_{16}$)alkyl, hydroxy($C_1$-$C_{16}$)alkyl, perfluoro($C_1$-$C_{12}$)alkyl, ($C_3$-$C_{12}$)cycloalkyl, ($C_6$-$C_{12}$)bicycloalkyl, ($C_7$-$C_{14}$)tricycloalkyl, ($C_6$-$C_{10}$)aryl, ($C_6$-$C_{10}$)aryl($C_1$-$C_3$)alkyl, perfluoro($C_6$-$C_{10}$)aryl, perfluoro($C_6$-$C_{10}$)aryl($C_1$-$C_3$)alkyl, di($C_1$-$C_2$)alkylmaleimide($C_3$-$C_6$)alkyl, di($C_1$-$C_2$)alkylmaleimide($C_2$-$C_6$)alkoxy($C_1$-$C_2$)alkyl, hydroxy, ($C_1$-$C_{12}$)alkoxy, ($C_3$-$C_{12}$)cycloalkoxy, ($C_6$-$C_{12}$)bicycloalkoxy, ($C_7$-$C_{14}$)tricycloalkoxy, ($C_6$-$C_{10}$)aryloxy($C_1$-$C_3$)alkyl, ($C_5$-$C_{10}$)heteroaryloxy($C_1$-$C_3$)alkyl, ($C_6$-$C_{10}$)aryloxy, ($C_5$-$C_{10}$)heteroaryloxy or ($C_1$-$C_6$)acyloxy, where each of the aforementioned substituents are optionally substituted with a group selected from halogen or hydroxy.

In this aspect of the invention the polymerizable composition encompasses a compound of formula (III), which is selected from the group consisting of:

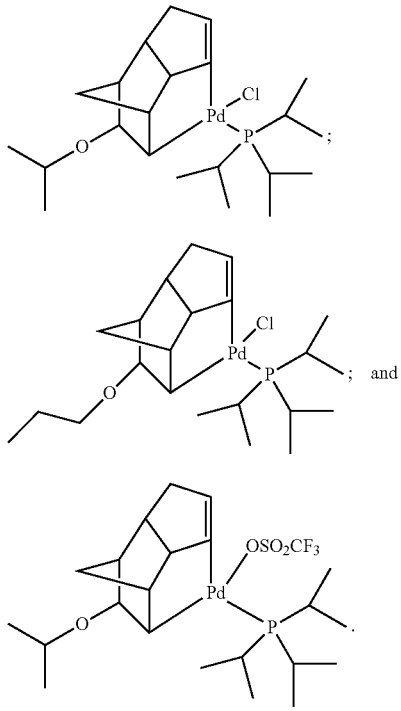

Further the compound of formula (V) is selected from the group consisting of:
lithium tetrafluoroborate;
lithium triflate;
lithium tetrakis(pentafluorophenyl)borate;
lithium (diethyl ether) tetrakis(pentafluorophenyl)borate ([Li(OEt$_2$)$_{2.5}$][B(C$_6$F$_5$)$_4$]) (LiFABA);
lithium tetraphenylborate;
lithium tetrakis(3,5-bis(trifluoromethyl)phenyl)borate;
lithium tetrakis(2-fluorophenyl)borate;
lithium tetrakis(3-fluorophenyl)borate;
lithium tetrakis(4-fluorophenyl)borate;
lithium tetrakis(3,5-difluorophenyl)borate;
lithium hexafluorophosphate;
lithium hexaphenylphosphate;
lithium hexakis(pentafluorophenyl)phosphate;
lithium hexafluoroarsenate;
lithium hexaphenylarsenate;
lithium hexakis(pentafluorophenyl)arsenate;
lithium hexakis(3,5-bis(trifluoromethyl)phenyl)arsenate;
lithium hexafluoroantimonate;
lithium hexaphenylantimonate;
lithium hexakis(pentafluorophenyl)antimonate;
lithium hexakis(3,5-bis(trifluoromethyl)phenyl)antimonate;
lithium tetrakis(pentafluorophenyl)aluminate;
lithium tris(nonafluorobiphenyl)fluoroaluminate;
lithium (octyloxy)tris(pentafluorophenyl)aluminate;
lithium tetrakis(3,5-bis(trifluoromethyl)phenyl)aluminate; and
lithium methyltris(pentafluorophenyl)aluminate.

Again, any of the polymerizable monomer as described herein can be used. For example, the polymerizable monomer is selected from the group consisting of:
bicyclo[2.2.1]hept-2-ene (NB);
norbornenyl-2-trifluoromethyl-3,3,3-trifluoropropan-2-ol (HFANB);
5-hexylbicyclo-[2.2.1]hept-2-ene (HexNB);
5-octylbicyclo[2.2.1]hept-2-ene (OctNB);
5-decylbicyclo[2.2.1]hept-2-ene (DecNB);
5-perfluorobutylbicyclo[2.2.1]hept-2-ene (C$_4$F$_9$NB);
1-(3-(bicyclo[2.2.1]hept-5-en-2-yl)propyl)-3,4-dimethyl-1H-pyrrole-2,5-dione (PrDMMINB);
1-(4-(bicyclo[2.2.1]hept-5-en-2-yl)butyl)-3,4-dimethyl-1H-pyrrole-2,5-dione (BuDMMINB);
1-(6-(bicyclo[2.2.1]hept-5-en-2-yl)hexyl)-3,4-dimethyl-1H-pyrrole-2,5-dione (HexDMMINB);
5-phenethylbicyclo[2.2.1]hept-2-ene (PENB);
5-benzylbicyclo[2.2.1]hept-2-ene (BnNB); and
2-(bicyclo[2.2.1]hept-5-en-2-yl)bicyclo[2.2.1]heptane (NBANB).

As noted, the polymerization reactions can be carried out either neat (mass polymerization) or in solution. That is, by practice of the instant invention it is now possible to make a variety of polymers containing at least one functionalized norbornene monomer (i.e., a compound of formula (IV)) in the presence of either an unicomponent (i.e., a compound of formula (I) or (II)) catalyst or a bicomponent catalyst (i.e., a compound of formula (III) in combination with a compound of formula (V)) as described herein. When bicomponent catalysts are employed the compounds of formula (III) can generally be called as procatalysts and compounds of formula (V) are generally called as activators. However, various other compounds that would effectively function as catalysts, procatalysts and/or activators can also be used in combination with compounds of formulae (III) and (V) when bicomponent catalysts are employed.

It has also been found that the compounds of this invention either as unicomponent or bicomponent catalytic compositions are highly active. Thus it is now possible to make polymers of high quality by employing small amounts of the catalysts. Accordingly, in one of the embodiments the addition polymerization can effectively be carried out using monomer to unicomponent catalyst molar ratio of at least 100:1 based on the total moles of monomers and the catalyst employed. That is, 100 moles of monomer to one mole of the unicomponent catalyst is employed. In other embodiments the molar ratio of monomer:catalyst can be 1,000,000:1; 500,000:1; 100,000:1; 20,000:1; 10,000:1, 1,000:1, 500:1, 400:1, 200:1, and the like. When bicomponent catalyst systems are employed the molar ratio of monomer:procatalyst:activator can be at least 100:1:1. In other embodiments the molar ratio of monomer:procatalyst:activator can be 1,000,000:1:1; 500,000:1:1; 100,000:1:1; 20,000:1:1; 10,000:1:1, 1,000:1:1, 500:1:1, 400:1:1, 200:1:1, and the like. In some embodiments the activator is used in excess of the mole quantities of the procatalyst used, such as for example, molar ratios of procatalyst:activator can be from 1:1 to 1:6.

As noted, the mass polymerization reaction can be carried out with catalyst and monomer without any solvent. Advantageously, such polymerization reactions can also be carried out in a mold at a suitable temperature to form three dimensional polymeric products. In general, the reaction temperatures can range from sub-ambient temperature, such as for example below 0° C. to boiling point of the monomers, however, it is recommended that the components of the reaction vessel or the mold is not heated beyond the flash points of one or more of the monomers. Generally, the mass polymerization is carried out at a temperature range from about 10° C. to 300° C., in some other embodiments the temperature range can be from about 10° C. to 200° C.; or from about 20° C. to 100° C.

Since the polymerization reaction is exothermic, the temperature in the mold during the course of the polymerization is usually higher than the temperature of the feed, unless a chilled mold is employed. Accordingly, the initial mold temperature can generally be within the range of about −20° C. to about 300° C.; or from about 0° C. to about 200° C.; or from 20° C. and 100° C. Temperature distribution in the mold is affected by such factors as mold geometry, characteristics of the mold as a heat sink or heat supplying means, reactivity of catalyst and monomer, and the like. To some extent, the selection of suitable temperatures and heat exchange conditions will have to be based on experience with a given system of mold, feed and catalyst.

After the polymerization reaction is complete, the molded object may be subjected to an additional post cure treatment at a temperature in the range of about 100° C. to 300° C. for about 15 minutes to 24 hours; or 1 to 2 hours. Such a post cure treatment can enhance polymeric properties including glass transition temperature ($T_g$) and heat distortion temperature (HDT). In addition, post curing is desirable hut not essential, to bring the samples to their final stable dimensional states, to minimize residual odors, and to improve final physical properties.

The vinyl addition polymerization can also be carried out in solution employing either unicomponent catalyst (i.e., a compound of formula (I) or (II)) or a bicomponent catalyst (i.e., a compound of formula (III) in combination with a compound of formula (V)) as described herein. In this embodiment the solution of the catalyst is suitably mixed with a desirable solution of one or more of the monomers (i.e., a compound of formula (IV)) under conditions known in the art to form the polymers of this invention. Suitable polymerization solvents include without any limitation alkane and cycloalkane solvents, such as pentane, hexane, heptane, and cyclohexane; halogenated alkane solvents such as dichloromethane, chloroform, carbon tetrachloride, ethylchloride, 1,1-dichloroethane, 1,2-dichloroethane, 1-chloropropane, 2-chloropropane, 1-chlorobutane, 2-chlorobutane, 1-chloro-2-methylpropane, and 1-chloropentane; ethers such as THF and diethylether; aromatic solvents such as benzene, xylene, toluene, mesitylene, chlorobenzene, and o-dichlorobenzene; and halocarbon solvents such as Freon® 112; and mixtures in any combination thereof.

The solution polymerization temperatures can range from sub-ambient temperature, such as for example, below 0° C. to boiling point of the solvents employed. Generally, the solution polymerization is carried out at a temperature range from about 10° C. to 200° C., in some other embodiments the temperature range can be from about 10° C. to 150° C.; or from about 20° C. to 100° C.

The polymers formed according to this invention generally exhibit a number average molecular weight ($M_n$) of at least about 3,000. In another embodiment, the polymer of this invention has a $M_n$, of at least about 5,000. In another embodiment, the polymer of this invention has a $M_n$ of at least about 10,000. In another embodiment, the polymer of this invention has a $M_n$ of at least about 20,000. In yet another embodiment, the polymer of this invention has a $M_n$ of at least about 50,000. In some other embodiments, the polymer of this invention has a $M_n$ of at least about 100,000. In another embodiment, the polymer of this invention has a $M_n$ of higher than 100,000 and can be higher than 500,000 in some other embodiments. The number average molecular weight ($M_n$) of the polymers can be determined by any of the known techniques, such as for example, by gel permeation chromatography (GPC) equipped with suitable detector and calibration standards, such as differential refractive index detector calibrated with narrow-distribution polystyrene standards. As noted, the polymers of this invention typically exhibit very low polydispersity index (PDI), which is a ratio of weight average molecular weight ($M_w$) to number average molecular weight ($M_n$). In general, the PDI of the polymers of this invention is less than 2. In some embodiments the PDI is less than 1.5, less than 1.4, less than 1.3, less than 1.2 or less than 1.1. However, it should be noted that in some embodiments the PDI can be higher than 2, such as for example, higher than 3.

Block Copolymers

Advantageously, it has also now been found that various compounds of formulae (I), (II) or (III) function effectively as catalysts for the formation of a series of block copolymers encompassing one or more norbornene type compounds of formula (IV) as described herein. The block copolymers as described herein can also be prepared by any of the other catalysts known in the art. It has further been found that the block copolymers of this invention provide unique advantages and therefore find utility in a variety of applications including but not limited to forming membrane materials and in various other optical and electronic applications, among others. The membranes formed from the block copolymers are useful for example in separation of organics from biomass or other organic wastes.

Accordingly, there is provided a block copolymer of the formula (VI):

where m and n are integers of at least 15 but in other embodiments m and n can range from 20 to 4000, or from 50 to 3000 or 100 to 2000, and in other embodiments m and n can also be higher than 4000 depending upon the intended use;

b denotes a bond between the two blocks of homopolymers A and B;

A and B are different from each other and independently selected from a repeat unit represented by formula (IVA), said repeat unit is derived from a monomer of formula (IV):

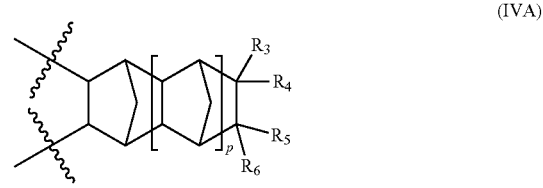

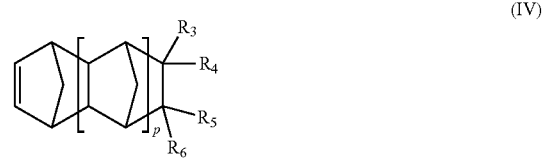

wherein:
〰 denotes a place of bonding with another repeat unit;
p is an integer 0, 1 or 2;

$R_3$, $R_4$, $R_5$ and $R_6$ are the same or different and each independently of one another is selected from hydrogen, linear or branched $(C_1-C_{16})$alkyl, hydroxy$(C_1-C_{16})$alkyl, perfluoro$(C_1-C_{12})$alkyl, $(C_3-C_{12})$cycloalkyl, $(C_6-C_{12})$bicycloalkyl, $(C_7-C_{14})$tricycloalkyl, $(C_6-C_{10})$aryl, $(C_6-C_{10})$aryl $(C_1-C_3)$alkyl, perfluoro$(C_6-C_{10})$aryl, perfluoro$(C_6-C_{10})$aryl $(C_1-C_3)$alkyl, di$(C_1-C_2)$alkylmaleimide$(C_3-C_6)$alkyl, di$(C_1-C_2)$alkylmaleimide$(C_2-C_6)$alkoxy$(C_1-C_2)$alkyl, hydroxy, $(C_1-C_{12})$alkoxy, $(C_3-C_{12})$cycloalkoxy, $(C_6-C_{12})$bicycloalkoxy, $(C_7-C_{14})$tricycloalkoxy, $(C_6-C_{10})$aryloxy$(C_1-C_3)$ alkyl, $(C_5-C_{10})$heteroaryloxy$(C_1-C_3)$alkyl, $(C_6-C_{10})$aryloxy, $(C_5-C_{10})$heteroaryloxy or $(C_1-C_6)$acyloxy, where each of the aforementioned substituents are optionally substituted with a group selected from halogen or hydroxy.

In one of the embodiments of this invention, the block polymer of this invention further encompasses a third type of repeat unit and represented by formula (VII):

$$(A)_m\text{-}b\text{-}(B)_n\text{-}b\text{-}(C)_o \qquad (VII);$$

where m, n and b are as defined above and o is an integer of at least 15, but in other embodiments o can range from 20 to 4000, or from 50 to 3000 or 100 to 2000, and in other embodiments o can also be higher than 4000 depending upon the intended use of the block polymer. C is same as or different from A or B and independently selected from a repeat unit represented by formula (IVA), said repeat unit is derived from a monomer of formula (IV) as defined herein. That is to say that the block copolymers of this invention can exist as di-blocks or as tri-blocks. However, any number of additional blocks can be formed by adding one or more other monomers of formula (IV) sequentially to form mu)ti-block copolymers of this invention. For example, the di-block polymers are typically formed by first polymerizing the first monomer of formula (IV) in the presence of a suitable catalyst and then a second monomer which is either same as the first monomer or a second distinctive monomer can be added to the same polymerization reaction mixture to form the di-block copolymer. In general, the polymerization is carried out in solution at a suitable polymerization reaction temperature as described hereinabove. That is, any of the solvents as mentioned hereinabove can be employed in the presence of one or more suitable polymerization catalysts to form the diblock copolymers. The reaction temperature is generally at around ambient conditions, that is, at around room temperature. However, super-ambient, that is, temperatures above room temperature from around 25° C. to 150° C. or sub-ambient, that is, below room temperature from around 25° C. to 0° C., or even lower temperatures can be employed. The polymerization can also be carried out neat, i.e., mass polymerization without any solvent. The tri-block polymers are similarly formed by the addition of a third monomer after the second monomer has been polymerized. The multi-block polymers are formed by adding sequentially additional monomers. As noted, the block copolymers can be formed using same monomer or different monomers to form different blocks as needed, and in varying molar ratios of the monomers.

Accordingly, in one of the embodiments, there is provided a diblock copolymer, wherein the block molar ratio of A:B is from 1:1 to 1:4. In another embodiment, the block molar ratio of A:B is from 1:1 to 1:2. In yet another embodiment, the block molar ratio of A:B is 1:1. In yet another embodiment the block polymer is a triblock polymer, wherein the block molar ratio of A:B:C is from 1:1:1 to 1:4:1 to 1:1:4. In a further embodiment, block molar ratio of A:B:C is 1:1:1; and in another embodiment the block molar ratio of A:B:C is 1:2:1. In this regard, the size of the blocks can also be controlled by weight fraction of each of the blocks. That is, in a diblock polymer, A-b-B, the weight fraction of monomer A can range from 0.1 to 1, designated as $W_A$. Various tri-block or other multi-block polymers can similarly be made employing different weight fraction of the respective monomers employed.

In general, any of the monomers encompassed by the formula (IV) can be employed to form the block polymer of this invention. For example, non-limiting examples of the repeat units of A may be derived from a monomer selected from the group consisting of:

5-butylbicyclo[2.2.1]hept-2-ene (BuNB);
5-hexylbicyclo[2.2.1]hept-2-ene (HexNB);
5-octylbicyclo[2.2.1]hept-2-ene (OctNB);
5-perfluoroethylbicyclo[2.2.1]hept-2-ene ($C_2F_5$NB);
5-n-perfluorobutylbicyclo[2.2.1]hept-2-ene ($C_4F_9$NB);
5-perfluorohexylbicyclo[2.2.1]hept-2-ene ($C_6F_3$NB);
norbornenyl-2-trifluoromethyl-3,3,3-trifluoropropan-2-ol (HFANB);
1-(3-(bicyclo[2.2.1]hept-5-en-2-yl)propyl)-3,4-dimethyl-1H-pyrrole-2,5-dione (PrDMMINB);
1-(4-(bicyclo[2.2.1]hept-5-en-2-yl)butyl)-3,4-dimethyl-1H-pyrrole-2,5-dione (BuDMMINB);
1-(6-(bicyclo[2.2.1]hept-5-en-2-yl)hexyl)-3,4-dimethyl-1H-pyrrole-2,5-dione (HexDMMINB);
5-phenethylbicyclo[2.2.1]hept-2-ene (PENB);
5-benzylbicyclo[2.2.1]hept-2-ene (BnNB); and
2-(bicyclo[2.2.1]hept-5-en-2-yl)bicyclo[2.2.1]heptane (NBANB).

In another embodiment, non-limiting examples of the repeat unit B is derived from a monomer selected from the group consisting of:

5-butylbicyclo[2.2.1]hept-2-ene (BuNB);
5-hexylbicyclo[2.2.1]hept-2-ene (HexNB);
5-octylbicyclo[2.2.1]hept-2-ene (OctNB);
5-perfluoroethylbicyclo[2.2.1]hept-2-ene ($C_2F_5$NB);
5-n-perfluorobutylbicyclo[2.2.1]hept-2-ene ($C_1F_9$NB);
5-perfluorohexylbicyclo[2.2.1]hept-2-ene ($C_6F_{13}$NB);
norbornenyl-2-trifluoromethyl-3,3,3-trifluoropropan-2-ol (HFANB);
1-(3-(bicyclo[2.2.1]hept-5-en-2-yl)propyl)-3,4-dimethyl-1H-pyrrole-2,5-dione (PrDMMINB);
1-(4-bicyclo[2.2.1]hept-5-en-2-yl)butyl)-3,4-dimethyl-1H-pyrrole-2,5-dione (BuDMMINB);
1-(6-(bicyclo[2.2.1]hept-5-en-2-yl)hexyl)-3,4-dimethyl-1H-pyrrole-2,5-dione (HexDMMINB);
5-phenethylbicyclo[2.2.1]hept-2-ene (PENB);
5-benzylbicyclo[2.2.1]hept-2-ene (BnNB); and
2-(bicyclo[2.2.1]hept-5-en-2-yl)bicyclo[2.2.1]heptane (NBANB).

Finally, non-limiting examples of the repeat unit C is derived from a monomer selected from the group consisting of:

5-butylbicyclo[2.2.1]hept-2-ene (BuNB);
5-hexylbicyclo[2.2.1]hept-2-ene (HexNB);
5-octylbicyclo[2.2.1]hept-2-ene (OctNB);
5-perfluoroethylbicyclo[2.2.1]hept-2-ene ($C_2F_5$NB);
5-n-perfluorobutylbicyclo[2.2.1]hept-2-ene ($C_4F_9$NB);
5-perfluorohexylbicyclo[2.2.1]hept-2-ene ($C_6F_{13}$NB);
norbornenyl-2-trifluoromethyl-3,3,3-trifluoropropan-2-ol (HFANB);
1-(3-(bicyclo[2.2.1]hept-5-en-2-yl)propyl)-3,4-dimethyl-1H-pyrrole-2,5-dione (PrDMMINB);
1-(4-(bicyclo[2.2.1]hept-5-en-2-yl)butyl)-3,4-dimethyl-1H-pyrrole-2,5-dione (BuDMMINB);
1-(6-(bicyclo[2.2.1]hept-5-en-2-yl)hexyl)-3,4-dimethyl-1H-pyrrole-2,5-dione (HexDMMINB);

5-phenethylbicyclo[2.2.1]hept-2-ene (PENB);
5-benzylbicyclo[2.2.1]hept-2-ene (BnNB); and
2-(bicyclo[2.2.1]hept-5-en-2-yl)bicyclo[2.2.1]heptane (NBANB).

In another embodiment, representative examples of the repeat unit A is derived from a monomer selected from the group consisting of:
5-butylbicyclo[2.2.1]hept-2-ene (BuNB);
5-hexylbicyclo[2.2.1]hept-2-ene (HexNB);
5-n-perfluorobutylbicyclo[2.2.1]hept-2-ene ($C_4F_9NB$);
norbornenyl-2-trifluoromethyl-3,3,3-trifluoropropan-2-ol (HFANB);
1-(4-(bicyclo[2.2.1]hept-5-en-2-yl)butyl)-3,4-dimethyl-1H-pyrrole-2,5-dione (BuDMMINB); and
2-(bicyclo[2.2.1]hept-5-en-2-yl)bicyclo[2.2.1]heptane (NBANB).

In yet another embodiment, representative examples of the repeat unit B is derived from a monomer selected from the group consisting of:
5-butylbicyclo[2.2.1]hept-2-ene (BuNB);
5-hexylbicyclo[2.2.1]hept-2-ene (HexNB);
5-n-perfluorobutylbicyclo[2.2.1]hept-2-ene ($C_4F_9NB$);
norbornenyl-2-trifluoromethyl-3,3,3-trifluoropropan-2-ol (HFANB);
1-(4-(bicyclo[2.2.1]hept-5-en-2-yl)butyl)-3,4-dimethyl-1H-pyrrole-2,5-dione (BuDMMINB); and
2-(bicyclo[2.2.1]hept-5-en-2-yl)bicyclo[2.2.1]heptane (NBANB).

In yet another embodiment, representative examples of the repeat unit C is derived from a monomer selected from the group consisting of:
5-butylbicyclo[2.2.1]hept-2-ene (BuNB);
5-hexylbicyclo[2.2.1]hept-2-ene (HexNB);
5-n-perfluorobutylbicyclo[2.2]hept-2-ene ($C_4F_9NB$);
norbornenyl-2-trifluoromethyl-3,3,3-trifluoropropan-2-ol (HFANB);
1-(4-(bicyclo[2.2.1]hept-5-en-2-yl)butyl)-3,4-dimethyl-1H-pyrrole-2,5-dione (BuDMMINB); and
2-(bicyclo[2.2.1]hept-5-en-2-yl)bicyclo[2.2.1]heptane (NBANB).

Non-limiting examples of the block copolymer of this invention is selected from the group consisting of:
a block copolymer derived from 5-hexylbicyclo[2.2.1]hept-2-ene and norbornenyl-2-trifluoromethyl-3,3,3-trifluoropropan-2-ol (HexNB-b-HFANB);
a block copolymer derived from 5-butylbicyclo[2.2.1]hept-2-ene and norbornenyl-2-trifluoromethyl-3,3,3-trifluoropropan-2-ol (BuNB-b-HFANB);
a block copolymer derived from 5-benzylbicyclo[2.2.1]hept-2-ene and 5-n-perfluorobutylbicyclo[2.2.1]hept-2-ene (BnNB-b-$C_4F_9NB$);
a block copolymer derived from 5-n-perfluorobutylbicyclo[2.2.1]hept-2-ene and 1-(4-(bicyclo[2.2.1]hept-5-en-2-yl)butyl)-3,4-dimethyl-1H-pyrrole-2,5-dione ($C_4F_9NB$-b-BuDMMINB);
a block copolymer of derived from norbornenyl-2-trifluoromethyl-3,3,3-trifluoropropan-2-ol and 2-(bicyclo[2.2.1]hept-5-en-2-yl)bicyclo[2.2.1]heptane (HFANB-b-NBANB); and
a block copolymer of derived from 5-hexylbicyclo[2.2.1]hept-2-ene and 2-(bicyclo[2.2.1]hept-5-en-2-yl)bicyclo[2.2.1]heptane (HexNB-b-NBANB).

In one of the embodiments, the block polymer of this invention is selected from the group consisting of:
a block polymer derived from 5-butylbicyclo[2.2.1]hept-2-ene, norbornenyl-2-trifluoromethyl-3,3,3-trifluoropropan-2-ol and 5-butylbicyclo[2.2.1]hept-2-ene (BUNB-b-HFANB-b-BuNB);
a block copolymer derived from 5-n-butylbicyclo[2.2.1]hept-2-ene, 5-benzylbicyclo[2.2.1]hept-2-ene and 2-(bicyclo[2.2.1]hept-5-en-2-yl)bicyclo[2.2.1]heptane (BuNB-b-BnNB-b-NBANB); and
a block polymer derived from norbornenyl-2-trifluoromethyl-3,3,3-trifluoropropan-2-ol, 5-butylbicyclo[2.2.1]hept-2-ene, and norbornenyl-2-trifluoromethyl-3,3,3-trifluoropropan-2-ol (HFANB-b-BuNB-b-HFANB).

The block polymers of this invention can be prepared by any of the procedures known in the art. In general, the polymerization is carried out in solution and in the presence of a suitable metal catalyst. In some embodiments of this invention it has been advantageously found that a metal catalyst in combination with a suitable compound, which may function as co-catalyst, initiator, or pro-intiator or activator, offers a way to make the block polymers of this invention. However, as noted, any of the other approaches known in the art can also be employed.

Accordingly, there is provided a process for the preparation of a block copolymer of formula (VI) as described herein, which encompasses reacting any one of the first monomer, A of formula (IV), as described herein, with a palladium compound to form the first polymer block. Then, a second monomer, B of formula (IV), which is distinct from the first monomer, A of formula (IV), is added to the polymerization reaction mixture to form the block copolymer containing a diblock copolymer having different molar ratios of monomer repeat units, A and B.

In another embodiment, there is further provided a process for the preparation of triblock polymer, which encompasses reacting a third monomer, C of formula (IV), to form a block polymer of formula $$(A)_m\text{-}b\text{-}(B)_n\text{-}b\text{-}(C)_o \qquad (VII);$$

where m, n, o, b, A, B and C are as defined herein. It should be noted that the monomer repeat unit C can be the same or different from A or B and independently selected from a repeat unit represented by formula (IVA), said repeat unit is derived from a monomer of formula (IV) as defined herein. Again, as noted above, the block polymer of formula (VII) is thus termed as triblock polymer and can have various different molar ratios of the repeat units of formula A, B or C as described hereinabove.

The palladium compounds that can be employed in the process of this invention include all of the compounds of formulae (I), (II) and (III) as described herein.

Advantageously, it has now been found that various other palladium compounds can also be employed in the process of this invention. Such palladium compounds suitable for forming block polymers of this invention are represented by the formula:

$$(\text{Allyl})Pd(P(Q_3))(L_1) \text{ or } (\text{methyl})Pd(P(Q_3))(L_1)$$

wherein Q may be the same or different and is independently selected from isopropyl, tert-butyl, neopentyl and cyclohexyl; and $L_1$ is selected from halogen, trifluoroacetate, and trifluoromethanesulfonate (triflate). Non-limiting examples of such palladium compounds include the following:
allylpalladium(triisopropylphosphine)chloride, [Pd(allyl)(triisopropylphosphine)Cl];
allylpalladium(tri-tert-butylphosphine)chloride, [Pd(allyl)(tri-tert-butylphosphine)Cl];

allylpalladium(diisopropyl-tert-butylphosphine)chloride, [Pd(allyl)(diisopropyl-tert-butylphosphine)Cl];

allylpalladium(isopropyl-ditert-butylphosphine)chloride, [Pd(allyl)(isopropyl-ditert-butylphosphine)Cl];

allylpalladium(ditert-butyl-cyclohexylphosphine)chloride, [Pd(allyl)(ditert-butyl-cyclohexylphosphine)Cl];

allylpalladium(ditert-butyl-neopentylphosphine)chloride, [Pd(allyl)(ditert-butyl-neopentylphosphine)Cl];

(allyl)palladium(tricyclohexylphosphine)triflate, [Pd(allyl)(tricyclohexylphosphine)triflate];

(allyl)palladium(triisopropylphosphine)triflate, [Pd(allyl)(triisopropylphosphine)triflate];

(allyl)palladium(tricyclohexylphosphine)trifluoroacetate, [Pd(allyl)(tricyclohexylphosphine)trifluoroacetate];

(allyl)palladium(triisopropylphosphine)trifluoroacetate, [Pd(allyl)(triisopropylphosphine)trifluoroacetate];

methylpalladium(triisopropylphosphine)chloride, [Pd(methyl)(triisopropylphosphine)Cl];

methylpalladium(tri-tert-butylphosphine)chloride, [Pd(methyl)(tri-tert-butylphosphine)Cl];

methylpalladium(diisopropyl-tert-butylphosphine)choride, [Pd(methyl)(diisopropyl-tert-butylphosphine)Cl];

methylpalladium(isopropyl-ditert-butylphosphine)chloride, [Pd(methyl)(isopropyl-ditert-butylphosphine)Cl];

methylpalladium(ditert-butyl-cyclohexylphosphine)chloride, [Pd(methyl)(ditert-butyl-cyclohexylphosphine)Cl];

methylpalladium(tricyclohexylphosphine)chloride, [Pd(methyl)(tricyclohexylphosphine)Cl], also abbreviated as [(Me-Pd—PCy$_3$)Cl], where Cy is cyclohexyl (C$_6$H$_{11}$);

methylpalladium(dicyclohexyl-tert-butylphosphine)chloride, [Pd(methyl)(dicyclohexyl-tert-butylphosphine)Cl];

methylpalladium(cyclohexyl-di(tert-butyl)phosphine)chloride, [Pd(methyl)(cyclohexyl-di(tert-butyl)phosphine)Cl]; and the like.

Another class of palladium compounds that can also be used for forming the block polymers of this invention can be represented by the formula:

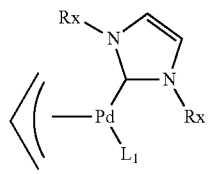

Where Rx is a substituted (C$_8$-C$_{16}$)aryl, for example 2,5-diisopropylbenzene, mesityl and the like, L$_1$ is as defined above. Non-limiting examples of such palladium compounds include the following:

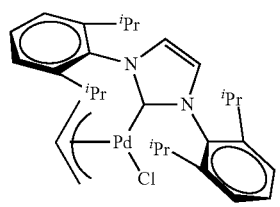

Allyl(palladium)(1,3-bis(2,6-diisopropylphenyl-2,3-dihydro-1H-imidazole)Cl;

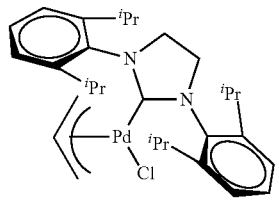

Allyl(palladium)(1,3-bis(2,6-diisopropylphenyl)imidazolidine)Cl, and

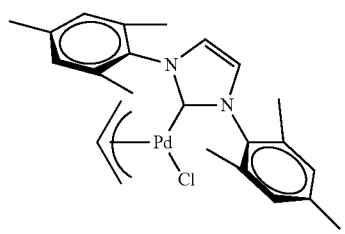

Allyl(palladium)(1,3-dimesityl-2,3-dihydro-1H-imidazole)Cl.

Several of the above noted palladium compounds are either commercially available or known in the literature and can be prepared using any of the procedures known in the literature.

As also noted above, the palladium compounds as mentioned above are generally used in conjunction with an additional compound which functions as a cocatalyst, initiator, pro-initiator or activator. For example, any of the compounds of formula (V) as described hereinabove can be used for this purpose. In one of the embodiments, non-limiting examples of such activator compounds include lithium tetrakis(pentafluorophenyl)borate etherate (Li-FABA-[Li(OEt$_2$)$_{2,5}$][B(C$_6$F$_5$)$_4$]) and N,N-dimethylanilinium tetrakis(pentafluorophenyl)-borate (DANFABA), and the like.

Thus it should be noted that the palladium containing catalysts useful for making the block copolymers of this invention can be prepared as a preformed single component catalyst or prepared in situ by admixing a palladium containing procatalyst with an activator (or a cocatalyst, initiator or pro-initiator, as mentioned above) in the presence of the desired monomer(s) to be polymerized.

Accordingly, the preformed catalyst can be prepared by admixing the catalyst precursors such as a procatalyst and activator (or a cocatalyst, initiator or pro-initiator) in an appropriate solvent, allowing the reaction to proceed under appropriate temperature conditions, and isolating the reaction product, that is, a preformed catalyst product. By procatalyst is meant a palladium containing compound that is converted to an active catalyst by a reaction with a cocatalyst, activator, initiator or a pro-initiator compound. Further description and synthesis of representative procatalysts and activator compounds can be found in U.S. Pat. No. 6,455,650, pertinent portions of which are incorporated herein by reference.

The block copolymers formed according to this invention generally exhibit a number average molecular weight ($M_n$) of at least about 2,000 for each of the blocks formed. The $M_n$ of each of the blocks can be tailored to a desirable property and based on the end use of the block copolymer. Thus, in another embodiment, one of the blocks of the block copolymer of this invention has a $M_n$, of at least about 20,000. In yet another embodiment, one of the blocks of the block copolymer of this invention has a $M_n$, of at least about 50,000. In some other embodiments, one of the blocks of the block copolymer of this invention has a $M_n$ of at least about 100,000. In another embodiment, one block of a diblock copolymer has a $M_n$ of at least 5,000 and the other block has a $M_n$ of at least 20,000. In some other embodiments, any one of the blocks of the block polymers of this invention has a $M_n$ of higher than 100,000, higher than 200,000 or higher than 500,000. As already noted above, the number average molecular weight ($M_n$) of the block copolymers can be determined by any of the known techniques, such as for example, by gel permeation chromatography (GPC) equipped with suitable detector and calibration standards, such as, differential refractive index (RI) detector or multi-angle laser light scattering (LS) detector, calibrated with narrow-distribution polystyrene standards. As also noted, each of the block copolymers of this invention typically exhibit very low polydispersity index ($PDI=M_w/M_n$). In general, the PDI of each of the blocks of the block copolymers of this invention is less than 2. In some embodiments the PDI is less than 1.5, less than 1.4, less than 1.3, less than 1.2 or less than 1.1. However, it should be noted that in some embodiments the PDI can be higher than 2, such as for example, higher than 3.

In one of the embodiments, various diblock polymers can be formed by practicing the process of this invention. Non-limiting examples of such diblock polymers formed from the process of this invention may be enumerated as follows:

a block copolymer derived from 5-hexylbicyclo[2.2.1]hept-2-ene and norbornenyl-2-trifluoromethyl-3,3,3-trifluoropropan-2-ol (HexNB-b-HFANB);

a block copolymer derived from 5-butylbicyclo[2.2.1]hept-2-ene and norbornenyl-2-trifluoromethyl-3,3,3-trifluoropropan-2-ol (BuNB-b-HFANB);

a block copolymer derived from 5-butylbicyclo[2.2.1]hept-2-ene and 1-(4-(bicyclo[2.2.1]hept-5-en-2-yl)butyl)-3,4-dimethyl-1H-pyrrole-2,5-dione ($C_4F_9$NB-b-BuDM-MINB);

a block copolymer derived from norbornenyl-2-trifluoromethyl-3,3,3-trifluoropropan-2-ol and 2-(bicyclo[2.2.1]hept-5-en-2-yl)bicyclo[2.2.1]heptane (HFANB-b-NBANB);

a block copolymer derived from 5-hexylbicyclo[2.2.1]hept-2-ene and 2-(bicyclo[2.2.1]hept-5-en-2-yl)bicyclo[2.2.1]heptane (HexNB-b-NBANB); and a block copolymer derived from 5-benzylbicyclo[2.2.1]hept-2-ene and 5-n-perfluorobutylbicyclo[2.2.1]hept-2-ene (BnNB-b-$C_4F_9$NB).

In another embodiment, various triblock polymers can formed by practicing the process of this invention. Non-limiting examples of such triblock polymers formed from the process of this invention may be enumerated as follows:

a block polymer derived from 5-butylbicyclo[2.2.1]hept-2-ene, norbornenyl-2-trifluoromethyl-3,3,3-trifluoropropan-2-ol and 5-butylbicyclo[2.2.1]hept-2-ene (BuNB-b-HFANB-b-BuNB);

a block polymer derived from 5-butylbicyclo[2.2.1]hept-2-ene, 5-benzylbicyclo[2.2.1]hept-2-ene and 2-(bicyclo[2.2.1]hept-5-en-2-yl)bicyclo[2.2.1]heptane (BuNB-b-BnNB-b-NBANB); and a block polymer derived from norbornenyl-2-trifluoromethyl-3,3,3-trifluoropropan-2-ol, 5-butylbicyclo[2.2.1]hept-2-ene, and norbornenyl-2-trifluoromethyl-3,3,3-trifluoropropan-2-ol (HFANB-b-BuNB-b-HFANB).

Pervaporation Membrane Applications

As noted, the block polymers of this invention exhibit several unique properties, and therefore, are useful in several different applications, including as membrane materials for separation, electronic and/or opto-electronic applications, among others.

With the increased interest in producing biological fuel, such as ethanol, butanol, and the like, there is a heightened interest in developing environmentally friendly separation processes that economically separate organic materials from water. There is also growing need for purification of water stream contaminated by an industrial process as well as to the isolation of an organic product from an aqueous fermentation broth designed to form various organic solvents via a biological process, for example, phenol from the broth of a fermentation reactor or any other biologically formed broth, e.g., an algae broth. Also, there is a growing interest in separating value-added products from biological and industrial waste including any biomass-derived waste. While it is well known to use processes such as distillation and gas stripping to effect such separations, these conventional processes, particularly distillation, are generally characterized by high capital and energy costs thus often making such conventional processes problematic, for example, it has been noted that in excess of 60% of the heating value of a biofuel such as butanol can be "wasted" if conventional separation processes are employed.

Even more importantly the organic products, particularly, the organic solvents that are either made by the above noted bio-processes or extracted from organic wastes are gaining more and more industrial applications. For instance, about half of the n-butanol produced and its esters (e.g., n-butyl acetate) are used as solvents in the coatings industry, including as solvents for dyes, e.g., printing inks. Other well known applications of butyl esters of dicarboxylic acids, phthalic anhydride and acrylic acid include as plasticizers, rubber additives, dispersants, semisynthetic lubricants, additives in polishes and cleaners, e.g., floor cleaners and stain removers, and as hydraulic fluids. Butanol and its esters are also used as solvents, including as extractants in the production of drugs and natural products, such as antibiotics, hormones, vitamins, alkaloids and camphor. Various other uses of butanol and its esters and ethers include as solubilizer in the textile industry, e.g. as additive in spinning baths or as carrier for coloring plastics, as additives in de-icing fluids, additive in gasoline for spark-ignition engines, as feedstock for the production of glycol ethers, among various other uses.

Therefore, an alternate process for effecting such separations known as pervaporation has received considerable attention as a solution to the aforementioned "waste". In a pervaporation process, a charge liquid, typically a mixture of two or more liquids, such as a fermentation broth, is brought into contact with a membrane film having is the property to allow one component of the charge liquid to preferentially permeate the membrane. This permeate is then removed as a vapor from the downstream side of the membrane film, generally by applying vacuum on the permeate side of the membrane. Particularly, pervaporation process has proven to be a method of choice in the separation of liquid mixtures having similar volatilities, such as azeotropic mixtures that are difficult to separate by conventional methods. While polymers such as polyimides, polyether-polyamide, polydimethylsiloxanes and the like have been used to form pervaporation membranes with some success, none have demonstrated thus far the necessary characteristics needed for a commercially viable membrane material. For example, pervaporation membranes, such as PERVAP 1060 (made from poly(dimethylsiloxane), PDMS), PERVAP 1070 (made from zeolite, ZSM-5, filled PDMS) (Sulzer Chemtech Membrane Systems A.G., Neunkirchen, Germany) and PEBA (block copolymer polyether-polyamide, GKSS-Forschungszentrum Geesthacht GmbH, Geesthacht, Germany) are available for the separation of various low volatile organics from aqueous mixtures. However, there is still a need to develop membranes having better performance, which can provide efficient separation of organics from aqueous mixtures at lower capital and reduced operating cost.

Disclosed herein are embodiments in accordance with the present invention that encompass monomers, polymer composition embodiments, film and film composite embodiments and pervaporation membrane embodiments formed therefrom that advantageously provide hitherto unachievable separation of organics from a variety of mixtures including fermentation broth, industrial waste, among others.

Exemplary embodiments of the present invention will be described hereinbelow. Various modifications, adaptations or variations of such exemplary embodiments may become apparent to those skilled in the art as such are disclosed. It will be understood that all such modifications, adaptations or variations that rely upon the teachings of the present invention, and through which these teachings have advanced the art, are considered to be within the scope and spirit of the present invention. For example, while the exemplary embodiments described herein generally reference the separation of butanol and/or phenol from an aqueous charge liquid, such are not meant to limit the present invention only to embodiments for butanol and/or phenol separation. Thus some embodiments of the present invention encompass the separation of any organic material from an aqueous based charge liquid where an appropriate pervaporation membrane can be formed from a block copolymer of this invention. For example, some embodiments encompass the separation of a hydrophobic organic material from a hydrophilic charge liquid using an appropriate pervaporation membrane as disclosed herein. Still other embodiments of the present invention encompass separation of non-polar and polar organic materials. Examples of such separations include, but are not limited to, aromatics such as benzene or toluene from water miscible alcohols such as methanol or ethanol and the separation of non-polar hydrocarbyl-based materials such as hexanes and heptanes from polar heterocarbyl-based materials. Various other organics also include volatile organic solvents, such as tetrahydrofuran (THF), ethyl acetate (EA), acetone, methyl ethyl ketone (MEK), methyl isobutyl ketone (MIBK), and the like, all of which can be present either in a fermentation broth or in an industrial waste.

The expected behavior of a pervaporation membrane made of a hydrophobic polymer is to become plasticized and/or swollen as the organic concentration increases. Plasticized and/or swollen membranes generally cause an undesirable increase in permeability of both the organic and water, with the water permeability generally increasing relatively more than the organic permeability thus resulting in a reduction in separation factor. Unexpectedly, pervaporation membranes made from block polymers of this invention, which are generally hydrophobic, exhibit a behavior opposite as to what is generally expected. The pervaporation membranes as described herein have a separation factor that increases dramatically with increasing feed concentration (that is, an increase in the organic concentration of a feed stream).

Typically in pervaporation, a multi-component liquid stream is passed across a pervaporation membrane that preferentially permeates one or more of the components. As the multi-component liquid stream flows across the pervaporation membrane surface, the preferentially permeated components pass through the pervaporation membrane and are removed as a permeate vapor. Transport through the pervaporation membrane is induced by maintaining a vapor pressure on the permeate side of the pervaporation membrane that is lower than the vapor pressure of the multi-component liquid stream. The vapor pressure difference can be achieved, for example, by maintaining the multi-component liquid stream at a higher temperature than that of the permeate stream. In this example, the latent heat of evaporation of the permeate components is supplied to the multi-component liquid stream for maintaining the feed temperature and for continuing the pervaporation process. Alternatively, the vapor pressure difference is typically achieved by operating at below atmospheric pressure on the permeate side of the pervaporation module. A partial vacuum on the permeate side of the polynorbornene pervaporation membrane can be obtained by any one of: relying on the pressure drop that occurs as a result of the cooling and condensation that takes place in the condenser unit, and/or by use of a vacuum pump. An optional sweep gas on the permeate side can facilitate the pervaporation process by lowering the concentration of the permeating components. The vapor pressure of the feed liquid can be optionally raised by heating the fermentation broth. While polynorbornene pervaporation membranes have already been disclosed in U.S. Pat. No. 8,215,496, pertinent disclosures of which are hereby incorporated by reference, and where such membranes have met with some success, the block copolymer pervaporation membrane disclosed and claimed herein provide significant improvements over such previously disclosed membranes, which is apparent from the following disclosure, Accordingly, there is provided a pervaporation membrane encompassing a block polymer of the formula (VI) or (VII) as disclosed hereinabove. That is, any of the diblock or triblock polymers of this invention can be used to form the pervaporation membranes of this invention. In one of the embodiments the pervaporation membrane of this invention encompasses a diblock copolymer of formula (VI) of this invention. In another embodiment the pervaporation membrane of this invention encompasses a triblock polymer of formula (VII) of this invention.

In another embodiment, the pervaporation membrane of this invention is made from a diblock copolymer selected from the group consisting of:

a block copolymer derived from 5-hexylbicyclo[2.2.1]hept-2-ene and norbornenyl-2-trifluoromethyl-3,3,3-trifluoropropan-2-ol (HexNB-b-HFANB);

a block copolymer derived from 5-butylbicyclo[2.2.1]hept-2-ene and norbornenyl-2-trifluoromethyl-3,3,3-trifluoropropan-2-ol (BuNB-b-HFANB);

a block copolymer derived from 5-butylbicyclo[2.2.1]hept-2-ene and 1-(4-(bicyclo[2.2.1]hept-5-en-2-yl)butyl)-3,4-dimethyl-1H-pyrrole-2,5-dione ($C_4F_9$NB-b-BuDM-MINB);

a block copolymer of derived from norbornenyl-2-trifluoromethyl-3,3,3-trifluoropropan-2-ol and 2-(bicyclo[2.2.1]hept-5-en-2-yl)bicyclo[2.2.1]heptane (HFANB-b-NBANB); and a block copolymer of derived from 5-hexylbicyclo[2.2.1]hept-2-ene and 2-(bicyclo[2.2.1]hept-5-en-2-yl)bicyclo[2.2.1]heptane (HexNa-b-NBANB).

In another embodiment, the pervaporation membrane of this invention is made from a triblock polymer selected from the group consisting of:

a block copolymer derived from 5-butylbicyclo[2.2.1]hept-2-ene, norbornenyl-2-trifluoromethyl-3,3,3-trifluoropropan-2-ol and 5-butylbicyclo[2.2.1]hept-2-ene (BuNB-b-HFANB-b-BuNB); and a block copolymer derived from norbornenyl-2-trifluoromethyl-3,3,3-trifluoropropan-2-ol, 5-butylbicyclo[2.2.1]hept-2-ene, and norbornenyl-2-tri fluoromethyl-3,3,3-trifluoropropan-2-ol (HFANB-b-BuNB-b-HFANB)

The pervaporation membranes of this invention can readily be formed by any of the techniques known in the art. For example, a suitable diblock or triblock polymer of formula (VI) or (VII) of this invention encompassing desirable repeat units of polycycloalkyl norbornene-type monomers of formula (IVA) is generally dissolved in a suitable organic solvent to form a solution. The polymer solution is then generally filtered through a suitable filter to remove any residual contaminants. After filtration, trapped gas can be removed. The polymer solution can then be formed into a film by any of the known methods in the art. For instance, the polymer solution is poured onto a substrate and pulled to form a film. The film is then dried and removed from the substrate, if any, and is ready for use. The films formed in this fashion are generally considered as single thickness films, specific examples of this embodiment are further described below. In some embodiments, the films are cast as double thickness films by forming a second layer of film on the first formed film. In some other embodiments the polymer solution is applied on to a polymer web to form a reinforced membrane, either on a sheet to form a supported membrane or on a substrate panel to form a non-supported membrane. In other embodiments the polymer solution can be suitably cast to form a tubular composite, or a hollow fiber. Accordingly, in one of the embodiments, the pervaporation membrane of this invention is in a form of a tubular composite, hollow fiber, a dense film flat sheet, or a thin film composite.

The pervaporation membranes of this invention can be in any suitable form to effect separation of a desirable material, for example butanol, from a fermentation broth. Examples include spiral wound modules, fiber membranes including hollow fiber membranes, tubular membranes, and flat sheet membranes, such as in a plate and frame configuration, a supported or unsupported dense film, or a thin film composite.

When the block polymer pervaporation membranes are in an unsupported dense film form, the thickness of the dense film is from about 1 micron to about 500 microns. In another embodiment, the thickness of the dense film is from about 5 microns to about 100 microns.

When the pervaporation membranes are in the form of a thin film composite, such membranes can be thinner than unsupported membranes, for example as thin as about 0.1 is microns. Further, the membrane contains at least one layer of block polymer and at least one layer of a non-block polymer component. Such composites can contain multiple layers of block polymer membranes and multiple layers of non-block polymer component. Examples of the non-block polymer component include various other polymers and inorganic materials. Examples of such polymers include polyethylenes including TYVEK®, polypropylenes, polyesters, polyimides, polycarbonates, polytetrafluoroethylene, poly(vinylidene fluoride) (PVDF), poly(methyl methacrylate) (PMMA), polyacrylonitrile (PAN), mixed co- and ter-polymers thereof, and the like. Examples of inorganic materials include zeolites, glass frits, carbon powder, metal sieves, metal screens, metal frit, and the like.

A schematic diagram of the pervaporation process is shown in FIG. 1. As depicted, a feed containing numerous species is charged into a pervaporation module 100 and to a liquid chamber 102 on the feed side thereof. Vapor chamber 104 on the permeate side is separated from the liquid chamber 102 by a pervaporation membrane 106. The vapor phase is extracted from the feed liquid through the pervaporation membrane 106 which is selective for a given permeate, and the permeate vapor, which is enriched in the given permeate relative to the feed liquid, and is removed from the pervaporation module 100, generally by condensation thereof.

Utilizing block polymer pervaporation membranes, pervaporation can be employed to treat a fermentation broth containing, for example, biobutanol, ethanol or phenol and one or more other miscible components. More specifically, a fermentation broth can be added to the liquid chamber 102 and thus placed in contact with one side of pervaporation membrane 106 while a vacuum or gas purge is applied to vapor chamber 104. The fermentation broth can be heated or unheated. The components in the fermentation broth sorb into/onto pervaporation membrane 106, permeate through and evaporate into the vapor phase. The resulting vapor or permeate, for example butanol (or phenol), is then condensed and collected. Due to different species in the fermentation broth having different affinities for the pervaporation membrane and different diffusion rates through the membrane, even a component at low concentration in the feed can be highly enriched in the permeate. Accordingly, in one of the embodiments there is provided a pervaporation membrane, which is capable of preferential permeability to a volatile organic over water. The permeability of a volatile organic through pervaporation membrane of the present invention generally increases with increasing organic concentration of a feed stream. In another embodiment, such volatile organics include without any limitation butanol, phenol, and the like.

Figure 2:
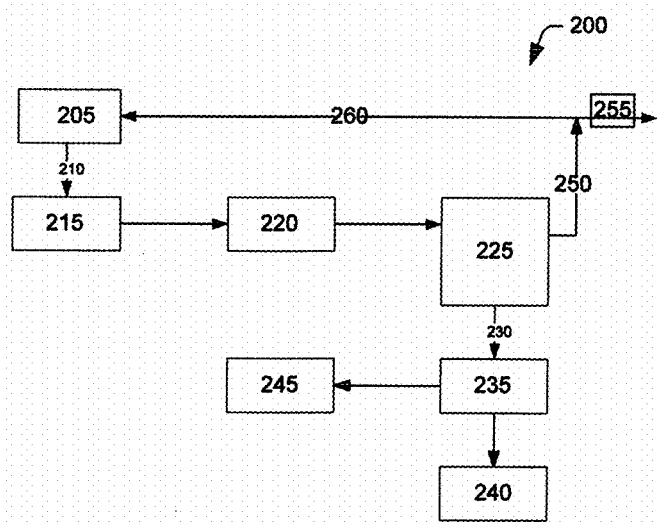
FIG. 2 depicts a pervaporation system in accordance with embodiments of the invention.

FIG. 2 depicts an exemplary pervaporation system 200 that can be employed to separate butanol, or other desirable materials, from a crude fermentation broth (or an aqueous industrial waste or other waste including biomass-waste) containing a valuable organic compound, such as biobutanol or phenol. Crude fermentation broth (or other waste including industrial and/or biomass as a feed stream 210 from a feed tank 205 is pumped via pump 215 through a heater 220 to increase its temperature. The fermentation broth is then charged under pressure to a pervaporation module 225 containing a pervaporation membrane. Permeate vapor 230 containing butanol (or phenol) is obtained from the pervaporation module 225 by applying vacuum (using vacuum pump 245), where the butanol vapor (or phenol vapor) is condensed in a condenser 235, and collected in collector 240. Residual fermentation broth or retentate stream 250 that does not pass through the polynorbornene pervaporation membrane can be either discharged (255) from the system 200 or directed to a recycling stream 260 and returned to the feed tank 205.

Supplemental methods that complement the pervaporation process include removing solids from the fermentation broth by centrifugation, filtration, decantation, dephlegmation or the like; and increasing the concentration of butanol in the permeate using adsorption, distillation or liquid-liquid extraction or the like.

Butanol from biomass is often referred to as biobutanol. Biobutanol can be produced by fermentation of biomass by the acetone-butanol-ethanol fermentation (A.B.E.) process. See, for example, S-Y Li, et al. Biotechnol. Prog. 2011, vol. 27(1), 111-120. The process uses the bacterium of the genus *Clostridium*, such as *Clostridium acetobutylicum*, but others including *Saccharomyces cerevisiae, Zymomonas mobilis, Clostridium thermohydrosulfuricum, Escherichia coli, Candida pseudotropicalis*, and *Clostridium beijerinckii*, can be used. Biobutanol can also be made using genetically modified yeasts for the production of biobutanol from cellulosic materials. The crude fermentation broth containing biobutanol can be advantageously processed by the pervaporation membrane depicted in FIG. 1 and/or the pervaporation system depicted in FIG. 2 to provide concentrated butanol, as compared to the concentration thereof in the crude broth. It should further be noted that the pervaporation membranes of this invention are also useful for separation of various alcohols other than butanol, including ethanol and phenol from the respective fermentation broths or industrial or biomass waste.

Fermentation broths generally contain a variety of carbon substrates. In addition to the carbon source, fermentation broths can contain suitable minerals, salts, cofactors, buffers and other components, known to those skilled in the art, suitable for the growth of the cultures and promotion of the enzymatic pathway necessary for butanol production. Examples of fermentation broths that are commercially available include Luria Bertani (LB) broth, Sabouraud Dextrose (SD) broth, or Yeast Medium (YM) broth. Any of these known fermentation broths can be used in the present invention in order to separate the volatile organics from such broths.

Similarly, it should be noted that various other organic products are selectively formed from a fermentation process. For instance, phenol often termed as "green phenol" can be formed from appropriate waste, including biological waste or industrial waste, and by employing appropriate biological organisms to effect the fermentation to proceed selectively to phenol. It has been reported that phenol can be selectively produced from a recombinant strain of the solvent-tolerant bacterium *Pseudoinomas putida* S12, see, for example, L. Heerema, et. al. Desalination, 200 (2006), pp 485-487. It has also been reported that various other yeast strains also produce phenol, all of which use bacterium of the genus *Saccharomyces*, such as *Saccharomyces cerevisiae* r.f. *bayanus*, EP 171 Lalvin; *Saccharomyces bayanus*, Ever; *Saccharomyces ellipsoideus*, Ceppo 20 Castelli; *Saccharomyces oviformis*, Ceppo 838 Castelli; *Saccharomyces cerevisiae* r.f. *cerevisiae*, K1 Lalvin; and *Saccharomyees cerevisiae*, D254 Lalvin. These organisms are able to produce different amounts of phenolic substance from a synthetic and/or natural organic sources whose main carbon source is glucose. See, M. Giaccio, J. Commodity Science (1999), 38(4), 189-200. In general, as used herein, "green phenol" generically refers to phenol produced by a fermentation broth, which contains phenol from about 0.1% to about 6% phenol. In other embodiments, the fermentation broth contains from about 0.5% to about 3% phenol.

As used herein, "butanol" generically refers to n-butanol and its isomers. In some embodiments in accordance with the present invention, the fermentation broth contains from about 0.1% to about 10% butanol. In other embodiments, the fermentation broth contains from about 0.5% to about 6% butanol. In some other embodiments, the fermentation broth contains from about 1% to about 3% butanol. Generally, the pervaporation membranes described herein are effective at separating volatile organics, such as butanol, ethanol or phenol from fermentation broths containing relatively low to high levels of volatile organics, yet in some embodiments the fermentation broth contains at least about 1% volatile organics.

It should further be noted that certain of the "green phenol" feedstock can also be generated using phenolic based resins, such as novolak resins, and the like. Such feed streams can also be used in the pervaporation process of this invention where the phenol can be separated and/or enriched from the waste stream. Furthermore, various such phenol streams also contain certain inorganic and organic salts as impurities. As a result, it is difficult to remove such inorganic salts from the feed stream and to obtain phenol in the pure enriched form. However, surprisingly, it has now been found that the pervaporation membranes of the instant invention are capable of separating such inorganic and organic salts. Representative examples of inorganic salts include, without any limitation, salts of lithium, sodium, potassium, magnesium, calcium, barium and the like. The salts of these metals with any counteranions can be used in this invention. Such examples of non-limiting anions include, phosphate, sulfate, acetate, benzoate, and the like. However, other anions such as methanesulfonate (mesylate), trifluoromethanesulfonate (triflate), p-toluenesulfonate (tosylate), and halides, such as fluoride, chloride, bromide and iodide can also be separated from the feed stream.

In one of the embodiments there is provided a process of separating an organic product from a feedstock selected from a fermentation broth or an industrial waste containing the organic product, such as butanol, ethanol, phenol, THF, ethyl acetate, acetone, toluene, MEK, MIRK, etc. In some embodiments, the fermentation broth is charged to a pervaporation module containing a pervaporation membrane formed by any one of the block polymers as described herein. The permeate vapor containing the organic product from the pervaporation module is then collected. In this process, it may be advantageous to heat the crude fermentation broth feed to a temperature that facilitates the organic product passage through the pervaporation membrane of this invention. In one embodiment, the crude fermentation broth feed is heated to a temperature from about 30° C. to about 110° C. In another embodiment, the crude fermentation broth feed is heated to a temperature from about 40° C. to about 90° C. In yet another embodiment, the crude fermentation broth feed is heated to a temperature from about 50° C. to about 70° C. It should be noted that the desired temperature may depend upon the type of organics that is being separated. For example, relatively lower temperatures are employed in the separation of butanol whereas somewhat higher temperatures are desirable while separating phenol. Accordingly, in one of the embodiments the fermentation broth containing butanol feed is heated to a temperature in the range of from about 30° C. to about 90° C. In another embodiment the fermentation broth containing phenol feed is heated to a temperature in the range of from about 40° C. to about 110° C.

To facilitate pervaporation, a suitable vacuum can be applied to the vapor chamber of the pervaporation module. In one embodiment, the vacuum applied is from about 0.1 in Hg to about 25 in Hg. In another embodiment, the vacuum applied is from about 0.15 in Hg to about 5 in Hg. In another embodiment, the vacuum applied is from about 0.2 in Hg to about 4 in Hg.

Other processes include methods of increasing a separation factor for an organic product, such as butanol, phenol or ethanol, as a concentration of the organic product increases in a pervaporation feed stream. Such methods involve using a pervaporation membrane to separate the organic product from the pervaporation feed stream.

As used herein, "SF" is the separation factor which is a measure of quality of the separation of a first species relative to a second species and is defined as the ratio of the ratio of permeate compositions to the ratio of the feed compositions.

As used herein, flux is the amount that flows through a unit area of a membrane per unit of time.

Flux and SF can also be described by the following equations:

$$\text{Flux } (J) = \text{mass}/(\text{area} \cdot \text{time})$$

Separation Factor (SF)

$$SF_{12} = \left(\frac{\frac{y_1}{y_2}}{\frac{x_1}{x_2}}\right) = \left(\frac{\frac{J_1}{J_2}}{\frac{x_1}{x_2}}\right) = SF_{VLE}SF_{membrane}$$

$y$ = Permeate concentration, $x$ = Feed liquid concentration

Accordingly, the efficiency of a pervaporation membrane can be evaluated at least in two respects, a separation factor (the ratio of enrichment obtained when the liquid mixture permeates through the membrane) and the flux at which a liquid mixture permeates through the polymeric membrane. Thus, the higher the separation factor and flux of a membrane, the higher the separation efficiency of such membrane. Of course this is a very simplified analysis as low separation factors can often be overcome through the use of multistage membrane processes, and where the flux factor of a membrane is low, often forming such a membrane with a high surface area can overcome low flux. Thus while the separation and flux factors are important considerations, other factors such as a membrane's strength, elasticity, resistance to becoming fouled during use, thermal stability, free volume and the like are also important considerations in selecting the best polymer for forming a pervaporation membrane.

It has now been found that the pervaporation membrane of this invention has a suitable separation factor (SF) for volatile organics, such as butanol, phenol or ethanol to provide an effective means to remove volatile organics, such as butanol, phenol or ethanol from a fermentation broth or from other waste as described herein. In one embodiment, the pervaporation membrane has a SF for volatile organics, such as butanol, phenol or ethanol of at least about 5. In another embodiment, the pervaporation membrane has a SF for volatile organics, such as butanol, phenol or ethanol of at least about 10. In yet another embodiment, the pervaporation membrane has a SF for volatile organics, such as butanol, phenol or ethanol of at least about 15. In still yet other embodiments, the pervaporation membrane has a SF for volatile organics, such as butanol, phenol or ethanol of at least about 20, at least about 25, or at least about 30. Moreover, any of the foregoing SFs can be achieved when the concentration of volatile organics, such as butanol, phenol or ethanol in a feed stream is 0.5% or higher, 1% or higher, 2% or higher, 3% or higher, or 4% or higher, or 5% or higher, or 6% or higher.

A suitable flux for volatile organics, such as butanol, phenol or ethanol can be achieved using block polynorbornene pervaporation membranes of the present invention to provide an effective means to remove volatile organics, such as butanol, phenol or ethanol from a fermentation broth. In one embodiment, a flux for volatile organics, such as butanol, phenol or ethanol of at least about 100 g/m²/hr can be achieved using such block polynorbornene pervaporation membranes. In another embodiment, a flux for volatile organics, such as butanol, phenol or ethanol of at least about 150 g/m²/hr can be achieved; in yet another embodiment, a flux for volatile organics, such as butanol, phenol or ethanol of at least about 200 g/m²/hr can be achieved and in still another embodiment, a flux for volatile organics, such as butanol, phenol or ethanol of at least about 250 g/m²/hr can be achieved using such polynorbornene pervaporation membranes. Furthermore, unlike what is generally found using previously known non-polynorbornene pervaporation membranes, any of the foregoing fluxes can be achieved when the concentration of volatile organics, such as butanol, phenol or ethanol in a feed stream is 0.5% or higher, 1% or higher, 2% or higher, 3% or higher, or 4% or higher, or 5% or higher, or 6% or higher.

It has been surprisingly found that various block polymers as described herein are suited for use in forming pervaporation membranes. It has been further observed that suitable combination of diblock copolymer or triblock terpolymer as described herein are well suited for tailoring the resulting polymer's physical (e.g., glass transition temperature ($T_g$), modulus, free volume, hydrophobicity, hydrolytic stability, and the like) and pervaporation characteristics (e.g., SF and flux). It should further be noted that block polymers of this invention can be tailored to exhibit relatively high glass transition temperatures, the block polymers of this invention can possibly offer the ability of operation as a pervaporation membrane at temperatures higher than possible for currently known membranes.

Advantageously, it has now been found that a combination of different types of blocks encompassing different polynorbornene repeat units affords membranes featuring desirable flux and separation factors. Thus, for example, employing a diblock polymer having a relatively alcoholphilic blocks containing monomeric repeat units derived from monomers such as HFANB in combination with relatively hydrophobic blocks containing monomeric repeat units such as BuNB provides a diblock polymer, HFANB-b-BuNB, having surprising properties. Such block polymers can be fabricated to form microphase separated membranes which feature unique properties in separating an organic product from a feedstock as described hereinabove and hereafter. More specifically, by increasing the mole ratios (i.e, the weight fraction) of the alcoholphilic blocks (for example HFANB) it is now possible to control the performance of the membrane resulting therefrom. For instance it has now been found that increase of weight fraction of alcoholphilic blocks generally increases the flux as well as separation factor. Thus in one of the embodiments, the weight fraction of the alcoholphilic block, such as for example, weight fraction of HFANB, $W_{HFANB}$, in a diblock polymer, HFANB-b-BuNB, is from 0.5 to 0.95; in other embodiments it is from about 0.6 to 0.85; and in other embodiments it is from 0.7 to 0.8. In some embodiments, the weight fraction of the alcoholphilic block, such as for example, weight fraction of HFANB, $W_{HFANB}$, in a diblock polymer, HFANB-b-BuNB, is 0.5.

Similarly, the triblock polymers can have various combinations of alcoholphilic blocks with a hydrophobic blocks, such as for example, alcoholphilic block-hydrophobic block-alcoholphilic block; hydrophobic block-alcoholphilic block-hydrophobic block; hydrophobic block-hydrophobic block-alcoholphilic block; alcoholphilic block-alcoholphilic block-hydrophobic block; and the like.

Accordingly, in one of the embodiments there is provided a method of separating an organic product from a feedstock selected from a fermentation broth or a waste containing the organic product comprising:

charging the feedstock to a pervaporation module containing a pervaporation membrane formed by a polymer according to claim 1; and collecting a permeate vapor containing the organic product from the pervaporation module.

As already noted, the pervaporation can be carried out at any desirable temperature. Thus, in one of the embodiments, pervaporation is carried out where the fermentation broth is charged to the pervaporation module at a temperature from about 30° C. to about 110° C. The vacuum applied to the pervaporation module in this embodiment may range from about 0.1 in Hg to about 25 in Hg.

In this aspect of the method of this invention, the pervaporation membrane is formed by a polymer selected from:

a block copolymer derived from 5-hexylbicyclo[2.2.1]hept-2-ene and norbornenyl-2-trifluoromethyl-3,3,3-trifluoropropan-2-ol (HexNB-b-HFANB);

a block copolymer derived from 5-butylbicyclo[2.2.1]hept-2-ene and norbornenyl-2-trifluoromethyl-3,3,3-trifluoropropan-2-ol (BuNB-b-HFANB);

a block copolymer derived from 5-butylbicyclo[2.2.1]hept-2-ene and 1-(4-(bicyclo[2.2.1]hept-5-en-2-yl)butyl)-3,4-dimethyl-1H-pyrrole-2,5-dione ($C_4F_9$NB-b-BuDM-MINB);

a block copolymer of derived from norbornenyl-2-trifluoromethyl-3,3,3-trifluoropropan-2-ol and 2-(bicyclo[2.2.1]hept-5-en-2-yl)bicyclo[2.2.1]heptane (HFANB-b-NBANB); and a block copolymer of derived from 5-hexylbicyclo[2.2.1]hept-2-ene and 2-(bicyclo[2.2.1]hept-5-en-2-yl)bicyclo[2.2.1]heptane (HexNB-b-NBANB).

In another embodiment, the method of this aspect of the invention encompasses a pervaporation membrane formed by a polymer selected from:

to a block terpolymer derived from 5-butylbicyclo[2.2.1]hept-2-ene, norbornenyl-2-trifluoromethyl-3,3,3-trifluoropropan-2-ol and 5-butylbicyclo[2.2.1]hept-2-ene (BuNB-b-HFANB-b-BuNB); and a block terpolymer derived from norbornenyl-2-trifluoromethyl-3,3,3-trifluoropropan-2-ol, 5-butylbicyclo[2.2.1]hept-2-ene, and norbornenyl-2-trifluoromethyl-3,3,3-trifluoropropan-2-ol (HFANB-b-BuNB-b-HFANB).

In this aspect of the method of this invention the organic product which is separated from biomass or organic waste is butanol, ethanol or phenol.

In another aspect of this invention there is also provided a method of separating volatile organic products, such as for example, butanol or phenol from a feedstock selected from a fermentation broth or a waste containing such volatile organics, such as, butanol or phenol. The method encompasses the following:

charging the feedstock to a pervaporation module containing a pervaporation membrane formed by a polymer selected from:

a block copolymer derived from 5-hexylbicyclo[2.2.1]hept-2-ene and norbornenyl-2-trifluoromethyl-3,3,3-trifluoropropan-2-ol (HexNB-b-HFANB);

a block copolymer derived from 5-butylbicyclo[2.2.1]hept-2-ene and norbornenyl-2-trifluoromethyl-3,3,3-trifluoropropan-2-ol (BuNB-b-HFANB);

a block copolymer derived from 5-butylbicyclo[2.2.1]hept-2-ene and 1-(4-(bicyclo[2.2.1]hept-5-en-2-yl)butyl)-3,4-dimethyl-1H-pyrrole-2,5-dione ($C_4F_9$NB-b-BuDM-MINB);

a block copolymer of derived from norbornenyl-2-trifluoromethyl-3,3,3-trifluoropropan-2-ol and 2-(bicyclo[2.2.1]hept-5-en-2-yl)bicyclo[2.2.1]heptane (HFANB-b-NBANB);

a block copolymer of derived from 5-hexylbicyclo[2.2.1]hept-2-ene and 2-(bicyclo[2.2.1]hept-5-en-2-yl)bicyclo[2.2.1]heptane (HexNB-b-NBANB);

a block terpolymer derived from 5-butylbicyclo[2.2.1]hept-2-ene, norbornenyl-2-trifluoromethyl-3,3,3-trifluoropropan-2-ol and 5-butylbicyclo[2.2.1]hept-2-ene (BuNB-b-HFANB-b-BuNB); and a block terpolymer derived from norbornenyl-2-trifluoromethyl-3,3,3-trifluoropropan-2-ol, 5-butylbicyclo[2.2.1]hept-2-ene, and norbornenyl-2-trifluoromethyl-3,3,3-trifluoropropan-2-ol (HFANB-b-BuNB-b-HFANB); and collecting a permeate vapor containing butanol or phenol from the pervaporation module.

In a further aspect of this invention there is also provided a method of forming a membrane, which encompasses pouring a solution of a block polymer of the formula (VI) or (VII) as described herein onto a suitable substrate and drying the substrate at a suitable temperature to form the membrane. As already noted above, the drying of the membrane so formed can be carried out at any of the temperatures to obtain the intended result. Typically, the drying is carried out at a temperature in the range of from about 30° C. to about 120° C., in some other embodiments it is from about 50° C. to 100° C., or from 70° C. to 90° C. The time required to dry the membrane can range from about 10 minutes to 1 day, or 30 minutes to 20 hours, or 1 hour to 16 hours.

Any of the block polymers of this invention as described herein can be employed to form the membranes in this aspect of the invention. Non-limiting examples of such diblock copolymers may be enumerated as follows:

a block copolymer derived from 5-hexylbicyclo[2.2.1]hept-2-ene and norbornenyl-2-trifluoromethyl-3,3,3-trifluoropropan-2-ol (HexNR-b-HFANB);

a block copolymer derived from 5-butylbicyclo[2.2.1]hept-2-ene and norbornenyl-2-trifluoroethyl-3,3,3-trifluoropropan-2-ol (BuNB-b-HFANB);

a block copolymer derived from 5-butylbicyclo[2.2.1]hept-2-ene and 1-(4-(bicyclo[2.2.1]hept-5-en-2-yl)butyl)-3,4-dimethyl-1H-pyrrole-2,5-dione ($C_4F_9$NB-b-BuDM-MINB);

a block copolymer of derived from norbornenyl-2-trifluoromethyl-3,3,3-trifluoropropan-2-ol and 2-(bicyclo[2.2.1]hept-5-en-2-yl)bicyclo[2.2.1]heptane (HFANB-b-NBANB); and a block copolymer of derived from 5-hexylbicyclo[2.2.1]hept-2-ene and 2-(bicyclo[2.2.1]hept-5-en-2-yl)bicyclo[2.2.1]heptane (HexNB-b-NBANB).

In another embodiment of this method of the invention, the non-limiting examples of such triblock polymers that can be employed to form the membranes of this invention may be enumerated as follows:

a block terpolymer derived from 5-butylbicyclo[2.2.1]hept-2-ene, norbornenyl-2-trifluoromethyl-3,3,3-trifluoropropan-2-ol and 5-butylbicyclo[2.2.1]hept-2-ene (BuNR-b-EFANB-b-BuNB); and a block terpolymer derived from norbornenyl-2-trifluoromethyl-3,3,3-trifluoropropan-2-ol, 5-butylbicyclo[2.2.1]hept-2-ene, and norbornenyl-2-trifluoromethyl-3,3,3-trifluoropropan-2-ol (HFANB-b-BuNB-b-HFANB).

Surprisingly, it has now been found that forming a solution of the block polymer in a suitable solvent or a solvent mixture and drying results in phase separation, which may be attributed to some of the superior properties observed in selectively separating the to organic volatiles from biomass or organic waste. It has now been observed that a suitable selection of a solvent or a mixture of solvents to dissolve the block polymer results in this phase separation as observed by different surface morphologies. Examples of suitable solvents for dissolving the block polymer include hydrocarbon solvents such as toluene and other ether solvents such as tetrahydrofuran (THF). Surprisingly, it has now been found that use of a mixture of solvents, such as, hydrocarbon solvent and ether, for example, toluene and THF results in significant change in the surface morphology of the membrane formed therefrom.

Figure 3:
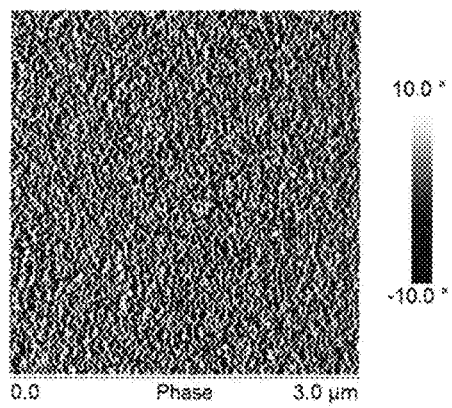
FIGS. 3 to 5 show respectively atomic force micrographs (AFM) of membranes formed from BuNB-HFANB (1:2) block copolymer (FIG. 3), BuNB-HFANB (2:1) block copolymer (FIG. 4) and HFANB-BuNB-HFANB (1:1:1) block copolymer (FIG. 5).
Figure 4:
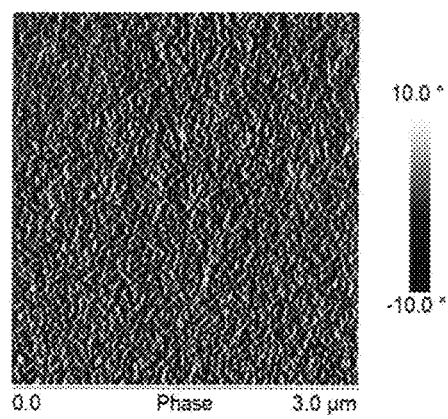
Figure 5:
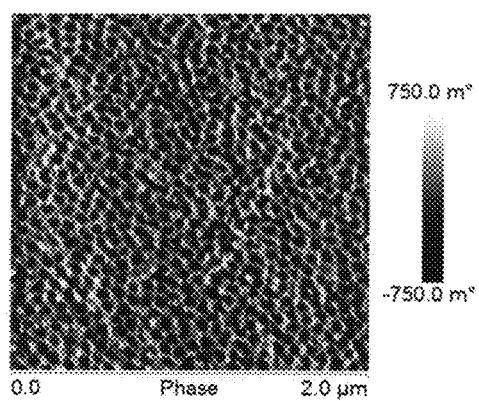

This aspect is illustrated by way of FIGS. 3 and 4, which show respectively atomic force micrographs of the membranes formed from a (1:2) molar ratio of a diblock copolymer of BuNB-HFANB, where the weight fraction of HFANB, $W_{HFANB}$, is 0.78 (FIG. 3) and a (2:1) molar ratio of a diblock copolymer of BuNB-HFANB, where the weight fraction of HFANB, $W_{HFANB}$, is 0.48 (FIG. 4). The membrane containing the (1:2) molar ratio of a diblock copolymer of BuNB-HFANB is formed using toluene as a solvent. The membrane containing the (2:1) molar ratio of a diblock copolymer of BuNB-HFANB is formed using THF as a solvent. It is apparent from FIGS. 3 and 4, these two membranes do not exhibit any nanoscale structure, that is, no observable phase separation of the blocks. Whereas, FIG. 5 shows the atomic force micrograph of the membrane formed from a (1:1:1) molar ratio of a triblock polymer of HFANB-BuNB-HFANB. This membrane is formed using a mixture of toluene and THF. It is quite apparent that the membrane clearly exhibits a nanoscale structure evidencing phase separation. As further described hereinbelow, employing the membrane of FIG. 5 in the pervaporation method of this invention it is now possible to obtain much higher flux than the membranes of FIGS. 3 and 4 (see Table 4). This clearly illustrates at least one of the surprising beneficial effects that can be obtained from the practice of this invention.

The microphase separated morphologies of the membranes can also be obtained by using a mixture of solvents with a modified procedure. Thus in another embodiment of this invention the block polymer of this invention is dissolved in a mixture of non-polar and polar solvents and cast onto a suitable support to form a membrane and the solvent mixture was allowed to evaporate to form the microphase separated morphologies. Examples of non-polar solvents include any of the hydrocarbon solvents such as hexane, heptane, toluene, trifluorotoluene (TFT) and a mixture thereof. Examples of polar solvents include ether solvents such as tetrahydrofuran (THF) and diethyl ether; alcohols such as butanol, pentanol, hexanol or heptanol (or $C_8$-$C_{12}$alcohols), and a mixture thereof. Generally, the membranes are made in this aspect of the invention by a solution casting method as described herein. That is, typically dissolving the block polymer in a mixture of solvents such as, toluene, TFT and THF, coating the solution so formed on a polyacrylonitrile (PAN) membrane, followed by THF vapor annealing. The annealing can be carried out by any of the methods known in the art such as for example exposing the membrane in a THF chamber at a desirable temperature. Generally, the membranes formed in this fashion contain uniform dense layer of the block polymer on a porous PAN supporting membrane and function as a selective layer for pervaporation separation of organic products in aqueous solution such as biobutanol.

The following examples are detailed descriptions of methods of preparation and use of certain compounds/monomers, polymers and compositions of the present invention. The detailed preparations fall within the scope of, and serve to exemplify, the more generally described methods of preparation set forth above. The examples are presented for illustrative purposes only, and are not intended as a restriction on the scope of the invention. As used in the examples and throughout the specification the ratio of monomer to catalyst is based on a mote to mole basis.

EXAMPLES

The following abbreviations have been used hereinbefore and hereafter in describing some of the compounds, instruments and/or methods employed to illustrate certain of the embodiments of this invention:

HFANB: norbornenyl-2-trifluoromethyl-3,3,3-trifluoropropan-2-ol; HexNB: 5-hexylbicyclo-[2.2.1]hept-2-ene; $C_4F_9$NB: 5-perfluorobutylbicyclo[2.2.1]hept-2-ene, BuDM-MINB: 1-(4-(bicyclo[2.2.1]hept-5-en-2-yl)butyl)-3,4-dimethyl-1H-pyrrole-2,5-dione; PGMEA: propylene glycol methyl ether acetate; PTFE: polytetrafluoroethylene; TFT; α,α,α-trifluorotoluene; THF: tetrahydrofuran; R. T.—room temperature.

Reactions generally are run under a nitrogen atmosphere and where needed in a dry-box or with the use of standard Schlenk tube/airless transfer techniques. In general, solvents were dried over molecular sieves or magnesium sulfate or distilled from a drying agent and purged with nitrogen prior to use. Various other known techniques to dry the solvents can also be employed.

The following examples describe the procedures used for the preparation of various compounds as disclosed herein including certain of the starting materials employed in the preparation of the compounds of this invention. However, it should be noted that these examples are intended to illustrate the disclosure without limiting the scope thereof.

Example 1

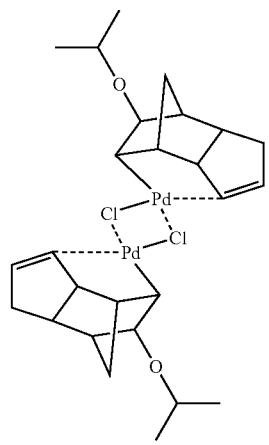

Bis(iso-propoxy-dicyclopentadienyl)dichlorodipalladium [Pd(i-PrO-DCPD)Cl]$_2$ The title compound was prepared using a slightly modified procedure as set forth in Chatt et al., J. Chem. Soc. (1957) 3413 as follows. Under nitrogen atmosphere sodium chloropalladite, [Na$_2$PdCl$_4$], (3 g, 10.2 mmol) was suspended in anhydrous isopropyl alcohol (15 ml) and stirred at ambient temperature. To this suspension was added dicyclopentadiene (2.7 g, 20.4 mmol), and the mixture was continued to stir for 5 days at ambient temperature. The resulting mixture was filtered, washed with heptane (three times with 5 ml), and dried to yield 3.8 g of yellow powder.

Under ambient conditions, 1 g of the yellow powder as obtained above was suspended in heptane (15 ml), isopropyl alcohol (15 ml) was added to this suspension while stirring, and the mixture was continued to stir for 2 days at ambient temperature. The mixture was then filtered, and the solid was washed with heptane to obtain the title compound, yield 1.1 g of white tinged yellow powder. The title compound was found to be essentially pure as characterized by $^1$H NMR: $^1$H NMR (CD$_2$Cl$_2$, δ ppm) 6.46 (1H), 5.88 (1H), 3.72 (2H), 3.18 (1H), 3 (1H), 2.8 (1H), 2.6 (1H), 2.5 (1H), 2.17 (2H), 1.61 (1H), 1.17 (1H), and 1.12 (6H).

Example 2

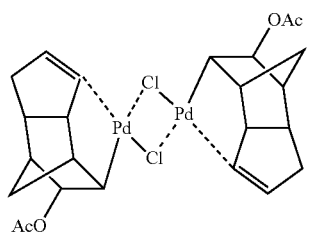

Bis(acetoxy-dicyclopentadienyl)dichlorodipalladium [Pd(AcO-DCPD)Cl]$_2$

Under ambient atmospheric conditions, toluene (20 ml) was added to a mixture of [Pd(DCPD)Cl]$_2$ (0.5 g, 1.6 mmol) and silver acetate (AgOAc) (0.27 g, 1.6 mmol) while stirring. The resulting yellow suspension was allowed to stir for 1 hour at ambient temperature. The resulting brown-colored solution was filtered, and the filtrate was evaporated to dryness to afford orange-colored oil, which was washed with 30 ml of ether, and filtered to obtain yellowish pink colored title compound. The title compound was found to be essentially pure as characterized by $^1$H NMR: $^1$H NMR (CD$_2$Cl$_2$, δ ppm), 6.51 (1H), 5.93 (1H), 4.87 (1H), 3.1 (2H), 2.85 (1H), 2.68 (3H), 2.33 (1H), 2.22 (2H), and 1.96 (3H).

Example 3

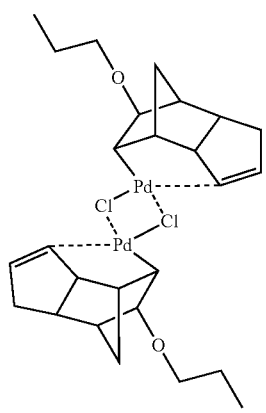

Bis(n-propoxy-dicyclopentadienyl)dichlorodipalladium [Pd(n-PrO-DCPD)Cl]$_2$

Under nitrogen atmosphere, n-propanol (25 ml) was added via cannula to a solid mixture of [Na$_2$PdCl$_4$] (1 g, 3.4 mmol) and dicyclopentadiene (0.9 g, 6.8 mmol) while stirring. The resulting reddish brown suspension was allowed to stir for one day at ambient temperature. The resulting pate beige-colored suspension was filtered, washed three times with hexane (5 ml each time) and dried under vacuum to obtain the title compound, yield, 1.5 g. The title compound was found to be essentially pure as characterized by $^1$H NMR: $^1$H NMR (CD$_2$Cl$_2$, δ ppm), 6.48 (1H), 5.87 (1H), 3.59 (1H), 3.45 (1H), 3.3 (1H), 3.21 (1H), 3.02 (1H), 2.83 (1H), 2.63 (1H), 2.56 (1H), 2.25 (1H), 2.18 (1H), 1.6 (1H), 1.58 (4H), 1.06 (1H), 0.88 (3H).

Example 4

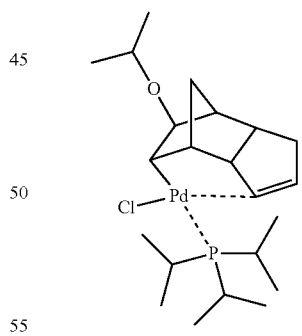

(iso-propoxy-dicyclopentadienyl)chloropalladium (triisopropyl)phosphine [Pd(i-PrO-DCPD)Cl(P-i-Pr$_3$)]

Under nitrogen atmosphere, the compound of Example 1, [Pd(i-PrO-DCPD)Cl]$_2$, (1 g, 1.5 mmol), was suspended in tetrahydrofuran (30 ml) and allowed to stir. To this suspension was added dropwise via cannula a solution of triisopropylphosphine (0.48 g, 3 mmol) in tetrahydrofuran (10 ml). At completion of this addition the suspension became clear and the solution was stirred for additional 15 min, it was then concentrated to 10 ml and filtered. The resulting yellow-colored filtrate was stirred for overnight and concentrated to dryness to obtain 1.25 g of the title compound as yellow-colored solid. The title compound was found to be essentially pure as characterized by $^1$H NMR and $^{31}$P NMR: $^1$H NMR (toluene-$d_8$, δ ppm), 7.59 (1H), 7.15 (1H), 3.71 (1H), 3.47 (1H), 2.76 (1H), 2.53 (4H), 2.28 (2H), 2.1 (2H), 1.81 (1H), 1.63 (1H), 1.4 (1H), 1.24 (18H), 1.05 (6H); $^{31}$P NMR (toluene-$d_8$, δ ppm) 50.93.

Example 5

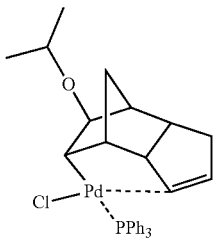

(iso-propoxy-dicyclopentadienyl)chloropalladium (triphenylphosphine) [Pd(i-PrO-DCPD)Cl(PPh$_3$)]

Under nitrogen atmosphere, light petroleum ether (230 ml) was added to a mixture of Example 1, [Pd(i-PrO-DCPD)Cl]$_2$, (3 g, 4.5 mmol) and triphenylphosphine (2.6 g, 9.9 mmol). The resulting brown suspension was stirred for 24 hours at ambient temperature, filtered, washed with ether, and then dried to obtain 4.1 g of the title compound as a brown powder. The title compound was found to be essentially pure as characterized by $^1$H NMR and $^{31}$P NMR: $^1$H NMR (CD$_2$Cl$_2$, δ ppm), 7.67 (6H), 7.48 (9H), 6.89 (1H), 3.88 (1H), 3.33 (1H), 2.93 (1H), 2.83 (1H), 2.67 (2H), 2.33 (1H), 2.21 (1H), 1.92 (1H), 1.54 (1H), 1.27 (1H), 1.09 (1H), 0.99 (3H), 0.79 (3H); $^{31}$P NMR (CD$_2$Cl$_2$, δ ppm) 30.76.

Example 6

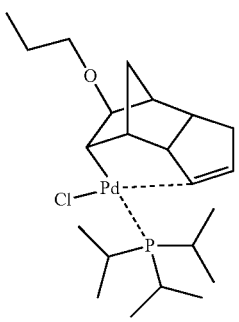

(n-propoxy-dicyclopentadienyl)chloropalladium(tri-isopropyl)phosphine [Pd(n-PrO-DCPD)Cl(P-i-Pr$_3$)]

Under nitrogen atmosphere, the compound of Example 3, [Pd(n-PrO-DCPD)Cl]$_2$, (0.5 g, 1.5 mmol), was suspended in tetrahydrofuran (15 ml) and allowed to stir. To this suspension was added dropwise via cannula a solution of triisopropylphosphine (0.24 g, 1.5 mmol) in tetrahydrofuran (5 ml). At completion of this addition the suspension became clear and the solution was stirred overnight and filtered using 0.45 mm polytetrafluoroethylene (PTFE) syringe filter. The filtrate was concentrated to dryness to afford yellow-colored oil, which was taken up in petroleum ether (3 ml), and sonicated for 3 minutes to precipitate the title compound as a solid. The title compound was then filtered and dried under vacuum, yield 0.26 g. The title compound was found to be essentially pure as characterized by $^1$H NMR and $^{31}$P NMR: $^1$H NMR (CD$_2$Cl$_2$, δ ppm), 7.05 (1H), 6.78 (1H), 3.61 (1H), 3.36 (1H), 3.18 (1H), 2.89 (2H), 2.64 (5H), 2.35 (1H), 2.24 (1H), 2.09 (1H), 1.55 (4H), 1.47 (3H), 1.34 (18H); $^{31}$P NMR (CD$_2$Cl$_2$, δ ppm) 50.16.

Example 7

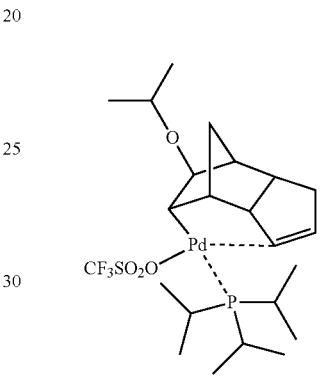

(iso-propoxy-dicyclopentadienyl)(triisopropyl)phosphinepalladium triflate [Pd(i-PrO-DCPD)(P-i-Pr$_3$)(OTf)]

In a dry box under inert atmosphere of nitrogen, the compound of Example 4, [Pd(i-PrO-DCPD)Cl(P-i-Pr$_3$)] (0.25 g, 0.5 mmol) was dissolved in dichloromethane (3 ml) and allowed to stir. To this stirred solution was added a suspension of silver triflate, AgOTf, (0.13 mg, 5 mmol) in dichloromethane (2 ml) followed by tetrahydrofuran (2 ml), which resulted in a milky pale yellow suspension. The mixture was stirred for 10 minutes and filtered through 0.45 mm polytetrafluoroethylene (PTFE) syringe filter. The yellow filtrate thus obtained was concentrated to dryness to afford oily residue, which was dissolved in diethyl ether (2 ml), and was dried in vacuum to obtain 0.14 g of the title compound as a beige-white foamy solid. The title compound was found to be essentially pure as characterized by $^1$H, $^{31}$P and $^{19}$F NMR: $^1$H NMR (toluene-$d_8$, δ ppm), 7.3 (1H), 6.8 (1H), 3.55 (1H), 3.41 (1H), 2.62 (1H), 2.45 (1H), 2.27 (6H), 2.03 (1H), 1.8 (1H), 1.5 (1H), 1.16 (9H), 1.06 (9H), 0.98 (6H), 0.86 (1H); $^{31}$P NMR (toluene-$d_8$, δ ppm), 50; $^{19}$F NMR (toluene-$d_8$, δ ppm), −77.3.

Example 8

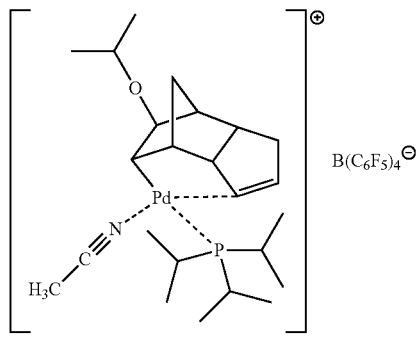

(iso-propoxy-dicyclopentadienyl)(triisopropyl)phosphine(acetonitrile)palladium tetrakis(pentafluorophenyl)borate [Pd(i-PrO-DCPD)(P-i-Pr$_3$)(CH$_3$CN)]FABA Under nitrogen atmosphere, the compound of Example 4, [Pd(i-PrO-DCPD)Cl(P-i-Pr$_3$)](5.1 g, 10.2 mmol) was dissolved in toluene (25 ml) while stirring. To this solution was added via cannula a solution of lithium tetrakis(pentafluorophenyl)borate (LiFABA) (8.92 g, 10.2 mmol) in acetonitrile (25 ml). The clear yellow solution became cloudy, and was left to stir overnight and filtered through celite. The filtrate was concentrated to afford thick slurry mass. To this slurry mass was added pentane (50 ml) and ether (50 ml) to afford a yellow solid, which was filtered, washed with pentane (25 ml) and dried in vacuum to obtain 9.9 g (82% yield) of the title compound. The title compound was found to be essentially pure as characterized by $^1$H and $^{31}$P NMR: $^1$H NMR (acetone-d$_6$, δ ppm), 7.17 (1H), 6.76 (1H), 3.85 (1H), 3.72 (1H), 3.5 (2H), 2.94 (2H), 2.7 (5H), 2.4 (1H), 2.32 (2H), 2.1 (1H), 1.56 (1H), 1.42 (18H), 1.18 (1H), 1.09 (6H); $^{31}$P NMR (acetone-d$_6$, δ ppm), 52.19.

Example 9

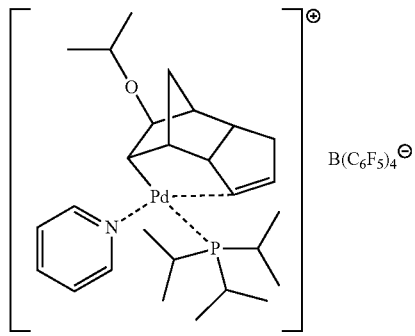

(iso-propoxy-dicyclopentadienyl)(triisopropyl)phosphine(pyridine)palladium tetrakis(pentafluorophenyl)borate [Pd(i-PrO-DCPD)(P-i-Pr$_3$)(p)]FABA Under nitrogen atmosphere, the compound of Example 8, [Pd(i-PrO-DCPD)(P-i-Pr$_3$)(CH$_3$CN)]FABA (0.25 g, 0.212 mmol) was dissolved in toluene (5 ml) and allowed to stir. To this solution was added pyridine (90 ml) via syringe, which resulted in pale yellow solution. The solution was concentrated to dryness to afford yellow oil, which was dissolved in diethyl ether (1 ml) and evaporated to dryness to obtain 0.18 g of the title compound as a white foamy solid. The title compound was found to be essentially pure as characterized by $^1$H and $^{31}$P NMR: $^1$H NMR (CD$_2$Cl$_2$, δ ppm), 8.54 (2H), 7.92 (1H), 7.54 (2H), 7.08 (1H), 5.41 (1H), 3.82 (1H), 3.72 (1H), 3.06 (2H), 2.75 (1H), 2.65 (1H), 2.46 (1H), 2.34 (6H), 1.65 (1H), 1.39 (18H), 1.18 (6H); $^{31}$P NMR (CD$_2$Cl$_2$, δ ppm), 50.35.

Example 10

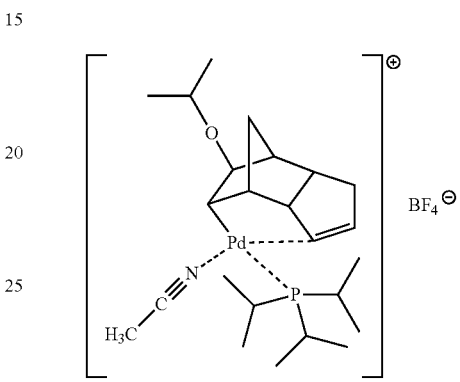

(iso-propoxy-dicyclopentadienyl)(triisopropyl)phosphine(acetonitrile)palladium tetrafluoroborate [Pd(i-PrO-DCPD)(P-i-Pr$_3$)(CH$_3$CN)]BF$_4$ In a dry box under inert atmosphere of nitrogen, the compound of Example 4, [Pd(i-PrO-DCPD)Cl(P-i-Pr$_3$)] (1 g, 2 mmol), was suspended in toluene (10 ml) under stirring. To this suspension was added via a pipet solution of silver tetrafluoroborate, AgBF$_4$, (0.4 g, 2 mmol) in acetonitrile (5 ml). The suspension was cleared quickly and grey solid was precipitated, the stirring was continued for 5 minutes, then filtered through 0.45 mm polytetrafluoroethylene (PTFE) syringe filter. The filtrate was concentrated to dryness to afford yellow oily residue, which was washed twice with pentane (5 ml), then taken up in diethyl ether (5 ml). The resulting solution was concentrated to dryness to obtain 820 mg of the title compound as pale pearl colored foamy solid. The title compound was found to be essentially pure as characterized by $^1$H NMR and $^{31}$P NMR: $^1$H NMR (CDCl$_3$, δ ppm), 7.21 (1H), 6.51 (1H), 3.77 (1H), 3.67 (1H), 2.96 (2H), 2.71 (1H), 2.46 (7H), 2.21 (2H), 1.58 (26H); $^{31}$P NMR (CD$_2$Cl$_2$, δ ppm), 52.49.

Example 11

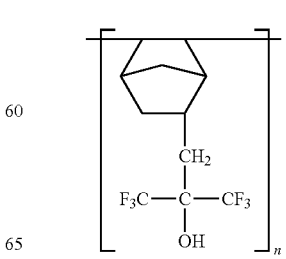

Homopolymer of norbornenyl-2-trifluoromethyl-3,3,3-trifluoropropan-2-ol (HFANB)

Example 11 illustrates high catalytic activity of the compounds of this invention when compared with palladium catalysts reported in the literature, a few of the comparative examples are provided below as Comparative Example 1 and Comparative Example 2, all of which were carried out essentially under same conditions to show the differences in the respective catalytic activity of the compounds employed therein.

Into a suitable reaction vessel were placed HFANB (1 g, 3.7 mmol) and toluene (3 g), sparged with nitrogen for 30 min, then heated to 80° C. To this solution was added a solution of the compound of Example 8 (0.022 g, 0.018 mmol) in toluene (1 ml). The mixture was stirred for 30 minutes then cooled to room temperature. The polymerization was stopped by adding a solution of ((phenylphosphanediyl)bis(ethane-2,1-diyl))bis(diphenylphosphane), triphos (0.04 g, 0.06 mmol) in dichloromethane (0.3 ml). Then the polymer was precipitated by pouring the mixture into an excess of ethanol (10 mL) to obtain 1 g of polymer (100% conversion). The polymer was characterized by GPC: $M_w$=60,600; $M_n$=16,700; PDI=3.6.

Examples 12-15

Homopolymerization with Compound of Example 4

Example 11 was substantially repeated in these Examples 12 to 15 except that various different monomers as listed in Table 1 were employed with the compound of Example 4 as the polymerization catalyst along with lithium tetrakis(pentafluoroborate), LiFABA at a 100:1:1 molar ratio of monomer:catalyst:LiFABA. At the end of the indicated reaction time the reaction was stopped and the solvent was evaporated. The residual mass was dissolved in THF and filtered. The polymer was then precipitated by pouring the polymer solution onto water or acetone. The powdery polymer thus obtained was then collected and precipitated twice again by dissolving in THF and pouring the solution to water or acetone.

The monomer used in each of these Examples 12 to 15, the solvent employed, temperature of the polymerization reaction, reaction time, conversion and the GPC data of the resulting polymer are summarized in Table 1.

TABLE 1

| Example No. | Monomer | Solvent | Temp (° C.) | Time (min) | Conv. (%) | $M_n$ | PDI |
|---|---|---|---|---|---|---|---|
| 12 | HexNB | Toluene | R.T | 4 | 99 | 100,000 | 1.4 |
| 13 | HFANB | TFT/Toluene (50/50) | R.T. | 60 | 88 | 49,000 | 1.2 |
| 14 | $C_4F_9$NB | TFT | 45 | 90 | 100 | 148,000 | 1.2 |
| 15 | BuDMMINB | TFT | 45 | 20 h | 36 | 7,000 | 1.5 |

R.T.—room temperature;
TFT—trifluorotoluene;

Examples 15A-E

The following Examples 15A-E provide procedures to make a variety of to methyl(palladium)phosphine compounds used to make living polymers of this invention.

Example 15A

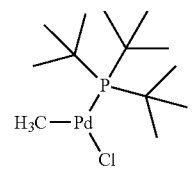

$(CH_3)Pd(P^tBu_3)(Cl)$

The title compound was prepared using a slightly modified procedure as set forth in K. Nozaki et al., Organometallics. 2006, 4588. Under nitrogen atmosphere [(1,5-cyclooctadiene)Pd(CH_3)(Cl)] (2.5 g, 9.43 mmol) was dissolved in anhydrous methylene chloride (2.5 ml) and stirred at −78° C. To this solution was added tri-tert-butyl phosphine (1.91 g, 9.43 mol) in methylene chloride solution (2 mL), and the mixture was continued to stir for 5 minutes at −78° C. Then the mixture solution was allowed to warm up to ambient temperature and continued to stir for 15 min. The resulting mixture was filtered, washed with n-pentane (three times with 10 ml), and dried to yield 2.73 g of title compound as yellow powder.

The title compound was found to be essentially pure as characterized by $^1$H NMR and $^{31}$P-NMR: $^1$H NMR (CD$_2$Cl$_2$, δ ppm) 1.75 (s, 3H), 1.52 (d, 12 Hz, 27H), 31P-NMR CD$_2$Cl$_2$, δ ppm) 69.5

Example 15B

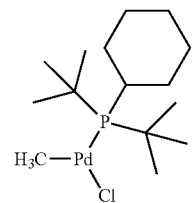

$(CH_3)Pd(P(^tBu)_2(Cy))(Cl)$

The procedures of Example 15A was substantially followed except for using [(1,5-cyclooctadiene)Pd(CH$_3$)(Cl)] (300 mg, 1.1 mmol) and di-tert-butyl-cyclohexyl phosphine (260 mg, 1.1 mmol) to yield 280 mg of title compound as a pale yellow powder.

The title compound was found to be essentially pure as characterized by $^1$H NMR and $^{31}$P-NMR: $^1$H NMR (CD$_2$Cl$_2$, δ ppm) 2.35 (m, 2H), 1.75 (m, 5H), 1.52 (m, 18H), 1.30 (m, 4H), 0.82 (s, 3H), $^{31}$P-NMR (CD$_2$C$_2$, δ ppm) 71.5

Example 15C

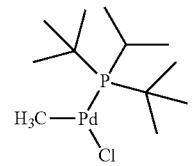

(CH₃)Pd(P(ᵗBu)₂(ⁱPr))(Cl)

The procedures of Example 15A was substantially followed except for using [(1,5-cyclooctadiene)Pd(CH₃)(Cl)] (430 mg, 1.62 mmol) and di-tert-butyl-iso-propyl phosphine (320 mg, 1.7 mmol) to yield 380 mg of the title compound as pale yellow powder.

The title compound was found to be essentially pure as characterized by ¹H NMR and ³¹P-NMR: ¹H NMR (CDCl₃, δ ppm) 2.8 (m, 1H), 1.54 (m, 24H) 0.79 (s, 3H). ³¹P-NMR (CDCl₃, δ ppm) 71.5.

Example 15D

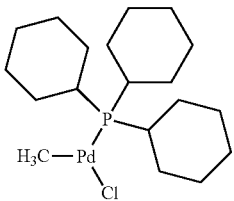

(CH₃)Pd(P(Cy)₃)(Cl)

The procedures of Example 15A was substantially followed except for using [(1,5-cyclooctadiene)Pd(CH₃)(Cl)] (600 mg, 2.3 mmol) and tri-cyclohexyl phosphine (630 mg, 2.3 mmol) to yield 350 mg of the title compound as pale yellow powder.

The title compound was found to be essentially pure as characterized by ¹H NMR and ³¹P-NMR: ¹H NMR (CDCl₃, δ ppm) 1.8 (m, 23H), 1.32 (m, 10H), 0.79 (s, 3H). ³¹P-NMR (CDCl₃, δ ppm) 47.

Example 15E

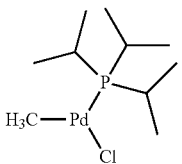

CH₃)Pd(P(ⁱPr)₃)(Cl)

The procedures of Example 15A was substantially followed except for using [(1,5-cyclooctadiene)Pd(CH₃)(Cl)] (210 mg, 0.8 mmol) and tri-isopropyl phosphine (130 mg, 0.8 mmol) to yield 180 mg of the title compound as pale yellow powder.

The title compound was found to be essentially pure as characterized by ¹H NMR and ³¹P-NMR: ¹H NMR (CD₂Cl₂, δ ppm) 2.40 (m, 3H), 1.42 (m, 18H) 0.72 (s, 3H). ³¹P-NMR (CD₂Cl₂, δ ppm, 50° C.) 56.6.

Example 15F

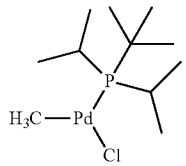

CH₃)Pd(P(ⁱPr)₂(ᵗBu))(Cl)

The procedures of Example 15A was substantially followed except for using [(1,5-cyclooctadiene)Pd(CH₃)(Cl)] (500 mg, 1.9 mmol) and di-isopropyl-tert-butyl phosphine (330 mg, 1.9 mmol) to yield 510 mg of the title compound as pale yellow powder.

The title compound was found to be essentially pure as characterized by ¹H NMR and ³¹P-NMR: ¹H NMR (CD₂Cl₂, δ ppm) 2.55 (m, 2H), 1.52 (m, 21H) 0.80 (s, 3H). ³¹P-NMR (CD₂Cl₂, δ ppm, RT) 66.5.

Examples 15AA-AI

The following Examples 15AA-AI provide procedures to make a variety of allyl(palladium)phosphine and imidazole compounds used to make living polymers of this invention.

Example 15AA

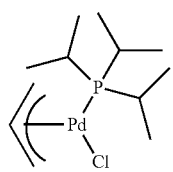

(η³-allyl)Pd(P(ⁱPr)₃)(Cl)

Under nitrogen atmosphere [(η³-allyl)Pd(Cl)]₂ (4 g, 10.9 mmol) was dissolved in anhydrous toluene (100 ml) and stirred at −78° C. To this solution was added tri-iso-propyl phosphine (3.68 g, 23 mmol) in toluene solution (50 mL), and the mixture was continued to stir for 5 minutes at −78° C. Then the mixture was allowed to warm up to ambient temperature and continued to stir for 2 days. The resulting mixture was evaporated to dryness, and the resulting solid was dissolved by THF (48 ml). After stirring for 5 hr, the solution was filtered to remove any metal and then evaporated to dryness. The resulting solid was washed with diethyl ether (three times with 20 ml), and dried to yield 5.7 g of title compound as pale-yellow powder.

The title compound was found to be essentially pure as characterized by ¹H NMR and ³¹P-NMR: ¹H NMR (CDCl₃, δ ppm) 5.42 (m, 1H), 4.73 (m, 1H), 3.75 (m, 1H), 3.62 (m, 1H), 2.75 (m, 1H), 2.53 (m, 3H), 1.30 (m, 18H). ³¹P-NMR (CDCl₃, δ ppm) 53.

Example 15AB

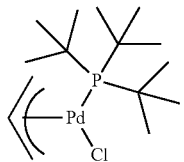

(η³-allyl)Pd(P(ᵗBu)₃)(Cl)

The procedures of Example 15AA was substantially followed except for using tri-tert-butylphosphine (420 mg, 2.08 mmol) in toluene solution (15 mL) to yield 310 mg of the title compound as a yellow powder.

The title compound was found to be essentially pure as characterized by $^1$H NMR and $^{31}$P-NMR: $^1$H NMR (CD₂Cl₂, δ ppm) 5.48 (m, 1H), 4.65 (m, 1H), 4.23 (m, 1H), 3.78 (m, 1H), 2.75 (m, 1H), 1.60 (m, 27H). $^{31}$P-NMR (CD₂Cl₂, δ ppm) 88.

Example 15AC

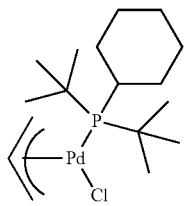

(η³-allyl)Pd(P(Cy)(ᵗBu)₂)(Cl)

The procedures of Example 15AA was substantially followed except for using Di-tert-butyl cyclohexyl phosphine (620 mg, 2.73 mmol) in toluene solution (15 mL) to yield 350 mg of the title compound as a pale-yellow powder.

The title compound was found to be essentially pure as characterized by $^1$H NMR and $^{31}$P-NMR. $^1$H NMR (CD₂Cl₂, δ ppm) 5.48 (m, 1H), 4.65 (m, 1H), 4.23 (m, 1H), 3.78 (m, 1H), 2.75 (m, 1H), 1.80-1.40 (m, 29H). $^{31}$P-NMR (CD₂Cl₂, δ ppm) 72.

Example 15AD

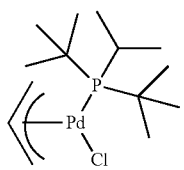

(η³-allyl)Pd(P(ⁱPr)(ᵗBu)₂)(Cl)

The procedures of Example 15AA was substantially followed except for using di-tert-butyl-isopropyl phosphine (510 mg, 2.73 mmol) in toluene solution (10 mL) to yield 480 mg of the title compound as a pate-yellow powder.

The title compound was found to be essentially pure as characterized by $^1$H NMR and $^{31}$P-NMR: $^1$H NMR (CDCl₃, δ ppm) 5.40 (m, 1H), 4.73 (m, 1H), 3.82 (m, 1H), 3.70 (m, 1H), 3.25 (m, 1H), 2.75 (m, 1H), 1.63 (m, 24H). $^{31}$P-NMR (CDCl₃, δ ppm) 71.8.

Example 15AE

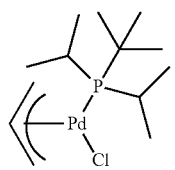

(η³-allyl)Pd(P(ⁱPr)₂(ᵗBu))(Cl)

The procedures of Example 15AE was substantially followed except for using tert-butyl-diisopropyl phosphine (480 mg, 233 mmol) in toluene solution (10 mL) to yield 490 mg of the title compound as a pale-yellow powder.

The title compound was found to be essentially pure as characterized by $^1$H NMR and $^{31}$P-NMR: $^1$H NMR (CDCl₃, δ ppm) 5.40 (m, 1H), 4.73 (m, 1H), 3.82 (m, 1H), 3.70 (m, 1H), 3.25 (m, 1H), 2.75 (m, 3H), 1.45 (m, 21H). $^{31}$P-NMR (CDCl₃, δ ppm) 63.2.

The following palladium compounds were purchased from Johnson Matthey and used as such:

Example 15AF

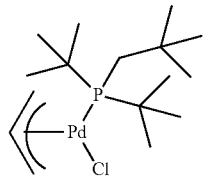

Example 15AG

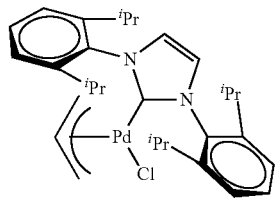

Example 15AH

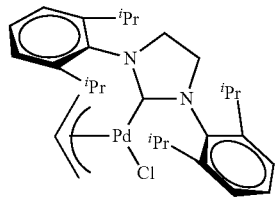

Example 15AI

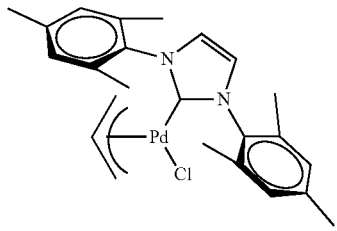

Examples 16B-16R

Homo-Polymerization of Functionalized Norbornenes using Compounds of Example 15A-15E The homo polymerization with various norbornene monomers and palladium compounds of Examples 15A through 15E were carried out using substantially the same procedures as set forth in Example 16A. The norbornenes used in each of these Examples 16B-16R, the solvent employed, reaction time, conversion and the GPC data of the resulting polymer are summarized Table 1A. In each of these Examples the molar ratio of Pd compound, LiFABA, norbornene monomer was Pd compound/LiFABA/NB monomer=1/1/100.

TABLE 1A

| Example No. | Pd Compound No. | Monomer | Solvent | Temp. [° C.] | Time [min] | Conv. | $M_n$ | PDI |
|---|---|---|---|---|---|---|---|---|
| 16B | 15A | NBANB | Toluene | RT | 1440 | 1 | 2,700 | 1.4 |
| 16C | 15A | HFANB | Toluene/TFT | RT | 1080 | 63 | 11,000 | 1.4 |
| 16D | 15A | HFANB | Toluene/Ethylacetate | RT | 1440 | 0 | — | — |
| 16E | 15B | BuNB | Toluene | RT | 10 | 100 | 29,000 | 1.5 |
| 16F | 15B | NBANB | Toluene | RT | 1440 | 81 | 17,000 | 1.3 |
| 16G | 15B | HFANB | Toluene/TFT | RT | 240 | 67 | 15,000 | 1.4 |
| 16H | 15B | EPEsNB | Toluene | RT | 1440 | 50 | 15,000 | 1.3 |
| 16I | 15C | BuNB | Toluene | RT | 10 | 100 | 39,000 | 1.4 |
| 16J | 15C | NBANB | Toluene | RT | 1440 | 84 | 13,000 | 1.4 |
| 16K | 15C | HFANB | Toluene/TFT | RT | 1440 | 100 | 20,000 | 1.3 |
| 16L | 15D | BuNB | Toluene | RT | 20 | 19 | 15,000 | 1.9 |
| 16M | 15D | NBANB | Toluene | RT | 1440 | 85 | 19,000 | 1.5 |
| 16N | 15E | BuNB | Toluene | RT | 20 | 11 | 245,000 | 1.1 |
| 16O | 15E | NBANB | Toluene | RT | 10 | 19 | 107,700 | 1.1 |
| 16P | 15E | NBANB | Toluene | RT | 240 | 100 | Insoluble | — |
| 16Q | 15E | HFANB | Toluene/TFT | RT | 1080 | 13 | 15,000 | 1.2 |
| 16R | 15F | NBANB | Toluene | RT | 360 | 100 | Insoluble | — |
| 16S | 15F | HFANB | Toluene/TFT | RT | 2880 | 98 | 79,000 | 1.4 |

Example 16A

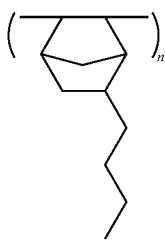

Homopolymer of 5-butyl-2-norbornene (BuNB)

Into a suitable reaction vessel were placed BuNB (1.2 g, 7.98 mmol), toluene (22.32 g) and α,α,α-trifluorotoluene (TFT) (0.48 g) purged with nitrogen. To this solution was added a solution of the compound of Example 15A (30 mg, 0.79 mmol) and lithium tetrakis (pentafluoroborate), LiFABA (70 mg, 0.79 mmol). After polymerization 20 min, the reaction solution was sampled and deactivated by toluene/CH$_3$CN solution. The polymer was characterized by GPC: $M_w$=34,509; $M_n$=30,752; PDI=1.1.

Example 16AA

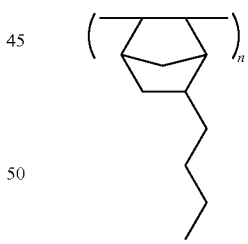

Homopolymer of 5-butyl-2-norbornene (BuNB)

Into a suitable reaction vessel were placed BuNB (1.2 g, 7.98 mmol), toluene (22.32 g) and α,α,α-trifluorotoluene (TFT) (0.48 g) purged with nitrogen. To this solution was added a solution of the compound of Example 15AA (31 mg, 0.079 mmol) and lithium tetrakis (pentafluoroborate), LiFABA (70 mg, 0.079 mmol). After 20 min, the reaction solution was sampled and deactivated by toluene/CH$_3$CN solution. The polymer was isolated and characterized by GPC: $M_w$=25,239, $M_n$=22,243, PDI=1.1.

Examples 16AB-AS
Homo-Polymerization with Compounds of Examples 15AA-AI

The homo polymerization with various norbornene monomers and palladium compounds of Examples 15AA through 15AI were carried out using substantially the same procedures as set forth in Example 16A. The norbornenes used in each of these Examples 16AB-16AS, the solvent employed, reaction time, conversion and the GPC data of the resulting polymer are summarized in Table 1B. In each of these Examples the molar ratio of Pd compound, LiFABA, norbornene monomer (Pd compound/LiFABA/NB monomer)=1/1/100.

Table 2 were employed to form the diblock polymers. In all of these Examples, the first monomer was polymerized and then to the resulting polymeric, mixture the second monomer was added to obtain the diblock polymers. The polymerization catalyst used in these Examples 16 to 20 was allylpalladium(triisopropylphosphine)chloride, [Pd(allyl)(triisopropylphosphine)Cl] along with lithium tetrakis(pentafluoroborate), LiFABA at a 100:100:1:1 molar ratio of monomer 1:monomer 2:catalyst:LiFABA, except that the molar ratio of monomer 1:monomer 2:catalyst:LiFABA in Example 19 was 250:250:1:1. The solvent employed in each

TABLE 1B

| Example No. | Pd Compound No. | Monomer | Solvent | Temp. °C. | Time [min] | Conv. | $M_n$ | PDI |
|---|---|---|---|---|---|---|---|---|
| 16AB | Ex. 15AA | NBANB | Toluene | RT | 30 | 100 | Insoluble | — |
| 16AC | Ex. 15AA | HFANB | Toluene/TFT | RT | 120 | 100 | 33,000 | 1.2 |
| 16AD | Ex. 15AA | EPEsNB | Toluene | RT | 1440 | 50 | 10,000 | 1.3 |
| 16AE | Ex. 15AA | EPEsNB | Toluene | 60 | 1440 | 44 | 7,700 | 1.4 |
| 16AF | Ex. 15AB | BuNB | Toluene | RT | 30 | 100 | 25,000 | 1.1 |
| 16AG | Ex. 15AB | NBANB | Toluene | RT | 990 | 1 | 4,500 | 1.4 |
| 16AH | Ex. 15AC | NBANB | Toluene | RT | 1260 | 89 | 14,000 | 1.6 |
| 16AI | Ex. 15AC | HFANB | Toluene/TFT | RT | 2880 | 89 | 27,500 | 1.2 |
| 16AJ | Ex. 15AD | BuNB | Toluene | RT | 7 | 100 | 22,000 | 1.3 |
| 16AK | Ex. 13AD | NBANB | Toluene | RT | 1440 | 89 | 15,500 | 1.3 |
| 16AL | Ex. 15AE | BuNB | Toluene | RT | 3 | 100 | 33,000 | 1.5 |
| 16AM | Ex. 15AE | NBANB | Toluene | RT | 120 | 100 | 16,000 | 1.6 |
| 16AN | Ex. 15AF | NBANB | Toluene | RT | 900 | ND | ND | — |
| 16AO | Ex. 15AG | BuNB | Toluene | RT | 15 | 49 | 18,600 | 1.2 |
| 16AP | Ex. 15AG | BuNB | Toluene | RT | 60 | 100 | Insoluble | — |
| 16AQ | Ex. 15AH | BuNB | Toluene | RT | 300 | 93 | 18.000 | 1.3 |
| 16AR | Ex. 15AI | BuNB | Toluene | RT | 1 | 17 | 35,000 | 1.3 |
| 16AS | Ex. 15AI | BuNB | Toluene | RT | 3 | 100 | Insoluble | — |

ND = not determined

From the above data it is very clear that allyl(palladium)phosphine compounds of Examples 15AA-AI generally exhibit higher reactivity and more living-like characteristic than the corresponding methyl(palladium)phosphine compounds of Examples 15AE as summarized above in Table 1A and Table 1B.

Examples 16-20
Diblock Polymers

Example 11 was substantially repeated in these Examples 16 to 20 except that various different monomers as listed in of these Examples was toluene except in Example 20, a 50:50 (v/v) mixture of toluene and trifluorotoluene was used, and the polymerization was carried out at room temperature. The resulting residual mass was reprecipitated by dissolving in THF, filtering the solution and reprecipitating in water or acetone as described in Examples 12-15.

The monomers used in each of these Examples 16 to 20, the monomer ratio in the resulting polymer, reaction time, conversion and the GPC data of the resulting polymer are summarized in Table 2.

TABLE 2

| | | | Polymerization 1$^{st}$ | | | | Polymerization 2$^{nd}$ | | | |
|---|---|---|---|---|---|---|---|---|---|---|
| Ex. No. | Polymer | Monomer Ratio | Time (min) | Conv. (%) | $M_n$ | PDI | Time (min) | Conv. (%) | Mn | PDI |
| 16 | HexN13-b-HexNB | 100/100 | 12 | 94 | 40,200 | n.m. | 15 | 97 | 62,500 | 1.1 |
| 17 | BuNB-b-BuNB | 100/100 | 9 | 96 | 32,000 | 1.1 | 16 | 100 | 60,000 | 1.1 |
| 18 | BuNB-b-HFANB | 100/100 | 8 | 87 | 26,000 | 1.2 | 60 | 100 | 68,000 | 1.1 |
| 19 | BuNB-b-HFANB | 250/250 | 17 | 97 | 76,000 | 1.1 | 70 | 88 | 138,000 | 1.1 |
| 20 | HFANB-b-NBANB | 100/100 | 65 | 93 | 45,000 | 1.3 | 60 | 100 | 63,000* | 1.1 |

*the polymer precipitated from reaction solution;
n.m.—not measured

Examples 21-24

Diblock Polymers

Example 11 was substantially repeated in these Examples 21 to 24 except that various different monomers as listed in Table 3 were employed to form the diblock polymers. In all of these Examples, the first monomer was polymerized and then to the resulting polymeric mixture the second monomer was added to obtain the diblock polymers. The polymerization catalyst used in these Examples 21 to 24 was methylpalladium(triisopropylphosphine)chloride, [Pd(methyl)(tri-tert-butylphosphine)Cl] along with lithium tetrakis(pentafluoroborate), LiFABA, at a 100:100:1:1 molar ratio of monomer 1:monomer 2:catalyst:LiFABA, except that the molar ratio of monomer 1:monomer 2:catalyst:LiFABA in Example 23 was 500:500:1:1, The solvent employed in each of these Examples was toluene except in Example 24 trifluorotoluene was used, and the polymerization was carried out at room temperature except in Example 24 the polymerization was carried out at 45° C. As in Examples 12-15, at the end of the indicated reaction time the polymerization reaction was stopped and the polymer was isolated by evaporating the solvent. The resulting residual mass was reprecipitated by dissolving in THF, filtering the solution and reprecipitating in water or acetone as described in Examples 12-15.

The monomers used in each of these Examples 21 to 24, the monomer ratio in the resulting polymer, time, conversion and the GPC data of the resulting polymer are summarized in Table 3.

the polymer isolated following substantially the procedures as set forth in Examples 12-15. The resulting diblock polymer, HFANB-b-BuNB, exhibited $M_n$ of 102,000 with a PDI of 1.2 by GPC.

Example 26

Triblock Polymer-BuNB-b-HFANB-b-BuNB (1:1:1 Block Ratio)

Example 11 was substantially repeated in this Example 26 except that BuNB and HFANB monomers were used to form the title triblock polymer. The first monomer 1, BuNB was polymerized first, then to the resulting polymeric mixture the monomer 2, HFANB, was added to form the diblock polymer, and in the final step, monomer 3, BuNB was added to form the title triblock polymer. The polymerization catalyst used in this Example 26 was allylpalladium(triisopropylphosphine)chloride, [Pd(allyl)(triisopropylphosphine)Cl] along with tetrakis(pentafluoroborate), LiFABA at a 100:100:100:1:1 molar ratio of monomer 1:monomer 2:monomer 3:catalyst:LiFABA. The solvent employed was toluene, and the polymerization was carried out at room temperature. The first polymerization with BuNB was carried out for 9 minutes, 97% conversion, $M_n$=35,000, PDI 1.1; second polymerization with HFANB was carried out for 60 minutes, 95% conversion, $M_n$=80,000, PD 1.1; and final polymerization with BuNB was carried out for 3 minutes, 97% conversion, $M_n$=108,000, PDI 1.2.

TABLE 3

| Example No. | Polymer | Monomer Ratio | Polymerization 1st | | | | Polymerization 2nd | | | |
|---|---|---|---|---|---|---|---|---|---|---|
| | | | Time (min) | Conv. (%) | $M_n$ | PDI | Time (min) | Conv. (%) | Mn | PDI |
| 21 | HexNB-b-HexNB | 100/100 | 17 | 99 | 18,600 | 1.2 | 60 | 96 | 33,600 | 1.1 |
| 22 | BuNB-b-HFANB | 100/60 | 20 | 96 | 16,000 | 1.2 | 16 h | 60 | 28,000 | 1.1 |
| 23 | BuNB-b-HFANB | 500/200 | 25 | 90 | 79,000 | 1.1 | 16 h | 40 | 106,000 | 1.1 |
| 24 | C$_4$F$_9$NB-b-BuDMMINB | 100/100 | 15 h | 89 | 67,000 | 1.1 | 90 | 100 | 96,000 | 1.4 |

Example 25

Diblock Polymer of HFANB and BuNB (HEANB-b-BuNB)

Example 11 was substantially repeated in this Example 25 except that the polymerization catalyst used in this Example was a compound of Example 4 along with lithium tetrakis(pentafluoroborate), LiFABA, at a 100:100:1:1 molar ratio of monomer 1:monomer 2:catalyst:LiFABA. The polymerization was carried out in a 50:50 (v/v) mixture of toluene and trifluorotoluene at room temperature. The monomer 1, HFANB, was first polymerized at room temperature for 60 minutes, at which time the polymer sample was analyzed by GPC and the number average molecular weight, $M_n$, was determined to be 49,000 with a PDI of 1.2, and the conversion was 89%. Then the monomer 2, BuNB, was added to the reaction mixture and the polymerization was continued for 15 minutes, at which time the monomer conversion was 100%. At which time the polymerization was stopped and

Examples 26A-C

Various Other Diblock and Triblock Polymers

In these Examples 26A-C, the diblock and triblock polymers were synthesized by sequential additions of respective norbornene monomers at room temperature under a nitrogen atmosphere. The total monomer concentration was 4 wt %. A representative procedure for the preparation of BuNB-b-HFANB, Example 26A, included the following. (t-Bu$_3$P)PdMeCl (12 mg, 0.033 mmol), LiFABA (29 mg, 0.033 mmol), toluene (6 g), and TFT (6 g) were placed into a 250 mL round-bottomed flask equipped with a magnetic stirring bar, and the mixture was stirred for 5 min. BuNB (0.5 g, 3.3 mmol) was injected into the flask at once under vigorous stirring. After the complete consumption of BuNB (30 min), a small aliquot of the reaction mixture was taken and quenched with acetonitrile for GPC analysis of the poly(BuNB) block. HFANB (1.8 g, 6.6 mmol) in toluene/TFT (44 g, 50/50 wt %) was then added to the reaction flask. The HFANB was allowed to polymerize for 2 days. The block copolymer was recovered by repeated precipitation into methanol/H$_2$O (50/50 vol %). The obtained polymer was dissolved in THF, and the solution was stirred over charcol, followed by passing through an alumina plug to remove residual Pd catalyst. The resulting filtrate was precipitated into methanol/H$_2$O (50/50 vol %), and subsequently dried under vacuum at 60° C. Other two block polymers, BnNB-b-C$_4$F$_9$NB (Example 26B) and BuNB-b-BnNB-b-NBANB (Example 26C) were prepared using the same procedure except the ratio of each monomer, solvent, reaction time, percent conversion, M$_n$ and PDI are summarized in Table 3A.

TABLE 3A

| Example No. | Polymer[a] | Solvent | Monomer Ratio | Polymerization | | | |
|---|---|---|---|---|---|---|---|
| | | | | Time (h) | Conv. (%)[d] | M$_n$[e] (×10$^{-3}$) | PDI |
| Example 26A (diblock) | BNB-b-HFANB | Tol[b] TFT[c] | 100 200 | 0.5 48 | 100 71 | 17.9 43 | 1.17 1.16 |
| Example 26B (diblock) | BnNB-b-C$_4$F$_9$NB | Tol[b] TFT[c] | 80 200 | 1 36 | 100 94 | 12.7 43.5 | 1.18 1.28 |
| Example 26C (triblock) | BuNB-b-BnNB-b-NBANB | Tol[b] Tol[b] Tol[b] | 70 110 200 | 0.5 1.5 48 | 100 100 28 | 10.1 26.6 34.1 | 1.24 1.19 1.46 |

[a]polymerized from 4 wt % of each monomer in respective solvent;
[b]Tol = toluene;
[c]TFT = α,α,α-trifitiorotoltiene;
[d]determined by NMR;
[e]determined by GPC using differential refractive index (RI) detector, calibrated with narrow distribution polystyrene standards (THF)

Examples 26D-G

Block Copolymers of HFANB-b-BuNB (Different Monomer Ratio)

These Examples 26D-G further illustrate the preparation of diblock polymers having different monomer ratios (i.e., molar ratios) of HFANB and BuNB using (η$^3$-allyl)Pd(i-Pr$_3$P)Cl.

A representative procedure for the preparation of BuNB-h-HFANB, Example 26D, included the following. Into a suitable reaction vessel equipped with a magnetic stirring bar were placed BuNB (0.99 g, 6.6 mmol) and toluene/TFT (19 g, 50/50 wt %), and the mixture was stirred for 5 min before the injection of initiator solution. To a vial with a magnetic stirring bar, 0.23 mL of 0.50 M solution of (η$^3$-allyl)Pd(i-Pr$_3$P)Cl in TFT (39 mg, 0.12 mmol) and 0.23 mL of 0.50 M solution of LiFABA in TFT (100 mg, 0.12 mmol) were added and stirred for 20 min to activate the Pd pro-initiator. 0.30 mL of the (η$^3$-allyl)Pd(i-Pr$_3$P)Cl/Li[FABA] solution (0.075 mmol for each of (η$^3$-allyl)Pd(i-Pr$_3$P)Cl and Li[FABA]) was injected into the flask containing BuNB solution at once under vigorous stirring. After the complete consumption of BuNB (15 min), a small aliquot of the reaction mixture was taken and quenched with acetonitrile for GPC analysis of the first polyBuNB block. HFANB (4.4 g, 16 mmol) in toluene/TFT (83 g, 50/50 wt %) was then added to the reaction flask. The HFANB was allowed to polymerize for 3 h. The block copolymer was recovered by repeated precipitation into MeOH/H$_2$O (50/50 vol %). The polymer so obtained was dissolved in THF, and the solution was stirred over activated charcoal, followed by passing through an alumina plug to remove residual Pd catalyst. The resulting filtrate was precipitated into MeOH/H$_2$O (50/50 vol %), and subsequently dried under vacuum at 60° C. Other block copolymers of BuNB-b-HFANB were prepared using substantially the same procedure, varying the monomer feed composition, the weight fraction of HFANB, W$_{HFANB}$, as summarized in Table 3B. Also summarized in Table 3B are the mole ratio of the block polymer, degree of polymerization, DP, number average molecular weight, M$_n$, as determined by GPC using multi-angle laser scattering (LS) detector (THE), and polydispersity, PDI, as determined by GPC using differential refractive index (RI) detector, calibrated with narrow distribution polystyrene standards (THF).

TABLE 3B

| Example No. | W$_{HFANB}$ | Mole Ratio HFANB:BuNB | DP polyHFANB-polyBuNB | M$_n$ | PDI |
|---|---|---|---|---|---|
| Example 26D | 0.92 | 86:14 | 414-67 | 123,400 | 1.16 |
| Example 26E | 0.81 | 70:30 | 300-130 | 101,900 | 1.12 |
| Example 26F | 0.64 | 50:50 | 203-206 | 86,500 | 1.16 |
| Example 26G | 0.37 | 25:75 | 106-332 | 78,900 | 1.13 |

These results again demonstrate that (η$^3$-allyl)Pd(i-Pr$_3$P)Cl is more reactive initiator resulting higher molecular weight polymers as summarized in Table 3B. All of the polymers of Examples 26D through 26G were also characterized by differential scanning calorimetry (DSC). No glass transition for any of the polymers of Examples 26D through 26G was detected from DSC up to 200° C.

Example 27

Preparation of a Membrane

Single Thickness Film or a Thin Film Composite (TFC) membrane: A polymer formed in accordance with this invention, for instance as specifically disclosed in any one of the Examples 16 to 26, is dissolved in an organic solvent to make a solution which is then filtered. After filtration, trapped gas is removed. The polymer is poured onto a substrate and pulled to form a film, dried and ready for use. In some cases, the film is dried and can be removed from the substrate and used as unsupported film.

Specifically, polymer formed in Example 16 (10 g) was dissolved in THF (100 g) to make a solution which was filtered through a 5 micron nylon filter. After filtration, the solution was allowed to roll overnight on a jar roller to remove trapped gas introduced during the filtration. The polymer solution was poured onto a PAN ultrafiltration substrate and pulled, using a Gardner Film Casting Knife to form a film having an essentially uniform thickness. The film was allowed to dry in the air for one hour followed by annealing at 60° C. for 10 min to form the TFC membrane. In parallel, the film was coated on a glass substrate and the thickness was measured using Dektak profilometer.

Double Thickness Film: Double thickness films are prepared in a similar manner to the single film except that a second layer of the solution is provided over the first film before the first film is removed from substrate, and then pulling the second film. After the second pass is pulled, the double film is dried and then removed from the substrate and ready for use.

For example, the single thickness film example described above is followed, except that is about 5 hours after the first film casting, a second layer is provided by pouring a second aliquot of the polymer solution over the first film and pulling it as was done above with a Gardner Film Casting Knife. After the second pass is pulled, the film is dried in the air overnight.

Example 27A

Membranes of Polymers of Examples 26D-G

Thin film composite membranes with dense polymer coating layer of block polymers of Examples 26D-G on the top surface were prepared via simple blade coating method using PAN membrane as a support. The block polymers of Examples 26D-G were dissolved in toluene/TFT/THF mixture (40/40/20 wt %) to prepare 10 wt % solution and filtered through 0.45 μm-pore PTFE filter. Each of the polymer solution so formed was poured onto a PAN membrane supported by a pane of glass and pulled by a film casting knife (25 μm gap height) to form a film with uniform thickness. The coatings were dried slowly and annealed in a THF chamber for 2 h to allow microphase separation for the block copolymers. After drying the membrane on a hot plate at 60° C. for 1 hour the membrane was subsequently dried under vacuum at 60° C. overnight.

Example 28

Pervaporation Test

The membrane was cut into 2 inch diameter circles for installation into a capsule that was then placed in the pervaporation testing device. The charge liquid in the testing device was heated to desired temperature circulating in by-pass mode and then circulated through the membrane housing at 450 mL/min in the continuous mode to check for any leaks. After this check was completed a vacuum was pulled on the dry side of the membrane and any permeate was collected into a cooled trap (cooled with liquid nitrogen). The system was allowed to run for three hours, collected permeate was warmed to room temperature and evaluated.

Evaluation of the Permeate

The room temperature permeate collected as described above was separated into a two-phase liquid. To this permeate, MeOH was added to make the phases miscible, thus providing a single phase permeate. The single phase permeate (1 gram) was added to a GC sampling vial containing 0.02 g PGMEA and mixed thoroughly. A sample from the vial was then injected into a Gas Chromatograph where the % butanol or % phenol was determined by evaluating the area of the butanol or phenol peak with respect to the PGMEA standard.

In addition to forming a flat sheet membrane supported on PAN ultrafiltration substrate, the possibility of forming hollow fibers that encompass the block polymer embodiments of the present invention can be evaluated. The following procedure is used to successfully form hollow fibers for further evaluation.

Example 29

Hollow Fiber Membrane Film Making

A block polymer formed in accordance with this invention, for instance as specifically disclosed in any one of the Examples 16 to 26, is dissolved in an organic solvent and filtered to remove particles. This solution is then pressure transferred through the outer bore of a spinneret while a mixture of a solvent and salt is simultaneously pressure transferred through the inner bore of the spinneret. These pressure transferred materials are directed to a precipitating bath to provide hollow fibers. The dimensions of the hollow fibers can be controlled by the size of the inner/outer bores and the pressures under which the solutions are transferred.

For example, a block copolymer of Example 18, BUNB-b-HFANB (1:1) is dissolved in THF at 10 wt. % and filtered through a 100 micron filter to remove particles. This solution is then pressure transferred through the outer bore of a double-bore spinneret having an outside diameter of 1.0 mm and an inside diameter of 0.5 mm while a mixture of 20/80 MeOH/5 wt. % LiCl (aq.) solution is simultaneously pressure transferred through the inner bore of the spinneret. These pressure transferred materials are directed to a precipitating bath (20/80 MeOH/water) where hollow fibers are observed and evaluated. The dimensions of the hollow fibers removed from the bath can be confirmed by SEM.

Example 30

Forming Thin Film Composite Hollow Fibers

Generally speaking, a polymer formed in accordance with this invention, for instance as specifically disclosed in any one of the Examples 16 to 26, is dissolved in a suitable solvent (e.g., THF) at a suitable concentration (e.g., 10 wt. %) and filtered through a 100 micron filter to remove particles. A hollow fiber microfiltration or ultrafiltration membrane (e.g., 0.1 micron PVDF or 3000 MWCO polysulfone) with the inner lumen blocked off is dipped into the block polymer solution and then pulled out of the solution. The solvent is removed by drying the fiber at suitable conditions (e.g., 23-60° C. for 0.5-12 h). The dimensions of the hollow fibers removed from the bath can be confirmed by SEM.

Example 31

Comparative Operability of Single Thickness Films Made from Different Block Polymer Compositions of this Invention and other Polymers A comparison of block polymers of this invention and a random polymer composition was performed to observe selective separation performance of n-butanol in a pervaporation test. The two dependent variables that were examined were flux and percent organics in the permeate. The feed solution concentration was varied (1%). A heat bath was used to heat the feed solution to 65° C. Through heat loss, this gives a housing temperature of about 60° C. In order to collect the permeate samples vacuum traps in liquid nitrogen were used. The vacuum was 0.4 in Hg (10 Torr), The feed solution was pumped into the system by a diaphragm pump at 450 mL/min. A three hour test was used to collect samples. Several different block polymers of BuNB/HFANB prepared in accordance with Example 18 was compared with a 1:1 random copolymer of BuNB/HFANB, all used as a thin film composite membrane prepared in accordance with procedures as described in Example 26. The thicknesses of the films were varied and were from about 2 microns to about 4 microns. The flux number in Table 4 was normalized for the film thickness of 3 μm. The results are summarized in Table 4.

TABLE 4

Pervaporation Performance with 1% n-butanol feed

| Membrane Sample No. | Polymer (monomer ratio) | Casting solvent | Flux, (g/m²h) | BuOH in permeate, (%) | Phase separation |
|---|---|---|---|---|---|
| 1 | Random BuNB-HFANB (1:1) | THF | 800 | 20 | n.m. |
| 2 | Block BuNB-b-HFANB (1:1) | THF | 620 | 18 | n.m. |
| 3 | Block BuNB-b-HFANB (2:1) | Toluene | 930 | 14 | No |
| 4 | Block BuNB-b-HFANB-b-BuNB (1:1:1) | THF | 670 | 17 | n.m. |
| 5 | Block BuNB-b-HFANB (1:2) | THF | 600 | 20 | No |
| 6 | Block HFANB-b-BuNB-b-HFANB (1:1:1) | Toluene/THF | 1700 | 20 | Yes | n.m. = not measured

It is quite apparent from Table 4 that the membrane sample No. 6 made from a triblock polymer of HFANB-b-BuNB-b-HFANB (1:1:1) exhibits much superior separation performance than the membrane sample Nos. 1 formed from 1:1 random copolymer of BuNB/HFANB. Most notably, as summarized in Table 4, significantly higher flux was achieved using the triblock polymer (HFANB-b-BuNB-b-HFANB) at the same butanol concentration in permeate when compared with similar thickness of films formed from the random copolymer (BuNB/HFANB random copolymer of membrane sample No. 1). It should further be noted that only membrane formed from triblock polymer, that is, membrane sample No. 6 exhibited a phase separation as observed by the atomic force micrographs (AFM) (FIG. 5), which clearly shows different surface morphology when compared with AFM of the diblock copolymers, BuNB-b-HFANB (2:1), sample No. 3 (FIG. 4), and BuNB-b-HFANB (1:2), sample No. 5, (FIG. 3) both of which exhibited no phase separation under the conditions these samples were made, thus featuring no nanoscale structure. On the other hand, the membrane formed from the triblock polymer, HFANB-b-BuNB-b-HFANB, sample No. 6, FIG. 5 shows a well-ordered structure, which may be responsible for the observed high flux, among other factors.

Example 32

Pervaporation Test with Membranes of Example 27A

The membranes formed from Example 27A were tested substantially using the procedures as set forth in Example 28 with the following exceptions. The effective area of the membrane was 13.38 cm². A 1 wt % n-BuOH aqueous solution was employed as the feed to determine the permeation flux and the separation factor. The feed flow rate was controlled at 450 mL min⁻¹ by a diaphragm pump. The feed temperature was controlled by a heat exchanger connected to a temperature-controllable water circulator. The feed was circulated without membrane for 30 min to be heated to a desired temperature. After the feed was circulated with the membrane for 1 min to check for any leakage, permeate was collected into a cold trap immersed in liquid nitrogen using a vacuum pump. The pressure on the permeate side of the membrane was kept below 10 Torr monitored by a vacuum gauge. The cold trap was weighed to calculate total flux (J) before and after the pervaporation experiment. The composition of permeate was determined by $^1$H NMR using acetone-$d_6$ as a solvent; a small amount of anhydrous ethanol was added to the permeate to make the phases miscible, thus providing a single phase solution before the NMR analysis. Three different membranes were prepared for is each polymer of Examples 26D through 26G, and analyzed at the same experimental condition to ensure the reliability of the results. For the stability test, two cold traps were used to collect permeate alternatively and the permeate through the membrane was replenished to the feed to keep the n-BuOH feed concentration as 1 wt %. The permeation total flux (J) and separation factor (SF) were calculated using the equation provided above.

Figure 6B:
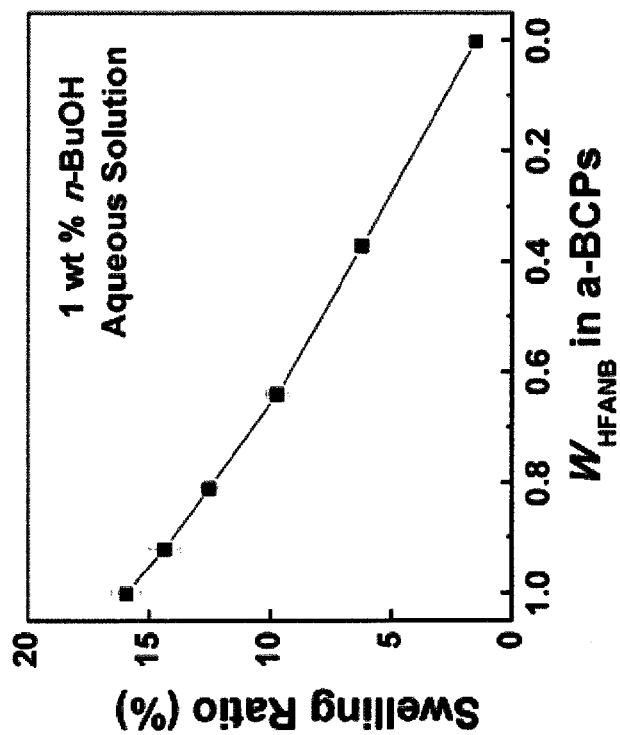
FIG. 6(b) shows graphical relationship between swelling ratio and various weight fractions of HFANB ($W_{HFANB}$) in the vinyl addition block copolymer (a-BCP) of one of the embodiments of the invention.
Figure 6A:
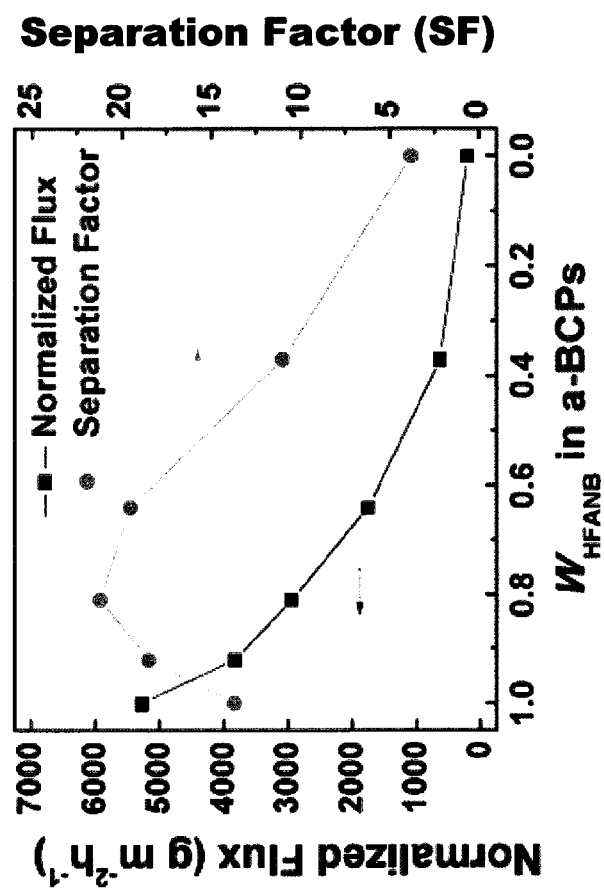
FIG. 6(a) shows graphical relationship between normalized flux and various weight fractions of HFANB ($W_{HFANB}$) in the block polymer as well as graphical relationship between separation factor (SF) and various weight fractions of HFANB ($W_{HFANB}$) in the vinyl addition block copolymer (a-BCP) of one of the embodiments of the invention.

The pervaporation experiments were carried out at 37° C. and at 60° C. With a higher temperature at 60° C. in the feed solution, higher flux and separation factor were obtained. The measured flux for each of the membrane samples was normalized by using the equation $J'=J\times(t/2)$, where J' is the normalized flux, J is the measured flux and t is the thickness of the membrane film. The normalized flux eliminates the effect of the different membrane thickness on flux. FIG. 6(*a*) shows the normalized flux and separation factor (SF) obtained for each of the membrane formed from the polymers of Examples 26D through 26G, labeled as a-BCPs (vinyl addition block copolymers), where $W_{HFANB}$ is the weight fraction of HFANB in each of the polymers of Examples 26D through 26G. Also shown in FIG. 6(*a*) is the normalized flux and SF obtained for homopolymer, poly-HFANB (where $W_{HFANB}$ is 1.0) and homopolymer, poly-BuNB (where $W_{HFANB}$ is 0.0). It is evident from this data that polymer of Example 26E, the polymer with a $W_{HFANB}$ of 0.81 (HFANB:BuNB=70:30 mole ratio) exhibits the highest separation factor of 21.2 at 60° C. The flux then gradually decreases with decreasing $W_{HFANB}$ perhaps due to the decrease in swelling ratio as shown in FIG. 6(*b*). The observed separation factor (SF) for poly-HFANB membrane was found to be only 13.7 perhaps due to its relatively large swelling in 1 wt % n-BuOH aqueous solution, which increases the permeation of water molecules (FIG. 6(*b*)).

The following two Comparative Examples 1 and 2 are provided here to illustrate that certain of the known catalysts in the literature exhibit poor catalytic activity when compared with the catalytic activity of the compounds of this invention under similar reaction conditions.

Comparative Example 1

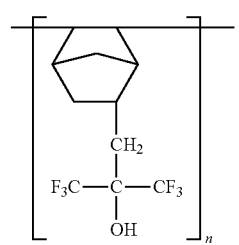

Homopolymer of Norbornenyl-2-trifluoromethyl-3,3,3-trifluoropropan-2-ol (HFANB)

Example 11 was substantially repeated except that the catalyst employed was to palladium(acetoxy(bis(triisopropylphosphine))(acetonitrile)tetrakis(pentafluorophenyl)borate [Pd(OAc)(P-i-Pr$_3$)$_2$(CH$_3$CN)]FABA. The conversion of the monomer was found to be only 25%. The polymer was characterized by GPC: M$_w$=12,000; M$_n$=6,600; PDI=16.

Comparative Example 2

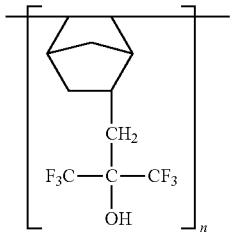

Homopolymer of Norbornenyl-2-trifluoromethyl-3,
3,3-trifluoropropan-2-ol (HFANB)

Example 11 was substantially repeated in this Comparative Example 2 except that the catalyst employed was palladium(acetylacetonato)(triisopropylphosphine))(acetonitrile)tetrakis(pentafluorophenyl)borate [Pd(acac)(P-i-Pr$_3$)(CH$_3$CN)]FABA. No polymerization took place under these conditions.

Comparative Example 3

ROMP PolyHFANB-b-PolyBuNB (r-BCP81)

A ROMP block copolymer of HFANB and BuNB (r-BCP81) was synthesized by sequential additions of the monomers at room temperature under a nitrogen atmosphere. The block copolymer was designated as r-BCP81, where 'r' indicates the 'ROMP polymer', 'BCP' indicates the 'block copolymer', and '81' indicates the weight composition (81 wt %) of HFANB monomeric unit in the polymers, respectively. The initial monomer concentration was 4 wt %, and the subsequent HFANB monomer charge was made as 4 wt % solution. BuNB (0.8 g, 5.3 mmol) and toluene (19 g) were placed into a 250 mL round-bottomed flask equipped with a magnetic stirring bar, and the mixture was stirred for 5 min before the injection of initiator solution. To a vial with a magnetic stirring bar, bis(tricyclohexylphosphine)benzylidene ruthenium(IV) dichloride (0.034 g, 0.05 mmol), tricyclohexylphosphine (PCy$_3$, 0.057 g, 0.2 mmol), and toluene (4 mL) were added and stirred for 5 min. The initiator solution was injected to into the flask containing BuNB solution at once under vigorous stirring. After the complete consumption of BuNB (1 h), a small aliquot of the reaction mixture was taken and terminated with an excess of ethyl vinyl ether for GPC analysis of the first polyBuNB block. HFANB (3.4 g, 12 mmol) in toluene (81 g) was then added to the reaction flask. The HFANB was allowed to polymerize for 6 h. The block copolymer was terminated with an excess of ethyl vinyl ether and recovered by evaporating the solvent under N$_2$ flow. The polymer so obtained was dissolved in 1 L of cyclohexane/THF mixture (95/5 vol %) and then charged to a 2 L Parr reactor. Hydrogenation reaction was conducted using Pd(0) heterogeneous catalyst supported on CaCO$_3$ (8 g) at 100° C. and 400-500 prig H$_2$ for 2 days. The progress of the reaction was tracked by $^1$H NMR and greater than 99.9% saturation of the (Actinic double bonds was confirmed. After filtration of the catalyst, the resulting filtrate was concentrated and precipitated into MeOH/H$_2$O (50/50 vol %), and subsequently dried under vacuum at 60° C.

Comparative Example 4

Random Vinyl Addition Copolymer of
HFANB/BuNB (a-RCP81)

A vinyl addition random copolymer of HFANB and BuNB (a-RCP81) was synthesized via several separate charges of BuNB solutions into a reaction flask during the polymerization, at room temperature under a nitrogen atmosphere. The random copolymer was designated as a-RCP81, where 'a' indicates the 'vinyl addition polymer', 'RCP' indicates the 'random copolymer', and '81' indicates the weight composition (81 wt %) of HFANB monomeric unit in the polymers, respectively. The initial monomer concentration was 5 wt %, and all subsequent BuNB charges were made as 5 wt % solutions. HFANB (4.4 g, 16 mmol), BuNB (0.5 g, 3.3 mmol), and toluene/TFT (94 g, 50/50 wt %) were placed into a 250 mL round-bottomed flask equipped with a magnetic stirring bar, and the mixture was stirred for 5 min before the injection of initiator solution. To a vial with a magnetic stirring bar, 0.23 mL of 0.50 M solution of ($\eta^3$-allyl)Pd(i-Pr$_3$P)Cl in TFT (39 mg, 0.12 mmol) and 0.23 mL of 0.5 M solution of Li[FABA] in TFT (100 mg, 0.12 mmol) were added and stirred for 20 min to activate the Pd pro-initiator. 0.30 mL of the ($\eta^3$-allyl)Pd(i-Pr$_3$P)Cl/Li[FABA] solution (0.075 mmol for each of ($\eta^3$-allyl)Pd(i-Pr$_3$P)Cl and Li[FABA]) was injected into the flask containing monomer solution at once under vigorous stirring. Subsequent BuNB solutions (0.2, 0.15, 0.10, and 0.05 g of BuNB) were then added to the reaction flask at 10, 30, 45, and 60 min after the initiator injection, respectively. The monomers were allowed to polymerize for 3 h. The random copolymer was recovered by repeated precipitation into MeOH/H$_2$O (50/50 vol %). The polymer so obtained was dissolved in THF, and the solution was stirred over activated charcoal, followed by passing through an alumina plug to remove residual Pd catalyst. The resulting filtrate was precipitated into MeOH/H$_2$O (50/50 vol %), and subsequently dried under vacuum at 60° C.

Comparative Example 5

Pervaporation Test with r-BCP81, a-RCP81 and
a-BCP81

Figure 7B:
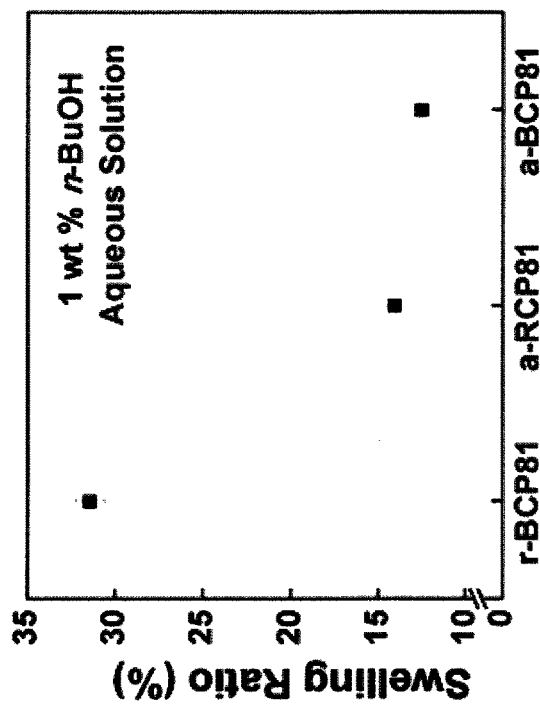
FIG. 7(b) shows swelling ratio observed for one of the vinyl addition block copolymers (a-BCP81) of this invention, which is compared with a block polymer made by ring opening metathesis polymerization (ROMP) method (r-BCP81) and a random vinyl addition copolymer (a-RCP81).
Figure 7A:
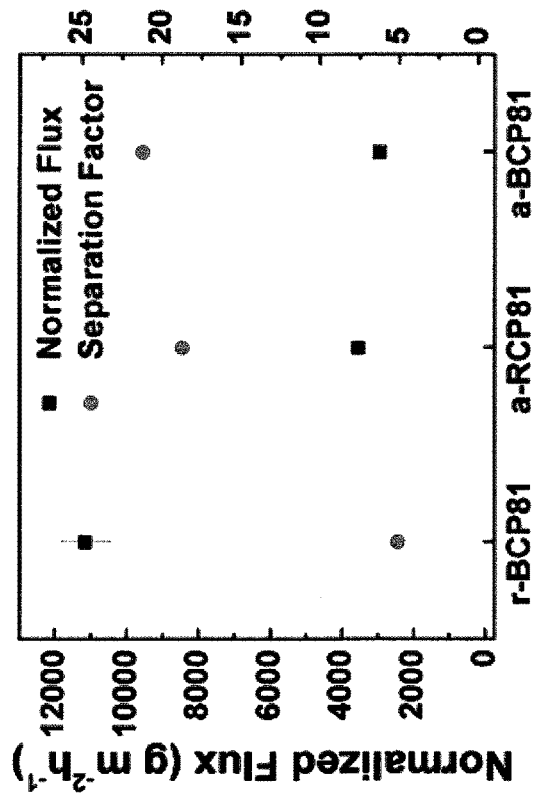
FIG. 7(a) shows normalized flux and separation factor (SF) obtained for one of the vinyl addition block copolymers (a-BCP81) of this invention, which is compared with a block polymer made by ring opening metathesis polymerization (ROMP) method (r-BCP81) and a random vinyl addition copolymer (a-RCP81)).

The polymers from Comparative Examples 3 and 4 were used to make the membranes substantially using the procedures as set forth in Example 27A and then tested in accordance with the procedures as set forth in Example 32 for the separation of 1 wt % n-BuOH. FIG. 7($a$) shows the results obtained. It is clear from FIG. 7($a$), the membrane formed form the ROMP polymer, r-BCP81, of Comparative Example 3 leads to very low separation factor of 5.1. This is perhaps due to the fact that ROMP polymer, r-BCP81, with its flexible backbone structure leads to large swelling (~31%) in 1 wt % n-BuOH aqueous solution as shown in FIG. 7($b$).

The separation factor of the membrane formed from polymer of Example 26E, a-BCP81 membrane (21.2), was found to be higher than that of the membrane formed from polymer of Comparative Example 4, a-RCP81 membrane (18.5), although the flux of a-BCP81 is slightly lower than that of a-RCP81 membrane. This should be ascribed to the microphase separation of a-BCP81 as described herein. The phase-separated polyBuNB domains in a-BCP81 suppress the swelling of the polyHFANB domains effectively, while the randomly distributed BuNB segments in a-RCP81 cannot provide enough suppression for the polyHFANB swelling due to molecular dilution of BuNB in the polyHFANB matrix (FIG. 7(b)). Therefore, it should be noted that the high $T_g$ backbone structure and block copolymer architecture of the polymers of this invention are important to enhace the butanol selectivity in the pervaporation process.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A block polymer of the formula (VI):

$$(A)_m\text{-}b\text{-}(B)_n \qquad (VI);$$

where m and n are integers of at least 15;
b denotes a bond;
A and B are different from each other and independently selected from a repeat unit represented by formula (IVA), said repeat unit is derived from a monomer of formula (IV):

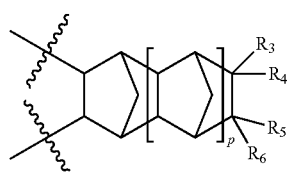

(IVA)

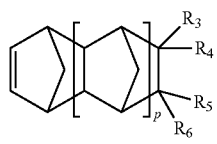

(IV)

wherein:
〰️ denotes a place of bonding with another repeat unit;
p is an integer 0, 1 or 2;
$R_3$, $R_4$, $R_5$ and $R_6$ are the same or different and each independently of one another is selected from hydrogen, linear or branched ($C_1$-$C_{16}$)alkyl, hydroxy($C_1$-$C_{16}$)alkyl, perfluoro($C_1$-$C_{12}$)alkyl, ($C_3$-$C_{12}$)cycloalkyl, ($C_6$-$C_{12}$)bicycloalkyl, ($C_7$-$C_{14}$)tricycloalkyl, ($C_6$-$C_{10}$)aryl, ($C_6$-$C_{10}$)aryl($C_1$-$C_3$)alkyl, perfluoro($C_6$-$C_{10}$)aryl, perfluoro($C_6$-$C_{10}$)aryl($C_1$-$C_3$)alkyl, di($C_1$-$C_2$)alkylmaleimide($C_3$-$C_6$)alkyl, di($C_1$-$C_2$)alkylmaleimide($C_2$-$C_6$)alkoxy($C_1$-$C_2$)alkyl, hydroxy, ($C_1$-$C_{12}$)alkoxy, ($C_3$-$C_{12}$)cycloalkoxy, ($C_6$-$C_{12}$)bicycloalkoxy, ($C_7$-$C_{14}$)tricycloalkoxy, ($C_6$-$C_{10}$)aryloxy($C_1$-$C_3$)alkyl, ($C_5$-$C_{10}$)heteroaryloxy($C_1$-$C_3$)alkyl, ($C_6$-$C_{10}$)aryloxy, ($C_5$-$C_{10}$)heteroaryloxy or ($C_1$-$C_6$)acyloxy, where each of the aforementioned substituents are optionally substituted with a group selected from halogen or hydroxy.

2. The block polymer of claim 1 wherein said block polymer further comprises a third repeat unit and represented by formula (VII):

$$(A)_m\text{-}b\text{-}(B)_n\text{-}b\text{-}(C)_o \qquad (VII);$$

where m, n and b are as defined in claim 1 and o is an integer of at least 15;
C is same or different from A or B and independently selected from a repeat unit represented by formula (IVA), said repeat unit is derived from a monomer of formula (IV) as defined in claim 1.

3. The block polymer of claim 2, wherein the block molar ratio of A:B:C is from 1:1:1 to 1:4:1 to 1:1:4.

4. The block polymer of claim 2, wherein the block molar ratio of A:B:C is 1:1:1.

5. The block polymer of claim 2, wherein the block molar ratio of A:B:C is 1:2:1.

6. The block polymer of claim 2, wherein C is derived from a monomer selected from the group consisting of:
5-butylbicyclo[2.2.1]hept-2-ene (BuNB);
5-hexylbicyclo[2.2.1]hept-2-ene (HexNB);
5-octylbicyclo[2.2.1]hept-2-ene (OctNB);
5-perfluoroethylbicyclo[2.2.1]hept-2-ene ($C_2F_5$NB);
5-n-perfluorobutylbicyclo[2.2.1]hept-2-ene ($C_4F_9$NB);
5-perfluorohexylbicyclo[2.2.1]hept-2-ene ($C_6F_{13}$NB);
norbornenyl-2-trifluoromethyl-3,3,3-trifluoropropan-2-ol (HFANB);
1-(3-(bicyclo[2.2.1]hept-5-en-2-yl)propyl)-3,4-dimethyl-1H-pyrrole-2,5-dione (PrDMMINB);
1-(4-(bicyclo[2.2.1]hept-5-en-2-yl)butyl)-3,4-dimethyl-1H-pyrrole-2,5-dione (BuDMMINB);
1-(6-(bicyclo[2.2.1]hept-5-en-2-yl)hexyl)-3,4-dimethyl-1H-pyrrole-2,5-dione (HexDMMINB);
5-phenethylbicyclo[2.2.1]hept-2-ene (PENB); and
2-(bicyclo [2.2.1]hept-5-en-2-yl)bicyclo[2.2.1]heptane (NBANB).

7. The block polymer of claim 2, wherein C is derived from a monomer selected from the group consisting of:
5-butylbicyclo[2.2.1]hept-2-ene (BuNB);
5-hexylbicyclo[2.2.2.1]hept-2-ene (HexNB);
5-n-perfluorobutylbicyclo[2.2.1]hept-2-ene ($C_4F_9$NB);
norbornenyl-2-trifluoromethyl-3,3,3-trifluoropropan-2-ol (HFANB);
1-(4-(bicyclo[2.2.1]hept-5-en-2-yl)butyl)-3,4-dimethyl-1H-pyrrole-2,5-dione (BuDMMINB); and
2-(bicyclo[2.2.1]hept-5-en-2-yl)bicyclo [2.2.1]heptane (NBANB).

8. The block polymer of claim 2, which is selected from the group consisting of:
a block polymer derived from 5-butylbicyclo[2.2.1]hept-2-ene, norbornenyl-2-trifluoromethyl-3,3,3-trifluoropropan-2-ol and 5-butylbicyclo[2.2.1]hept-2-ene (BuNB-b-HFANB-b-BuNB); and
a block polymer derived from norbornenyl-2-trifluoromethyl-3,3,3-trifluoropropan-2-ol, 5-butylbicyclo[2.2.1]hept-2-ene, and norbornenyl-2-trifluoromethyl-3,3,3-trifluoropropan-2-ol (HFANB-b-BuNB-b-HFANB).

9. The block polymer of claim 1, wherein the block molar ratio of A:B is from 1:1 to 1:4.

10. The block polymer of claim 1, wherein the block molar ratio of A:B is from 1:1 to 1:2.

11. The block polymer of claim 1, wherein the block molar ratio of A:B is 1:1.

12. The block polymer of claim 1, wherein A is derived from a monomer selected from the group consisting of:
5-butylbicyclo[2.2.1]hept-2-ene (BuNB);
5-hexylbicyclo[2.2.1]hept-2-ene (HexNB);
5-octylbicyclo[2.2.1]hept-2-ene (OctNB);
5-perfluoroethylbicyclo[2.2.1]hept-2-ene ($C_2F_5$NB);
5-n-perfluorobutylbicyclo[2.2.1]hept-2-ene ($C_4F_9$NB);
5-perfluorohexylbicyclo[2.2.1]hept-2-ene ($C_6F_{13}$NB);

norbornenyl-2-trifluoromethyl-3,3,3-trifluoropropan-2-ol (HFANB);
1-(3-(bicyclo[2.2.1]hept-5-en-2-yl)propyl)-3,4-dimethyl-1H-pyrrole-2,5-dione (PrDMMINB);
1-(4-(bicyclo[2.2.1]hept-5-en-2-yl)butyl)-3,4-dimethyl-1H-pyrrole-2,5-dione (BuDMMINB);
1-(6-(bicyclo[2.2.1]hept-5-en-2-yl)hexyl)-3,4-dimethyl-1H-pyrrole-2,5-dione (HexDMMINB);
5-phenethylbicyclo[2.2.1]hept-2-ene (PENB); and
2-(bicyclo[2.2.1]hept-5-en-2-yl)bicyclo[2.2.1]heptane (NBANB).

13. The block polymer of claim 1, wherein B is derived from a monomer selected from the group consisting of:
5-butylbicyclo[2.2.1]hept-2-ene (BuNB);
5-hexylbicyclo[2.2.1]hept-2-ene (HexNB);
5-octylbicyclo[2.2.1]hept-2-ene (OctNB);
5-perfluoroethylbicyclo[2.2.1]hept-2-ene ($C_2F_5NB$);
5-n-perfluorobutylbicyclo[2.2.1]hept-2-ene ($C_4F_9NB$);
5-perfluorohexylbicyclo[2.2.1]hept-2-ene ($C_6F_{13}NB$);
norbornenyl-2-trifluoromethyl-3,3,3-trifluoropropan-2-ol (HFANB);
1-(3-(bicyclo[2.2.1]hept-5-en-2-yl)propyl)-3,4-dimethyl-1H-pyrrole-2,5-dione (PrDMMINB);
1-(4-(bicyclo[2.2.1]hept-5-en-2-yl)butyl)-3,4-dimethyl-1H-pyrrole-2,5-dione (BuDMMINB);
1-(6-(bicyclo[2.2.1]hept-5-en-2-yl)hexyl)-3,4-dimethyl-1H-pyrrole-2,5-dione (HexDMMINB);
5-phenethylbicyclo[2.2.1]hept-2-ene (PENB); and
2-(bicyclo[2.2.1]hept-5-en-2-yl)bicyclo[2.2.1]heptane (NBANB).

14. The block polymer of claim 1, wherein A is derived from a monomer selected from the group consisting of:
5-butylbicyclo[2.2.1]hept-2-ene (BuNB);
5-hexylbicyclo[2.2.1]hept-2-ene (HexNB);
5-n-perfluorobutylbicyclo[2.2.1]hept-2-ene ($C_4F_9NB$);
norbornenyl-2-trifluoromethyl-3,3,3-trifluoropropan-2-ol (HFANB);
1-(4-(bicyclo[2.2.1]hept-5-en-2-yl)butyl)-3,4-dimethyl-1H-pyrrole-2,5-dione (BuDMMINB); and
2-(bicyclo[2.2.1]hept-5-en-2-yl)bicyclo[2.2.1]heptane (NBANB).

15. The block polymer of claim 1, wherein B is derived from a monomer selected from the group consisting of:
5-butylbicyclo[2.2.1]hept-2-ene (BuNB);
5-hexylbicyclo[2.2.1]hept-2-ene (HexNB);
5-n-perfluorobutylbicyclo[2.2.1]hept-2-ene ($C_4F_9NB$);
norbornenyl-2-trifluoromethyl-3,3,3-trifluoropropan-2-ol (HFANB);
1-(4-(bicyclo[2.2.1]hept-5-en-2-yl)butyl)-3,4-dimethyl-1H-pyrrole-2,5-dione (BuDMMINB); and
2-(bicyclo[2.2.1]hept-5-en-2-yl)bicyclo[2.2.1]heptane (NBANB).

16. The block polymer of claim 1, which is selected from the group consisting of:
a block polymer derived from 5-hexylbicyclo[2.2.1]hept-2-ene and norbornenyl-2-trifluoromethyl-3,3,3-trifluoropropan-2-ol (HexNB-b-HFANB);
a block polymer derived from 5-butylbicyclo[2.2.1]hept-2-ene and norbornenyl-2-trifluoromethyl-3,3,3-trifluoropropan-2-ol (BuNB-b-HFANB);
a block polymer derived from 5-butylbicyclo[2.2.1]hept-2-ene and 1-(4-(bicyclo[2.2.1]hept-5-en-2-yl)butyl)-3,4-dimethyl-1H-pyrrole-2,5-dione ($C_4F_9$NB-b-BuDMMINB);
a block polymer of derived from norbornenyl-2-trifluoromethyl-3,3,3-trifluoropropan-2-ol and 2-(bicyclo[2.2.1]hept-5-en-2-yl)bicyclo[2.2.1]heptane (HFANB-b-NBANB); and
a block polymer of derived from 5-hexylbicyclo[2.2.1]hept-2-ene and 2-(bicyclo[2.2.1]hept-5-en-2-yl)bicyclo[2.2.1]heptane (HexNB-b-NBANB).

17. A process for the preparation of a block polymer of formula (VI):

$$(A)_m\text{-}b\text{-}(B)_n \qquad (VI);$$

where m and n are integers of at least 15;
b denotes a bond;
A and B are respectively first and second monomeric repeat units different from each other and independently derived from a respective first and second monomer of formula (IV):

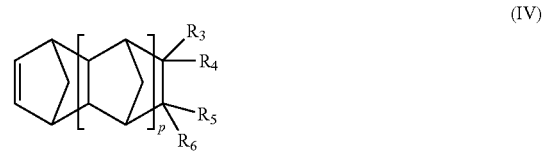

wherein:
∿∿ denotes a place of bonding with another repeat unit;
p is an integer 0, 1 or 2;
$R_3$, $R_4$, $R_5$ and $R_6$ are the same or different and each independently of one another is selected from hydrogen, linear or branched ($C_1$-$C_{16}$)alkyl, hydroxy($C_1$-$C_{16}$)alkyl, perfluoro($C_1$-$C_{12}$)alkyl, ($C_3$-$C_{12}$)cycloalkyl, ($C_6$-$C_{12}$)bicycloalkyl, ($C_7$-$C_{14}$)tricycloalkyl, ($C_6$-$C_{10}$)aryl, ($C_6$-$C_{10}$)aryl($C_1$-$C_3$)alkyl, perfluoro($C_6$-$C_{10}$)aryl, perfluoro($C_6$-$C_{10}$)aryl($C_1$-$C_3$)alkyl, di($C_1$-$C_2$)alkylmaleimide($C_3$-$C_6$)alkyl, di($C_1$-$C_2$)alkylmaleimide($C_2$-$C_6$)alkoxy($C_1$-$C_2$)alkyl, hydroxy, ($C_1$-$C_{12}$)alkoxy, ($C_3$-$C_{12}$)cycloalkoxy, ($C_6$-$C_{12}$)bicycloalkoxy, ($C_7$-$C_{14}$)tricycloalkoxy, ($C_6$-$C_{10}$)aryloxy($C_1$-$C_3$)alkyl, ($C_5$-$C_{10}$)heteroaryloxy($C_1$-$C_3$)alkyl, ($C_6$-$C_{10}$)aryloxy, ($C_5$-$C_{10}$)heteroaryloxy or ($C_1$-$C_6$)acyloxy, where each of the aforementioned substituents are optionally substituted with a group selected from halogen or hydroxy;
comprising reacting said first monomer with a palladium compound to form the first polymer block; and reacting said second monomer which is distinct from the first monomer to form the block polymer.

18. The process of claim 17, which further comprises reacting a third monomer to form a block polymer of formula (VII):

$$(A)_m\text{-}b\text{-}(B)_n\text{-}b\text{-}(C)_o \qquad (VII);$$

where m, n and b are as defined in claim 17 and o is an integer of at least 15; and
C is same or different from A or B and independently selected from a repeat unit represented by formula (IVA), said repeat unit is derived from a monomer of formula (IV) as defined in claim 17.

19. The process of claim 18, wherein the polymer formed is selected from the group consisting of:
a block polymer derived from 5-butylbicyclo[2.2.1]hept-2-ene, norbornenyl-2-trifluoromethyl-3,3,3-trifluoropropan-2-ol and 5-butylbicyclo[2.2.1]hept-2-ene (BuNB-b-HFANB-b-BuNB); and a block polymer derived from norbornenyl-2-trifluoromethyl-3,3,3-trifluoropropan-2-ol, 5-butylbicyclo[2.2.1]hept-2-ene, and norbornenyl-2-trifluoromethyl-3,3,3-trifluoropropan-2-ol (HFANB-b-BuNB-b-HFANB).

20. The process of claim 17, wherein the block polymer formed is selected from the group consisting of:

a block polymer derived from 5-hexylbicyclo[2.2.1]hept-2-ene and norbornenyl-2-trifluoromethyl-3,3,3-trifluoropropan-2-ol (HexNB-b-HFANB);

a block polymer derived from 5-butylbicyclo[2.2.1]hept-2-ene and norbornenyl-2-trifluoromethyl-3,3,3-trifluoropropan-2-ol (BuNB-b-HFANB);

a block polymer derived from 5-butylbicyclo[2.2.1]hept-2-ene and 1-(4-(bicyclo[2.2.1]hept-5-en-2-yl)butyl)-3,4-dimethyl-1H-pyrrole-2,5-dione ($C_4F_9$NB-b-BuDMMINB);

a block polymer of derived from norbornenyl-2-trifluoromethyl-3,3,3-trifluoropropan-2-ol and 2-(bicyclo[2.2.1]hept-5-en-2-yl)bicyclo[2.2.1]heptane (HFANB-b-NBANB); and a block polymer of derived from 5-hexylbicyclo[2.2.1]hept-2-ene and 2-(bicyclo[2.2.1]hept-5-en-2-yl)bicyclo[2.2.1]heptane (HexNB-b-NBANB).

\* \* \* \* \*